United States Patent
Baxter et al.

(10) Patent No.: US 11,285,220 B2
(45) Date of Patent: Mar. 29, 2022

(54) MATERIALS AND METHODS RELATING TO LINKERS FOR USE IN PROTEIN DRUG CONJUGATES

(71) Applicant: Iksuda Therapeutics Limited, Newcastle upon Tyne (GB)

(72) Inventors: Anthony David Baxter, Much Hadham (GB); Christopher Michael Birchall, Newcastle upon Tyne (GB); David James Mansell, Newcastle upon Tyne (GB); Justyna Helena Mysliwy, Newcastle upon Tyne (GB); Jenny Thirlway, York (GB)

(73) Assignee: Iksuda Therapeutics Limited, Newcastle upon Tyne (GB)

(*) Notice: Subject to any disclaimer, the term of this patent is extended or adjusted under 35 U.S.C. 154(b) by 0 days.

(21) Appl. No.: 15/502,026

(22) PCT Filed: Oct. 27, 2015

(86) PCT No.: PCT/GB2015/053227
§ 371 (c)(1),
(2) Date: Feb. 6, 2017

(87) PCT Pub. No.: WO2016/067021
PCT Pub. Date: May 6, 2016

(65) Prior Publication Data
US 2017/0232108 A1     Aug. 17, 2017
US 2018/0092981 A9     Apr. 5, 2018

(30) Foreign Application Priority Data

Oct. 27, 2014 (GB) .................................. 1419108
Feb. 23, 2015 (GB) .................................. 1503012

(51) Int. Cl.
A61K 38/06     (2006.01)
A61K 47/68     (2017.01)
(Continued)

(52) U.S. Cl.
CPC ........ *A61K 47/6813* (2017.08); *A61K 31/704* (2013.01); *A61K 38/063* (2013.01);
(Continued)

(58) Field of Classification Search
None
See application file for complete search history.

(56) References Cited

U.S. PATENT DOCUMENTS 5,900,461 A    5/1999 Harris
7,659,241 B2   2/2010 Senter et al.
(Continued)

FOREIGN PATENT DOCUMENTS

CN    102206267 A    10/2011
CN    102317305 A    1/2012
(Continued)

OTHER PUBLICATIONS

Morphy et al. (J.Chem Scc CHem Commun 1989, 792-794 (Year: 1989).*
(Continued)

*Primary Examiner* — Karl J Puttlitz
(74) *Attorney, Agent, or Firm* — Winstead PC

(57) ABSTRACT

The present invention relates to protein drug conjugates, methods of manufacturing the same and their use in therapy. In particular, the present invention relates to protein drug conjugates comprising a globular protein, an improved linker and a drug for use in targeted drug delivery applications.

14 Claims, 37 Drawing Sheets

(51) Int. Cl.
  *A61K 47/64* (2017.01)
  *A61K 31/704* (2006.01)
  *A61K 47/54* (2017.01)
  *A61K 47/60* (2017.01)

(52) U.S. Cl.
  CPC ............ *A61K 47/545* (2017.08); *A61K 47/60* (2017.08); *A61K 47/64* (2017.08); *A61K 47/643* (2017.08); *A61K 47/6803* (2017.08); *A61K 47/6855* (2017.08); *A61K 47/6889* (2017.08)

(56) References Cited

U.S. PATENT DOCUMENTS

| 7,994,135 | B2* | 8/2011 | Doronina | C07K 7/02 514/19.3 |
|---|---|---|---|---|
| 8,609,105 | B2 | 12/2013 | Senter et al. | |
| 2001/0044526 | A1 | 11/2001 | Shen | |
| 2004/0116649 | A1 | 6/2004 | Kozlowski | |

FOREIGN PATENT DOCUMENTS

| EP | 0120694 | A2 | 10/1984 |
|---|---|---|---|
| EP | 0125023 | A1 | 11/1984 |
| EP | 0184187 | A2 | 6/1986 |
| EP | 0239400 | A2 | 9/1987 |
| EP | 0298101 | A1 | 1/1989 |
| GB | 2188638 | A | 10/1987 |
| JP | H07-078082 | B2 | 8/1995 |
| WO | WO-8705030 | A1 | 8/1987 |
| WO | WO-8805433 | A1 | 7/1988 |
| WO | WO-9216221 | A1 | 10/1992 |
| WO | WO-1993011161 | A1 | 6/1993 |
| WO | WO-1994013804 | A1 | 6/1994 |
| WO | WO-9741897 | A1 | 11/1997 |
| WO | WO-03061577 | A2 | 7/2003 |
| WO | WO-2006034488 | A2 | 3/2006 |
| WO | WO-2010009124 | A2 | 1/2010 |
| WO | WO2010070300 | * | 6/2010 |
| WO | WO-2010070300 | A2 | 6/2010 |
| WO | WO-2012076822 | A1 | 6/2012 |
| WO | WO-2012112687 | A1 | 8/2012 |
| WO | WO-2014064423 | A1 | 5/2014 |

OTHER PUBLICATIONS

Chemical Abstracts Registry No. 1350456-58-4, mal-peg-mc-vc-PAB-MMAE, entered: Dec. 8, 2011 (Year: 2011).*

Chemical Abstracts Registry No. 646502-53-6, mal-mc-vc-PAB-MMAE, entered: Feb. 5, 2004 (Year: 2004).*

Birikaki, Lemonia, "International Search Report," as prepared for PCT/GB2015/053227, dated Jan. 14, 2016, four pages.

Huston, James S., et al., "Protein Engineering fo Antibody Binding Sites: Recovery of Specific Activity in an Anti-Digoxin Single-Chain Fv Analogue produced in *Escherichia Coli*," Proc. Natl. Acad. Sci. USA, vol. 85, pp. 5879-5883, Aug. 1988.

Holliger, Philipp, et al., "Diabodies: Small Bivalent and Bispecific Antibody Fragments," Proc. Natl. Acad. Sci. USA, vol. 90, pp. 6444-6448, Jul. 1993.

Hu, Shi-zhen, et al., "Minibody: A Novel Engineered Anti-Carcinoembryonic Antigen Antibody Fragment (Single-Chain Fv-$C_H3$) Which Exhibits Rapid, High-Level Targeting of Xenografts' ", Cancer Research 56, pp. 3055-3061, Jul. 1, 1996.

Morphy, J. Richard., et al., "Towards Tumour Targeting With Copper-Radiolabelled Macrocycle-Antibody Conjugates: Synthesis, Antibody Linkage, and Complexation Behaviour," Journal of the Chemical Society, Perkin Transactions 2: Physical Organic Chemistry, No. 4, Jan. 1, 1990, pp. 573-585.

Ducry, Laurent, "Antibody-Drug Conjugates", Methods in Molecular Biology, vol. 1045, 2013, published by Humana Press.

Ward, E.Sally, et al., "Binding activities of a repertoire of single immunoglobulin variable domains secreted from *Escherichia coil*", Nature, vol. 341, Oct. 12, 1989, pp. 544-546.

Bird, et al., "Single-Chain Antigen-Binding Proteins", Science, vol. 242, Oct. 21, 1988, pp. 423-426.

Reiter, Yoram, et al., "Engineering antibody Fv fragments for cancer detection and therapy: Disulfide-stabilized Fv fragments", Nature Biotechnology, vol. 14, Oct. 1996, pp. 1239-1245.

Kratz, Felix; "Albumin as a drug carrier: Design of prodrugs, drug conjugates and nanoparticles"; Journal of Controlled Release 132 (2008); May 17, 2008; pp. 171-183.

Lambert, John M.; "Drug-conjugated antibodies for the treatment of cancer"; British Journal of Clinical Pharmacology 76(2); Nov. 23, 2012; pp. 248-262.

Inokuma, S. et al., "Synthesis and Complexing Properties of [2,n](2,6)Pyridinocrownophanes", J. Org. Chem., 70: 1698-1703 (2005).

Inokuma, S. et al., "Synthesis of crownophanes possessing bipyridine moieties: bipyridinocrownophanes exhibiting perfect extractability toward AG + ion", Tetrahedron, 62: 10005-10010 (2006).

Inokuma, S. et al., "Synthesis of crownophanes possessing three pyridine rings", Tetrahedron, 63: 5088-5094 (2007).

Benmansour, K. et al., "Ionic conductivity of poly[N-(3,6,9-trioxadecyl)-4-vinylpyridinium)] salts with univalent counter-ions in aqueous solutions", European Polymer Journal, 3(; 1443-1449 (2003).

Gauthier, M. et al., "Peptide/protein-polymer conjugates: synthetic strategies and design concepts", Chem. Commun., 2591-2611 (2008).

Roberts, M.J. et al., "Chemistry for peptide and protein PEGylation", Advanced Drug Delivery Reviews, 54: 459-476 (2002).

Morpurgo, M. et al., "Preparation and Characterization of Poly(ethylene glycol) Vinyl Sulfone", Bioconjugate Chem., 7: 363-368 (1996).

Crankshaw, M.W. et al., "Modification of Cysteine", Current Protocols in Protein Science, Unit 15.1, pp. 1-18 (1996).

* cited by examiner pH 7 Asp Challenge Exp. Time = ZERO    pH 7 Challenge Exp. after 18hrs incubation PL13-val-cit-PAB-MMAE Chemical Formula: $C_{69}H_{105}N_{11}O_{13}$
Molecular Weight: 1296.66
Elemental Analysis: C, 63.91; H, 8.16; N, 11.88; O, 16.04

| Peak ID | Area | % Peak | % L o H | Area Sum | Chain Fraction | Drug/Chain | Drug Count | Drug/H_L | DAR |
|---|---|---|---|---|---|---|---|---|---|
| L0 | 34803.00 | 23.04 | 34.55 | 52203.00 | 0.67 | 0.00 | 0.00 | 0.33 | |
| L1 | 17400.00 | 11.52 | | | 0.33 | 1.00 | 0.33 | | |
| H0 | 22753.00 | 15.06 | 65.45 | 98870.00 | 0.23 | 0.00 | 0.00 | 1.18 | |
| H1 | 40153.00 | 26.58 | | | 0.41 | 1.00 | 0.41 | | |
| H2 | 31133.00 | 20.61 | | | 0.31 | 2.00 | 0.63 | | |
| H3 | 4831.00 | 3.20 | | | 0.05 | 3.00 | 0.15 | | |
| Sum | 151073.00 | | | na | na | na | na | 1.52 | 3.03 |

Chemical Formula: $C_{26}H_{37}N_3O_9$
Molecular Weight: 535.59
Elemental Analysis: C, 58.31; H, 6.96; N, 7.85; O, 26.88

PL13-NH-PEG4-val-cit-PAB-MMAE

Chemical Formula: $C_{80}H_{126}N_{12}O_{18}$
Molecular Weight: 1543.95
Elemental Analysis: C, 62.24; H, 8.23; N, 10.89; O, 18.65

| Herceptin-PL13-PEG4-vc-cit-MMAE | | | | | | |
|---|---|---|---|---|---|---|
| Peak ID | Area | Area Sum | Chain Fraction | Drug/Chain | Drug Count | Drug/H_L | DAR |
| L0 | 21.03 | | 0.62 | 0.00 | 0.00 | | |
| L1 | 13.10 | 34.40 | 0.38 | 1.00 | 0.38 | 0.38 | |
| H0 | 8.60 | | 0.13 | 0.00 | 0.00 | | |
| H1 | 22.92 | | 0.35 | 1.00 | 0.35 | | |
| H2 | 25.43 | | 0.39 | 2.00 | 0.78 | | |
| H3 | 8.66 | | 0.13 | 3.00 | 0.40 | | |
| H4 | 0.00 | 65.61 | 0.00 | 4.00 | 0.00 | 1.52 | |
| Sum | 100.01 | na | na | na | na | 1.90 | 3.80 |

| Herceptin-mal-vc-cit-MMAE | | | | | | |
|---|---|---|---|---|---|---|
| Peak ID | Area | Area Sum | Chain Fraction | Drug/Chain | Drug Count | Drug/H_L | DAR |
| L0 | 12.10 | | 0.38 | 0.00 | 0.00 | | |
| L1 | 19.50 | 31.60 | 0.62 | 1.00 | 0.62 | 0.62 | |
| H0 | 7.80 | | 0.11 | 0.00 | 0.00 | | |
| H1 | 27.40 | | 0.40 | 1.00 | 0.40 | | |
| H2 | 21.80 | | 0.32 | 2.00 | 0.64 | | |
| H3 | 11.40 | | 0.17 | 3.00 | 0.50 | | |
| H4 | 0.00 | 68.40 | 0.00 | 4.00 | 0.00 | 1.54 | |
| Sum | 100.00 | na | na | na | na | 2.16 | 4.31 |

| Sample | Drug | SEC | | | | [P] mg/mL⁻¹ |
|---|---|---|---|---|---|---|
| | | HMW % | DIMER % | MONO % | LMW % | |
| Her.-mal-vc-cit-MMAE | Mal-vc-cit-MMAE | 1.6 | 0.8 | 96.5 | 1.1 | 4.96 |
| Her.-PL134-vc-cit-MMAE | PL13-PEG4-vc-cit-MMAE | 1.6 | 1.1 | 95.3 | 2.1 | 4.98 |

| DAR Species | Percentage | Average DAR |
|---|---|---|
| 0 | 4.52 | |
| 1 | 5.17 | |
| 2 | 20.9 | |
| 3 | 6.0 | |
| 4 | 39.95 | |
| 5 | 5.46 | |
| 6 | 13.16 | |
| 7 | 1.42 | |
| 8 | 3.28 | |
| Sum | 100.0 | 3.41 |

| DAR Species | Percentage | Average DAR |
|---|---|---|
| 0 | 3.97 | |
| 1 | 1.05 | |
| 2 | 24.83 | |
| 3 | 2.19 | |
| 4 | 46.97 | |
| 6 | 15.78 | |
| 8 | 5.21 | |
| Sum | 100.0 | 3.8 |

MATERIALS AND METHODS RELATING TO LINKERS FOR USE IN PROTEIN DRUG CONJUGATES

The present invention relates to protein drug conjugates, and methods of manufacturing the same. More especially, the present invention relates to providing a protein, linker and drug, for example a cytotoxin, to produce a protein drug conjugate. Additionally, the present invention provides an improved linker for use in protein drug conjugates and methods of introducing said linker into said protein drug conjugates. More specifically, the protein drug conjugate may be an antibody drug conjugate (ADC) or an albumin and linker containing drug conjugate.

Protein drug conjugates, in particular antibody drug conjugates, are known to provide targeted delivery of highly potent drugs to specific tissue for treatment. More specifically, ADCs, which typically consist of an antibody linked via a chemical linker with labile bonds, to a biologically active cytotoxic or drug payload, are known for use in anticancer treatments. The targeted delivery offered by such protein drug conjugates results from the ability of the antibody or the like to sensitively discriminate between healthy and diseased tissue, thus ensuring safe delivery of the highly potent drug.

As such antibodies, especially monoclonal antibodies (mAbs) are useful in targeted research, therapeutic, diagnostic and other biotechnology uses. More especially, mAbs are useful in the area of targeted treatments and medicaments. mAbs can be utilised by way of incorporation into a treatment by means of an Antibody Drug Conjugate (ADC). As discussed above, ADCs are a type of bioactive medicament believed to have particular utility in the treatment of cancers, amongst other things, and are a relatively new technology. Generally, an ADC (for example) for treatment of a cancer will comprise a mAb linked to a cytotoxic payload or drug, which can provide a cell killing action. The connection between the mAb and the cytotoxic material (cytotoxin) will generally be provided by a chemically stable linker molecule. Two types of ADC linker systems are known in the art; cleavable and non-cleavable. For cleavable ADC linker systems there is a release mechanism which is preferably enzymatically driven, although alternative cleavable systems are known which are chemically labile, as detailed in Methods in Molecular Biology, Volume 1045, 2013, published by Humana Press. In non cleavable ADC linker systems the release route is due to mAb degradation by the machinery of the cell when the ADC is in use.

The market approval in Europe and the US of the ADCs Adcetris® (Seattle Genetics/Takeda Group) and Kadcyla® (Genentech/Roche) has paved the way for increased research into this ADC class of biotherapeutics.

Adcetris®, shown below (also known as brentuximab vedotin), is directed to the protein CD30, which is expressed in classical Hodgkin lymphoma (HL) and systemic anaplastic large cell lymphoma (sALCL). Brentuximab vedotin consists of the chimeric monoclonal antibody brentuximab (cAC10, which targets the cell-membrane protein CD30) linked to a cathepsin cleavable linker (valine-citrulline), para-aminobenzylcarbamate spacer and the antimitotic agent monomethyl auristatin E (MMAE).

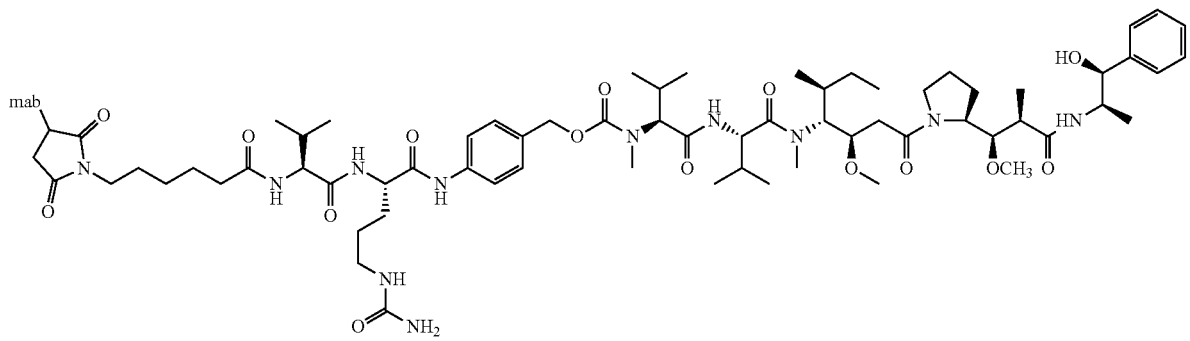

Kadcyla®, shown below, is trastuzumab emtansine, an ADC consisting of the monoclonal antibody trastuzumab (Trastuzumab) linked to the cytotoxic agent mertansine (DM1). Trastuzumab alone stops growth of cancer cells by binding to the HER2/neu receptor, whereas mertansine enters cells and prevents cell division by binding to tubulin; ultimately this binding action will result in cell apoptosis. The conjugate is typically abbreviated to T-DM1. Each molecule of trastuzumab emtansine consists of a single trastuzumab molecule bound to several molecules of mertansine, a cytotoxic maytansinoid containing a sulfhydryl group, through a crosslinking reagent known as SMCC. SMCC is succinimidyl trans-4-(maleimidylmethyl) cyclohexane-1-carboxylate, a bi-functional cross linker, that contains two reactive functional groups, a succinimide ester and a maleimide. The succinimide group of SMCC reacts with the free amino group of a lysine residue in the trastuzumab molecule and the maleimide moiety of SMCC links to the free sulfhydryl group of mertansine, forming a covalent bond between the antibody and mertansine.

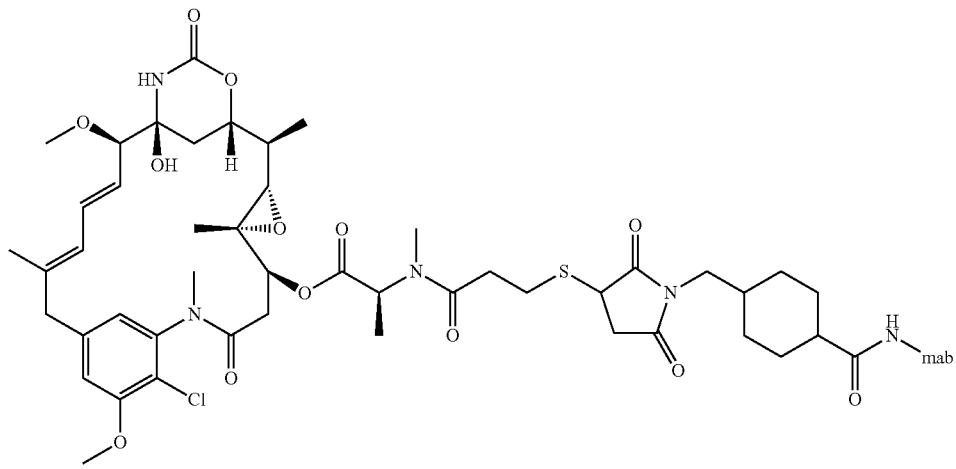

While ADCs are well-known in the art, other protein drug conjugates comprising a globular protein with the ability to provide targeted delivery of a drug payload are not as well-known. For example, albumin may offer a suitable alternative to antibodies in such protein drug conjugates.

Albumin consists of three structurally homologous, largely helical domains (I, II and III, each consisting of two subdomains, A and B. Like other mammalian albumins, human albumin contains 17 disulfide bridges and a free thiol at Cys34, which provides the largest fraction of free thiol in blood serum.

Albumin is the major protein responsible for the colloid osmotic pressure of the blood and functions as a transport vehicle for long chain fatty acids, bilirubin, metal ions such as copper (II) and nickel (II), calcium and zinc. Albumin has an approximate serum half-life of 20 days, attributable to the size of the protein (approx. 67 kDa) and also a consequence of recycling through neonatal Fc receptors (FcRn). The FcRn recycles albumin, as well as antibodies (more especially IgGs), in a pH-dependent non-competitive manner protecting both from protein degradation in the lysosome. Circulating albumin is internalised by endothelial cells where it binds to FcRn in the acidic environment of the early endosome (pH 6). This allows albumin to be recycled to the surface of the cell and released back into the blood (physiological pH). Albumin can be covalently conjugated to a cytotoxic drug or alternatively fused to a protein-based therapeutic in order to increase bio-availability and improve drug pharmacokinetics.

Solid tumours have a permeable vasculature and also poor lymphatic drainage which result in an accumulation and retention of macromolecules (>40 kDa) within the tumour interstitial fluid. Studies have demonstrated the retention of albumin in various malignant solid tumours. There is also emerging evidence for the specific binding of albumin by various receptors, some of which have been shown to be highly expressed on malignant cells. Similarly, albumin is known to accumulate in inflamed joints of rheumatoid arthritis patients due to an increase in the permeability of the blood-joint barrier. A known application of albumin in drug delivery is liver targeting using albumin conjugates containing galactose residues, which enter hepatocytes after interaction with the asialoglycoprotein receptor (ASGP-R), present in large amounts and high affinity only on these cells.

Accordingly, these targeting properties, as well as its availability, biodegradability, lack of toxicity and immunogenicity and aligned with its markedly long half-life, make albumin a suitable candidate for drug delivery. As such, albumin represents a suitable alternative to antibodies in protein drug conjugate systems.

The successful delivery of a drug or cytotoxic payload to the target tissue is dependent upon the ability of the linker to bind to the protein and drug and to remain bound until the protein drug conjugate reaches the target tissue. Accordingly, there exists a need to provide alternative and/or improved linkers for use in such protein drug conjugates which provide successful delivery.

Additionally, there exists a need to provide new and/or improved protein drug conjugates, such as those comprising albumin, for safe and effective delivery of cytotoxic drugs or therapeutic peptides or polypeptides.

In one embodiment, there exists a need to provide alternative and improved ADCs, which can effectively provide cell apoptosis properties. More especially, there is a need to provide improved ADC linker molecules to ensure selective and effective conjugation during the manufacture of said ADCs, and provide effective cytotoxin payload when in use.

Accordingly, in a first aspect of the present invention, there is provided a protein drug conjugate comprising a globular protein, a linker and a drug. More specifically, the present invention provides a protein drug conjugate comprising a linker capable of providing site specific conjugation via a lysine or cysteine group present on the protein, preferably a nitrogen containing heterocyclic aromatic ring comprising a vinyl substituent.

The present invention provides a linker for use in protein drug conjugates, with utility in linking proteins and drugs, for example antibodies and cytotoxins to provide ADC molecules. The linker provides an improved targeted payload of the drug. Additionally or alternatively, the linker provides the protein drug conjugate with increased stability as compared to currently known linker molecules for use in ADCs, thus affording protein drug conjugates with improved safety properties and consequently enhanced tolerability profiles. More specifically, use of the presently disclosed linker molecule in ADCs provides increased potency of the ADC, when in use, over and above the equivalent unconjugated antibody.

In the context of the present invention, the term "globular protein" should be construed to cover any protein which has targeting capabilities and so has the ability to deliver a drug payload to a specific target tissue. Accordingly, "globular proteins" include antibodies and fragments thereof, albumin and transferrin, as well as any other alternatives known for use in drug conjugates.

By "drug" it is meant any chemical substance which has a known biological effect on humans or animals. In particular, the drug may be a pharmaceutical drug which is used in the treatment, cure, prevention or diagnosis of disease or to otherwise enhance physical or mental well-being. As will be appreciated, the drug may be a known drug which has obtained the necessary marketing authorisation or a novel drug which has not yet undergone testing or achieved marketing authorisation.

In one embodiment of the present invention, there is provided an antibody drug conjugate comprising an antibody, a linker and a cytotoxin.

Preferably the antibody is an antibody, or fragment thereof, and more preferably a monoclonal antibody (mAb). The mAb can be selected from any known mAb. The only limitation on the selection of the mAb for use in the present invention is that it must have a cysteine or lysine residue present to allow the conjugation reaction to take place. It is particularly preferred that the mAb contain a cysteine residue, as some especially preferred embodiments of the linker of the present invention show increased selectivity toward the thiol group present in the cysteine residue. However, in the case that a mAb is identified which does not ordinarily contain the preferred cysteine residue, methods are known to the skilled person in the art to introduce cysteine in to mAbs.

According to an alternative embodiment of the present invention (as further detailed below), the antibody may be substituted for albumin.

All of the preferred embodiments discussed below, which may or may not be described in relation to the antibody containing ADCs or albumin drug conjugates, can be equally considered as preferred embodiments for the protein drug conjugate, as well as the ADC embodiment and the albumin drug conjugate embodiment. More especially, the description of the drug and linker below, should be considered to apply equally to the various embodiments of the protein drug conjugates.

The drug may be a cytotoxic payload or a therapeutic peptide or polypeptide. In particular, where the protein is an antibody or a fragment thereof and the protein drug conjugate is an ADC, the drug is preferably a cytotoxin. Alternatively, where the protein is albumin, the drug may be a cytotoxin or a therapeutic peptide or polypeptide.

Preferably the cytotoxin is a biologically active cytotoxic material. Most preferably the cytotoxin is an anticancer drug. The cytotoxin may be selected from the group comprising auristatins, maytansines, calicheamicin, anthracycline and the pyrrolobenzodiazepenes. More especially, the cytotoxin may be monomethyl auristatin E (MMAE), doxorubicin or mertansine (DM1). It should be apparent to the person skilled in the art that MMAE is also known as (S)—N-((3R,4S,5S)-1-((S)-2-(((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)-N,3-dimethyl-2-((S)-3-methyl-2-(methylamino) butanamido)butanamide.

However, additionally or alternatively, the cytotoxin could also be selected from other known cytotoxins including ricin subunits and other peptide based cytotoxic materials, although such materials are less commonly utilised in the field of the art.

Where the drug is a therapeutic peptide or polypetide, the peptide or polypeptide may be any peptide or polypeptide which has therapeutic properties, for example antinociceptive, antidiabetes, antitumor or antiviral activity.

Additionally, or alternatively, the drug preferably comprises an amine group, a thiol group, or a carboxylic acid group, as these types of groups provide ideal sites for conjugation of the drug with the linker of the present invention.

Preferably the linker (also referred to herein as the linker molecule or linker group) provides site specific conjugation via the lysine or cysteine group present on the protein, such as an antibody.

More preferably the linker of the present invention comprises a nitrogen containing heterocyclic aromatic ring comprising a vinyl substituent.

In very general terms, the linker can be considered to comprise of three parts; a vinyl group, a nitrogen containing heterocyclic aromatic ring, and a linker arm. The linker arm can be varied to result in differing terminal groups to provide reaction sites for either the drug or protein, for example the antibody of an ADC, to bind to the linker.

Preferably, the nitrogen containing heterocyclic aromatic ring is a pyridine, pyrimidine, imidazole or aziridine ring. More preferably, the nitrogen containing heterocyclic aromatic ring is a pyridine ring or a pyrimidine ring and most preferably, it is a pyridine ring. When pyridine or pyrimidine rings are employed, preferably the vinyl group is in the 2-position or 4-position relative to a nitrogen heteroatom. 4-vinylpyridines are particularly preferred as they have been found to provide commercially acceptable rates of reaction in certain circumstances, as discussed further below.

Examples of the preferred linkers in accordance with the present invention include:

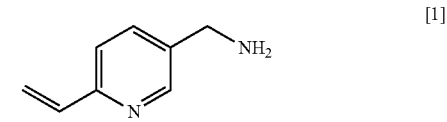

[1]

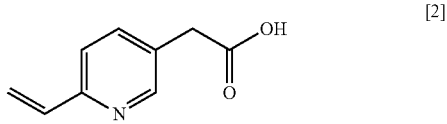

[2]

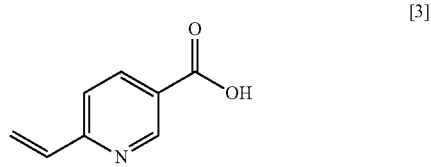

[3]

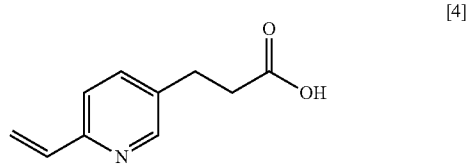

[4]

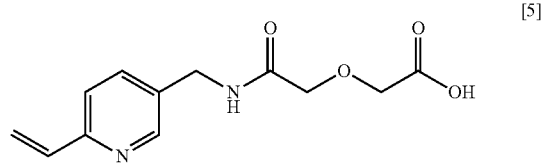

[5]

[6] 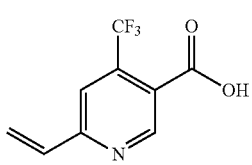

[7] 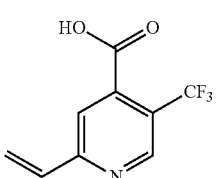

[8] 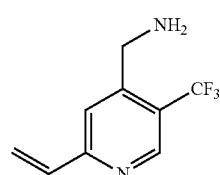

[9] 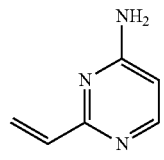

[10] 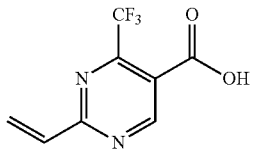

[11] 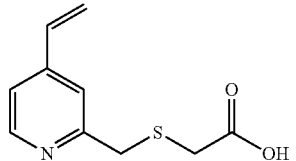

[12] 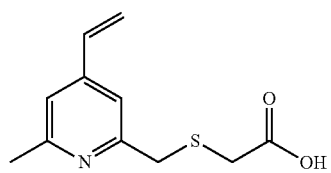

[13] 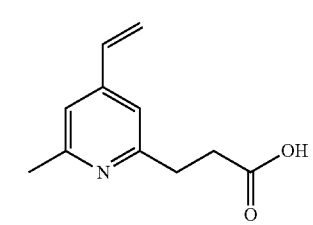

[14] 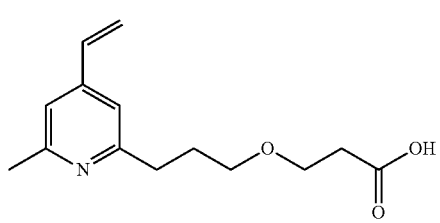

[15] 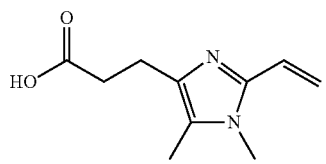

[16] 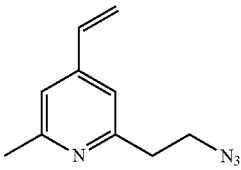

[17] 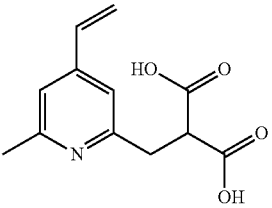

[18] 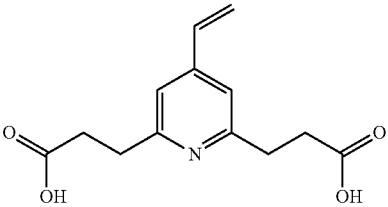

Of the examples shown above, the 4-vinylpyridine structures are particularly preferred, and the structure shown as [13] is most especially preferred. 4-Vinylpyridine structures are preferred, as in certain conditions, they show an increased reactivity over and above equivalent 2-vinylpyridine structures.

As will be appreciated by the skilled person, each of the structures exemplified above are provided predominately with a terminal carboxylic acid group on the linker arm. However, these structures may preferably be provided in a substituted form, such that the preferred vinylpyridine structure comprises a preferred poly-(alkylene glycol) group, most preferably a PEG molecule. The presence of a PEG group on the linker molecule arm has been found to be most preferable as it enhances reaction efficiency when seeking to obtain the required drug to protein ratio in the protein drug conjugate methods of manufacture.

Such preferred linker molecules include the following examples:

PL1 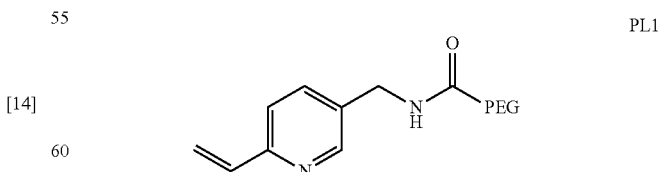

PL2 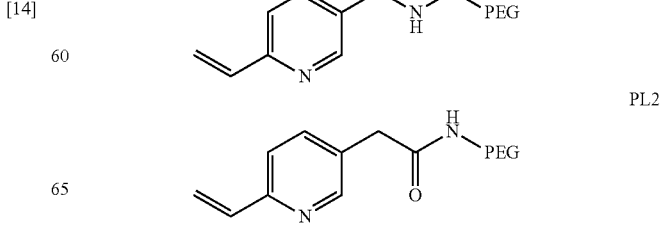

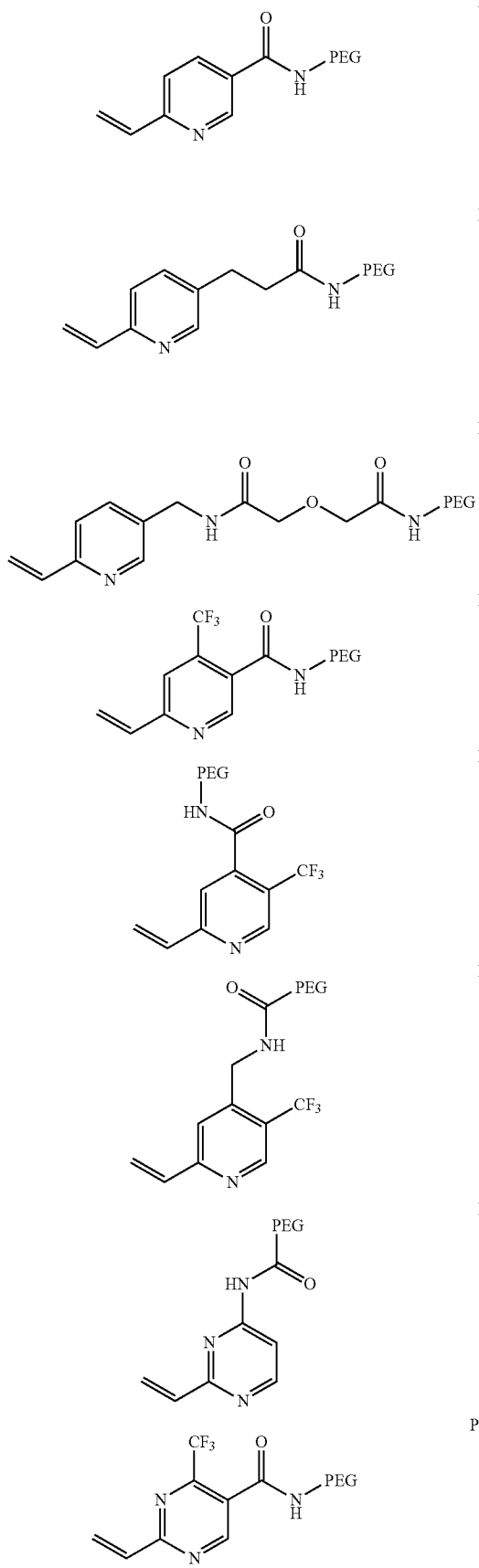
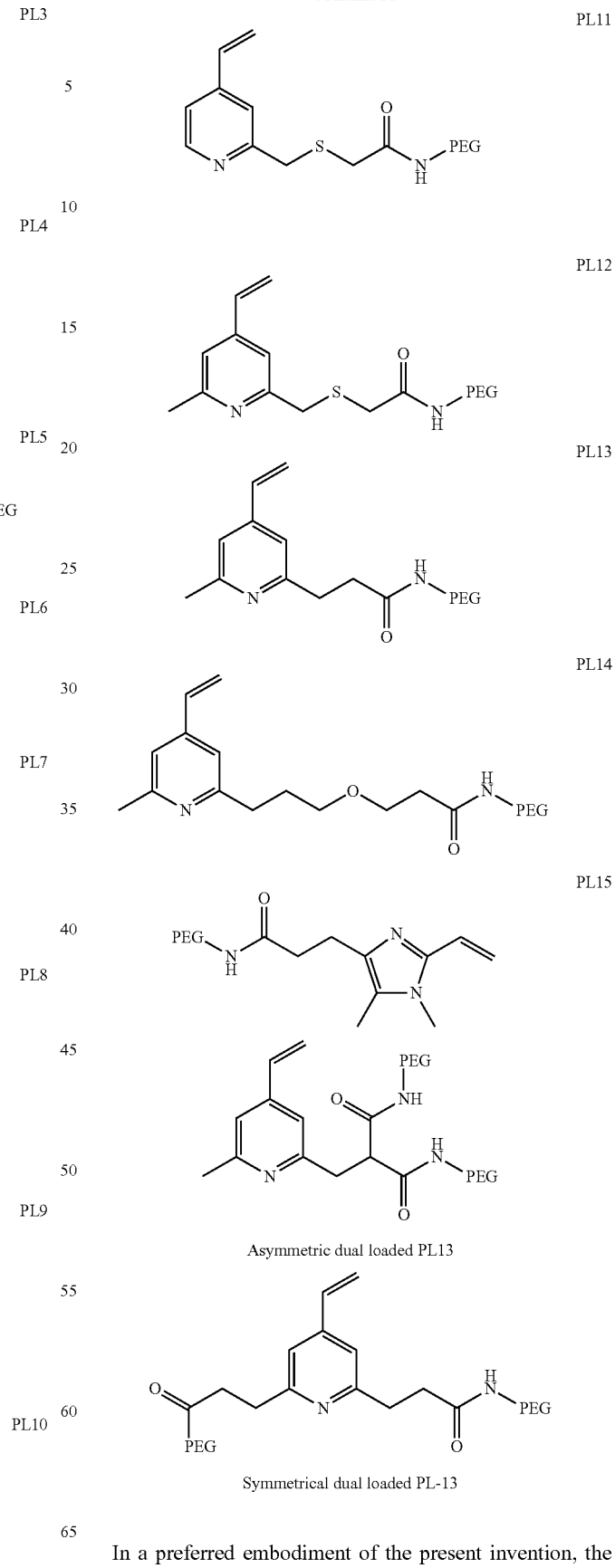
Asymmetric dual loaded PL13
Symmetrical dual loaded PL-13
In a preferred embodiment of the present invention, the linker comprises a molecule having the general formula:

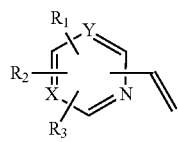 (I)

wherein:
X and Y are independently selected from CH or N.
$R_1$ is selected from;
  $(CH_2)_n$—C(O)—R, or,
  $(CH_2)_m$—Z—R, or,
  $(CH_2)_m$—Z—C(O)—R, or,
  $(CH_2)_n$—C(O)—Z—R, or,
  $(CH_2)_m$—Z—$(CH_2)_n$—C(O)—R, or,
  $(CH_2)_m$—Z—$(CH_2)_n$—C(O)—Z—R, or,
  $(CH_2)_m$—Z—C(O)—$(CH_2)_n$—Z—$(CH_2)_n$—C(O)—Z—R, or
  $(CH_2)_n$—CH$(CO_2R)_2$, or
  $(CH_2)_m$—Z—$(CH_2)_2$CH$(CO_2R)_2$, or
  $(CH_2)_n$—$Z_1$.

$R_2$ and/or $R_3$ may be selected from the same group of molecules as $R_1$. However, preferably $R_2$ and/or $R_3$ are selected from hydrogen or an electron withdrawing group, such as halogen (F, Cl, or Br), —$NO_2$, —$CO_2H$, —$CO_2R_4$, $COR_4$, —CHO, —CN, —$CF_3$, —$SO_2NR_4R_5$ where $R_4$ and $R_5$ are independently selected from hydrogen or $C_{1-10}$ alkyl; or, $R_2$ and/or $R_3$ may be selected from hydrogen, alkyl or phenyl, this is particularly preferred when the linker molecule comprises a pyridine ring, as the alternative electron withdrawing groups may have a negative effect on the reactivity of the linker; or $R_2$ and $R_3$ together form a fused (hetero) aromatic ring substituent which may include, but is not limited to, an indole, indazole, benzimidazole, quinoline, isoquinoline, aziridine or a purine.

When $R_2$ and/or $R_3$ is selected to be from an alkyl group, a methyl group ($CH_3$), or a tert-butyl (($CH_3)_3C$) is preferred. The presence of an alkyl group on the linker molecule is preferred as the presence of such a group increases the basicity of the nitrogen present in the ring structure and results in the linker structure having increased reactivity over and above equivalent linker molecules.

When $R_2$ and/or $R_3$ is selected from an electron withdrawing group, $CF_3$ is preferred. The presence of $CF_3$ increases the reactivity of the vinyl group present in the linker molecule, and is stable under physiological conditions.

Alternatively, it is contemplated that in some embodiments, it is possible to employ more extended fused heterocyclic aromatic ring systems such as an indole, indazole, benzimidazole, quinoline, isoquinoline, aziridine or a purine.

In the formulas given above,
Z can be independently selected from NH, O, or S,
$Z_1$ is an $N_3$ group or an OH group
n can be any integer from 0 to 10. In some preferred embodiments n is a value from 0 and 5.
m can be any integer from 0 and 10. Preferably m is from 0 and 5, and most preferably m is from 0 and 3, as shown in the examples given above. Additionally, or alternatively, in linker molecules where the Z group following the $(CH_2)$, group is an O group and $R_1$ (and $R_2$ and/or $R_3$ where they are selected from the same group of molecules) is in the 2 or 6 position on the ring structure, then m is preferably at least 3, as the O group should be spaced from nitrogen of the ring structure. This is due to the reducing effect that the oxygen group has been found to have on the reactivity of the linker molecule structures. This effect is not felt when the oxygen group is further spaced from the ring structure. This situation is reflected in the exemplified structures above.

R may be a hydrogen (H), hydroxide (OH), amine or a poly-(alkylene glycol) group. Preferably R is a poly-(alkylene glycol), and most preferably it is a PEG. As will be appreciated by the skilled person, when the R group is PEG, it may preferably be proceeded by a Z group in the form of NH, due to the reaction product of addition of the PEG. This option is detailed in the generic formulae of $R_1$ given above. Generally, the poly-(alkylene glycol) molecule is directly covalently bonded to the $R_1$ and/or $R_2$ groups as shown in the formula above. The linker group arms may have different lengths to keep the poly-(alkylene glycol) molecule closer or further away from the protein, for example the antibody.

Preferably the drug, such as a cytotoxic, is bound to the linker $R_1$ group. In cases where $R_2$ and/or $R_3$ are selected from the same group of molecules as $R_1$, as described above, then it is possible that these groups will also bind to drugs, such as cytotoxins, to provide protein drug conjugate, such as ADCs, with multiple drugs present in their structures. Some embodiments of this type may be referred to as symmetrical loading of the drug in the protein drug conjugate.

Additionally or alternatively, where $R_1$, and optionally $R_2$ and/or $R_3$, are selected from $(CH_2)_n$—CH$(CO_2R)_2$, or $(CH_2)_m$—Z—$(CH_2)_2$CH$(CO_2R)_2$, i.e. where the linker arm is branched, then it is possible that the drugs bind to each terminating group of the linker arm. As such multiple drugs are present in the protein drug conjugate and may be described as asymmetrical loading of the drug.

Preferably, the nitrogen containing heterocyclic aromatic ring is a substituted pyridine ring (X and Y are both CH) or a substituted pyrimidine ring (one of X and Y is CH and the other is N). Most preferably the nitrogen containing heterocyclic aromatic ring is a pyridine ring.

In one particularly preferred embodiment $R_1$ is either;
$(CH_2)_n$—C(O)—R, or,
$(CH_2)_n$—C(O)—Z—R, or,
$(CH_2)_m$—Z—$(CH_2)_n$—C(O)—R, or
$(CH_2)_m$—Z—$(CH_2)_n$—C(O)—Z—R.

In a further embodiment of the present invention, it might be desirable to include an extender linker within the linker molecule described above. Such an extender linker may be necessary to alter solubility or immunogenic properties of the functionalising group. More especially such an extender linker will be useful in a cleavable ADC linker system, which will be described in more detail below. Suitable extender linkers for utilisation in the present invention will be apparent to the skilled person in the art, and particularly preferred extender linkers are described in U.S. Pat. Nos. 7,659,241 and 5,609,105. Most preferably the extender linker is an enzyme cleavable extender linker that comprises a collection of amino acids that can be cleaved by an intracellular protease.

In a further embodiment of the present invention it might be desirable to provide the linker in a modified form, such that it comprises an ester group to facilitate binding of the linker to the protein of the protein drug conjugate. This aspect will be described further below.

Preferred linkers in accordance with the present invention may be represented by the following formulae,

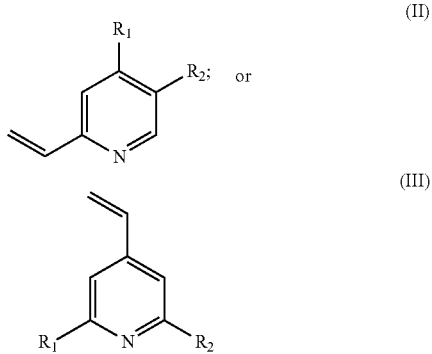

wherein:
R$_1$ is selected from;
$(CH_2)_n$—C(O)—R, or
$(CH_2)_m$—Z—R, or
$(CH_2)_m$—Z—C(O)—R, or
$(CH_2)_n$—C(O)—Z—R, or
$(CH_2)_m$—Z—$(CH_2)_n$—C(O)—R, or
$(CH_2)_m$—Z—$(CH_2)_n$—C(O)—Z—R, or
$(CH_2)_m$—Z—C(O)—$(CH_2)_n$—Z—$(CH_2)_n$—C(O)—Z—R, or
$(CH_2)_n$—CH(CO$_2$R)$_2$, or
$(CH_2)_m$—Z—(CH$_2$)$_2$CH(CO$_2$R)$_2$, or
$(CH_2)_n$—Z$_1$ R$_2$ may be selected from the same group of molecules as R$_1$. However, preferably R$_2$ is selected from hydrogen or an electron withdrawing group, such as halogen (F, Cl, or Br), —NO$_2$, —CO$_2$H, —CO$_2$R$_4$, COR$_4$, —CHO, —CN, —CF$_3$, —SO$_2$NR$_4$R$_5$ where R$_4$ and R$_5$ are independently selected from hydrogen or C$_{1-10}$ alkyl; or, R$_2$ may be selected from hydrogen, alkyl or phenyl, this is particularly preferred as the alternative electron withdrawing groups may have a negative effect on the reactivity of the linker.

When R$_2$ is selected to be from an alkyl group, a methyl group (CH$_3$), or a tert-butyl ((CH$_3$)$_3$C) is preferred. The presence of an alkyl group on the linker molecule is preferred as the presence of such a group increases the basicity of the nitrogen present in the ring structure and results in the linker structure having increased reactivity over and above equivalent linker molecules.

When R$_2$ is selected from an electron withdrawing group, CF$_3$ is preferred. The presence of CF$_3$ increases the reactivity of the vinyl group present in the linker molecule, and is stable under physiological conditions.

In the formulas given above,
Z can be independently selected from NH, O, or S,
Z$_1$ is independently selected from N$_3$ or OH,
n can be any integer from 0 to 10. In some preferred embodiments n is a value from 0 and 5,
m can be any integer from 0 and 10. Preferably m is from 0 and 5, and most preferably m is from 0 and 3, as shown in the examples given above. Additionally, or alternatively, in linker molecules of formula (III) where the Z group following the (CH$_2$), group is an O group, then m is preferably at least 3, as the O group should be spaced from the nitrogen of the ring structure. This is due to the reducing effect that the oxygen group has been found to have on the reactivity of the linker molecule structures. This effect is not felt when the oxygen group is further spaced from the ring structure. This situation is reflected in the exemplified structures above, R is a hydrogen (H), hydroxide (OH), amine or a poly-(alkylene glycol) group. Preferably R is a poly-(alkylene glycol), and most preferably it is a PEG. As will be appreciated by the skilled person, when the R group is PEG, it may preferably be proceeded by a Z group in the form of NH, due to the reaction product of addition of the PEG. This option is detailed in the generic formulae of R$_1$ given above. Generally, the poly-(alkylene glycol) molecule is directly covalently bonded to the R$_1$ and/or R$_2$ groups as shown in the formula above. The linker group arm may have different lengths to keep the poly-(alkylene glycol) molecule closer or further away from the protein, for example the antibody.

Preferably the drug, for example a cytotoxic, is bound to the linker R$_1$ group. In cases where R$_2$ is selected from the same group of molecules as R$_1$, as described above, then it is possible that these groups will also bind to drugs, e.g. cytotoxins, to provide protein drug conjugates, e.g. ADCs, with multiple drugs present in their structures. Some embodiments of this type may be referred to as symmetrical loading of the drug in the protein drug conjugate.

Additionally or alternatively, where R$_1$, and optionally R$_2$, are selected from (CH$_2$)$_n$—CH(CO$_2$R)$_2$, or (CH$_2$)$_m$—Z—(CH$_2$)$_2$CH(CO$_2$R)$_2$, i.e. where the linker arm is branched, then it is possible that the drugs bind to each terminating group of the linker arm. As such multiple drugs are present in the protein drug conjugate and may be described as asymmetrical loading of the drug.

In one embodiment of the present invention, the linker is represented by the formula (III).

Additionally, or alternatively, where a poly(alkylene glycol) group is present, the basic poly-(alkylene glycol) structure may be provided with one or more reactive functional groups such as hydroxy, amine, carboxylic acid, alkyl halide, azide, succinimidyl, or thiol groups to facilitate the reaction of the poly-(alkylene glycol) molecule with the drug or protein. Particularly preferred poly-(alkylene glycol) molecules include those substituted at one or more hydroxyl positions with a chemical group, such as an alkyl group having between one and four carbon atoms. The most preferred poly-(alkylene glycol) molecules for use in accordance with the present invention are polyethylene glycol ("PEG") molecules, as mentioned above, although the skilled person would be able to use the techniques disclosed herein in conjunction with other poly-(alkylene glycol) molecules, such as polypropylene glycol or polyethylene-polypropylene glycol copolymers. Poly-(alkylene glycol) molecules, including PEGs, typically have molecular weights between about 200 Da and about 80 kDa. Preferred poly-(alkylene glycol) molecules have molecular weights between about 200 Da and 1 kDa. Poly-(alkylene glycol) molecules that may be used in accordance with the present invention are well known in the art and publicly available, for example from commercially available sources such as Sigma Aldrich.

In a further aspect of the present invention there is provided non-cleavable and/or cleavable protein drug conjugate (e.g. ADC) linker systems.

A non-cleavable protein drug conjugate (e.g. ADC) linker system may be provided, which comprises a protein (e.g. an antibody), a linker, and a drug (e.g. a cytotoxin). In one system of this type, conjugation of an amine group on the antibody is achieved via an activated ester present on the linker, which then in turn binds to the cytotoxin via the vinyl group. In this non-cleavable system the antibody is preferably a mAb. Additionally, the linker preferably comprises a poly-(alkylene glycol) molecule, most preferably a polyethylene glycol (PEG) molecule and the cytotoxic contains a thiol. As will be appreciated, in the above described system, the antibody is provided as an example of a protein and may be substituted for albumin and the cytotoxin is provided as an example of a drug and may be substituted for a therapeutic peptide or polypeptide.

In an alternative system of this type, conjugation of a thiol group on the antibody is achieved via the vinyl group of the linker, which in turn binds to a drug via a poly(alkylene glycol) group present on the linker arm.

In an alternative embodiment, there is provided a cleavable protein drug conjugate (e.g. ADC) linker system, which comprises a protein (e.g. an antibody), linker, extender linker and a drug (e.g. a cytotoxin).

In a cleavable ADC linker system, the vinyl substituent of the linker molecule is especially suited to reacting with one or more thiol groups that are naturally present, or have been introduced into, the antibody (for example by employing a thiol group of one or more cysteine residues present on the antibody). The linker side-arm is then connected to the extender linker, preferably via the poly-(alkylene glycol) molecule; the extender linker provides the "cleavable" function to the ADC in this embodiment. The cytotoxin is then bound to the linker via the extender linker. Preferably, the antibody is a mAb. More preferably, the linker comprises a poly-(alkylene glycol) molecule, most preferably a polyethylene glycol (PEG) molecule. It is preferred that the extender linker is enzyme cleavable, as described in further detail above. As will be appreciated, in the above described system, the antibody is provided as an example of a protein and may be substituted for albumin and the cytotoxin is provided as an example of a drug and may be substituted for a therapeutic peptide or polypeptide.

It should be understood that in the present application the term "cleavable" is used to encompass protein drug conjugates (e.g. ADCs) which are able to self immolate or may be manipulated to release their drug (e.g. cytotoxic) payload. Use of the term is intended to distinguish such protein drug conjugates (e.g. ADCs) from those "non-cleavable" protein drug conjugates (e.g. ADCs) which are understood to only release their drug (e.g. cytotoxic) payload once present in a target cell.

It should be understood that the preferable features of the protein (e.g. antibody), linker and drug (e.g. cytotoxin) for utilising in this aspect of the invention are as described above in relation to the first aspect. More especially, the description of the linker molecule and its preferable features are particularly suited for use in said cleavable and non-cleavable systems.

Although it is preferred that the protein (e.g. antibody) utilised in the present invention comprise at least one or more thiol containing cysteine group, it is also contemplated that the protein (e.g. antibody) may contain one or more lysine group. When this is the case it is contemplated that the skilled person may prefer to attach the linker of the present invention to a lysine group as an alternative to a cysteine group. In this situation it is preferred to modify the linker molecule such that it is an activated ester form of the linker.

In this embodiment the ester group of the modified linker is able to bind to the lysine present on the protein (e.g. antibody) via the linker arm. In this embodiment, the protein (e.g. the antibody) will bind via a lysine group to the ester modified linker, and in turn this will bind to the drug (i.e. the cytotoxin) via the vinyl group. This modified linker may comprise a poly-(alkylene glycol) molecule, most preferably a polyethylene glycol (PEG) molecule.

In a third aspect of the present invention, there is provided a method of producing a protein drug conjugate which comprises contacting a protein with a linker capable of providing site specific conjugation via a lysine or cysteine group present on the protein, preferably comprising a nitrogen containing aromatic heterocyclic ring comprising a vinyl substituent, wherein the linker is bound to a drug. In an alternative aspect, there is provided a method of producing a protein drug conjugate which comprises contacting a protein with a linker capable of providing site specific conjugation via a lysine or cysteine group present on the protein, preferably comprising a nitrogen containing aromatic heterocyclic ring comprising a vinyl substituent, and subsequently binding the linker to a drug.

Preferably the method comprises contacting the protein (e.g. the antibody) having at least one reactive thiol group with the linker which comprises a functionalising reagent, comprising a nitrogen containing heterocyclic aromatic ring having a vinyl substituent capable of reacting with at least one thiol group of the protein (e.g. the antibody), wherein the linker functionalising reagent is covalently linked to a poly-(alkylene glycol) molecule, so that the vinyl substituent of the linker functionalising reagent reacts with the thiol group of the protein (e.g. the antibody), thereby to covalently link the linker poly-(alkylene glycol) molecule to the protein (e.g. the antibody).

In addition, the methods of the present invention may involve one or more steps in addition to the step of reacting the functionalising reagent and the protein (e.g. the antibody) to link them together. By way of example, the methods may include an initial step of reacting a precursor functionalising reagent comprising a nitrogen containing heterocyclic aromatic ring having a vinyl substituent with the poly-(alkylene glycol) molecule to produce the functionalising reagent.

In embodiments of the present invention in which the protein (e.g. the antibody) does not include a suitable thiol group, or does not include a suitable thiol group in a desired position in its polypeptide chain, the present invention may comprise the initial step of modifying the protein (e.g. the antibody), e.g. by chemical reaction or site directed mutagenesis, to produce a variant polypeptide having a thiol group at one or more desired positions of the polypeptide. Preferably, this is done by replacing one or more of the amino acids in the polypeptide chain of the protein (e.g. the antibody) with a cysteine residue.

Preferably, the reactive thiol group, whether it is present naturally in the protein (e.g. the antibody) or has been introduced, is part of a cysteine amino acid residue.

Additionally, or alternatively, the present invention provides albumin in combination with the linker, wherein the linker is as described above, in relation to the first embodiment of the present invention.

As will be appreciated, the albumin intended for use in the present invention is serum albumin, which is a blood plasma protein produced in the liver. Preferably the albumin is human albumin.

Preferably the linker comprises a poly-(alkylene glycol) molecule, most preferably a polyethylene glycol (PEG) molecule.

Additionally, or alternatively, the present invention provides a protein drug conjugate comprising albumin, a linker and a drug (e.g. a cytotoxin), wherein the linker and drug (e.g. cytotoxin) are as described above in relation to the protein drug conjugate and/or the ADC invention. In particular, it is preferable that the linker comprises a poly-(alkylene glycol) molecule, most preferably a polyethylene glycol (PEG) molecule, which binds to the drug (e.g. the cytotoxin).

The present invention also provides a protein drug conjugate comprising albumin, a linker and a therapeutic peptide or polypeptide. The linker and therapeutic peptide or polypeptide are as described above, and it is preferable that the linker comprises a poly-(alkylene glycol) molecule, most preferably a polyethylene glycol (PEG) molecule, which binds to the therapeutic peptide or polypeptide.

Additionally, or alternatively, as described above, the basic poly-(alkylene glycol) structure may be provided with one or more reactive functional groups such as hydroxy, amine, carboxylic acid, alkyl halide, azide, succinimidyl, or thiol groups to facilitate the reaction of the poly-(alkylene glycol) molecule with the drug, i.e. the cytotoxic or therapeutic peptide or polypeptide.

Additionally, the linker poly-(alkylene glycol) structure may also be reacted with a second linker via the linker arm to provide a homobifunctional linker, so that the vinyl group of one linker can be reacted with the thiol group of the drug, i.e. the cytotoxic or therapeutic peptide or polypeptide, and the vinyl group of the other linker can be conjugated to a thiol group of a protein, for example albumin. In this embodiment the protein drug conjugate, e.g. albumin drug conjugate will comprise two linker molecules, which will facilitate the joining of the albumin to thiol containing cytotoxins, therapeutic peptides or therapeutic polypeptides.

In a further embodiment of the present invention there is provided a method which comprises contacting albumin with a linker, which comprises a functionalising reagent, comprising a nitrogen containing heterocyclic aromatic ring having a vinyl substituent capable of reacting with the free thiol group of albumin, wherein the linker functionalising reagent is covalently linked to a poly-(alkylene glycol) molecule, so that the vinyl substituent of the linker functionalising reagent reacts with the thiol group of the albumin, thereby to covalently link the linker poly-(alkylene glycol) molecule to albumin.

This further method may comprise the initial step of modifying the albumin, e.g. by chemical reaction or site directed mutagenesis, to produce a variant having a thiol group at one or more desired positions of the polypeptide, e.g. to introduce a solvent exposed cysteine residue. Preferably, this is done by replacing one or more of the amino acids in the polypeptide chain of the albumin with a cysteine residue.

In a further aspect, the present invention provides a protein drug conjugate as defined above for use in therapy.

In one embodiment, there is provided an ADC as defined above for use in therapy. Preferably the ADC is intended for use in anticancer therapy.

In a further embodiment, the present invention provides an albumin drug conjugate as defined above for use in therapy. Preferably the albumin drug conjugate is intended for use in anticancer, antinociceptive, antidiabetes, antitumor or antiviral therapy.

Embodiments of the present invention will now be described by way of example and not limitation with reference to the accompanying figures.

Figure 1:
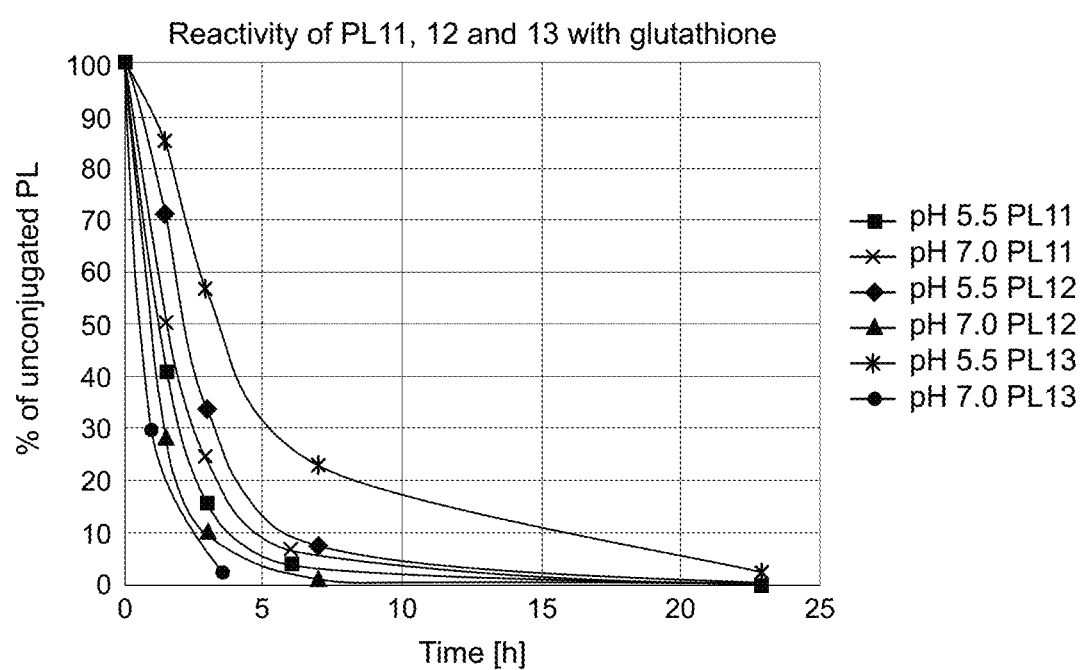
FIG. 1. Relative rates of reaction for example linkers in accordance with the present invention and glutathione.

The methods of the present invention are capable of providing protein drug conjugates, such as ADCs or albumin drug conjugates, in accordance with the present invention which comprise an antibody or albumin bound to a linker, which in turn is bound to a drug, such as a cytotoxin or a therapeutic peptide or polypeptide.

In the present invention, references to antibodies include immunoglobulins whether natural or partly or wholly synthetically produced. The term also covers any polypeptide or protein comprising an antigen binding domain. Antibody fragments are also contemplated which comprise antigen binding domains including Fab, scFv, Fv, dAb, Fd fragments, diabodies, triabodies or nanobodies. It is possible to take monoclonal and other antibodies and use techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP 0 184 187 A, GB 2,188,638 A or EP 0 239 400 A. Antibodies can be modified in a number of ways and the term should be construed as covering any specific binding member or substance having an antibody antigen-binding domain with the required specificity. Thus, this term covers antibody fragments and derivatives, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP 0 120 694 A and EP 0 125 023 A.

In the prior art it has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature 341, 544-546 (1989)) which consists of a VH domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al, Science, 242; 423-426, 1988; Huston et al, PNAS USA, 85: 5879-5883, 1988); (viii) bispecific single chain Fv dimers (PCT/US92/09965) and (ix) "diabodies", multivalent or multispecific fragments constructed by gene fusion (WO 94/13804; Holliger et al, P.N.A.S. USA, 90: 6444-6448, 1993). Fv, scFv or diabody molecules may be stabilised by the incorporation of disulphide bridges linking the VH and VL domains (Reiter et al, Nature Biotech, 14: 1239-1245, 1996). Minibodies comprising a scFv joined to a CH3 domain may also be made (Hu et al, Cancer Res., 56: 3055-3061, 1996). Accordingly, such binding fragments are contemplated by the present invention.

In preferred embodiments, the methods disclosed herein employ reagents and conditions that are well adapted for binding a protein, such as an antibody, via a linker to a drug, such as a cytotoxin. In particular, the reaction conditions that are used in the present method helps to avoid the problems that tend to occur when using prior art reagents such as maleimide, which have a tendency to produce a mixture of different products with a range of different properties. More especially, as can be seen from the experimental data below, methods of producing protein drug conjugates, such as ADCs, which utilise linkers according to the present invention, avoid the problems associated with maleimide cross-linking.

As mentioned above, the protein of interest (e.g. the antibody) for the protein drug conjugate (e.g. ADC) composition may be bound to the linker using existing thiol groups or by introducing thiol groups in an initial step of the method, for example by reacting one or more functional groups of the protein (e.g. antibody) to produce a thiol group, or by introducing a thiol group or a precursor thereof into the protein (e.g. antibody). By way of example, this may involve the step of introducing a cysteine residue into the protein (in the example an antibody) at a site where it is desired to bind the linker to the protein (e.g. antibody). This may be useful in situations where a convenient cysteine residue for reaction according to the present invention is not present in a starting or wild-type polypeptide/protein. Conveniently, this may be achieved using site directed mutagenesis of the protein, such as an antibody polypeptide, the use of which is well established in the art.

Alternatively or additionally, an initial reduction step may be required where the protein is commercial grade albumin as the majority of cysteine thiols present are capped, as discussed in further details below Experimental Data and Discussion The following experimental data was mainly produced utilising the linker molecule identified as, and referred to herewith as, PL13, in its free acid or NH-pegylated form, as shown below.

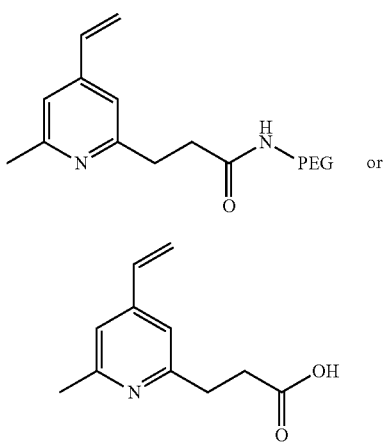

1. Demonstration of PL11, PL12 and PL13 Linker Reactivity with Glutathione.

Glutathione contains a thiol group which is readily available for conjugation, and can provide a good model for proteins to assess the suitability of linkers for use in the present invention for utility in protein drug conjugates, such as ADCs. FIG. 1 shows three linker group examples according to the present invention and demonstrates their ability to conjugate to the thiol groups present in glutathione. The examples in FIG. 1 are PL11, PL12 and PL13, and their structures are shown below.

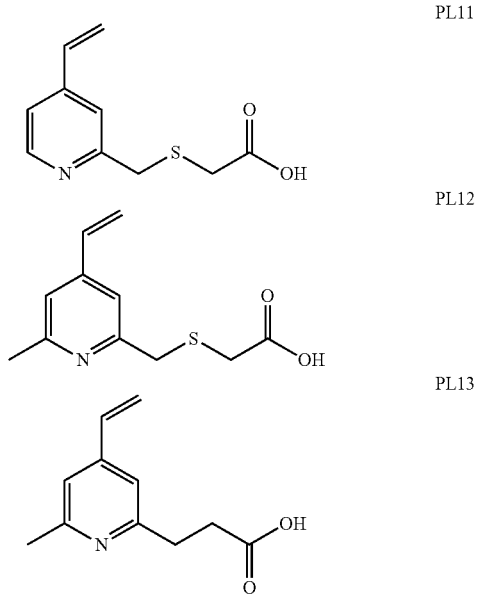

2. Determination of PL13 Free Acid Selectivity

The data given below demonstrates that linkers in accordance with the present invention show specificity for cysteine groups. PL13 free acid is identified as;

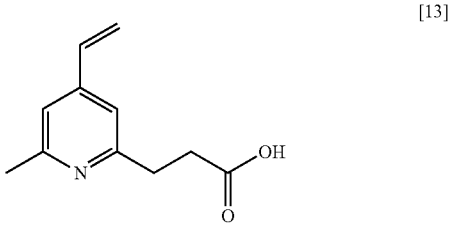

Reactivity of PL13 Free Acid with N-Acetyl Cysteine at pH 7.0, 7.5 and 8.0

PL13 free acid was reacted with 2 molar equivalents of N-acetyl cysteine (NAC) at three separate pHs: 7.0, 7.5 and 8.0. Reactions were carried out in a methanol/phosphate buffered saline (PBS) solution (ratio of 9:1), buffered to the appropriate pH at room temperature (RT). RP-HPLC analysis with a gradient of 1% to 50% B (Acetonitrile with 0.1% TFA) over 15 minutes and detection at 254 nm was undertaken to monitor addition of free thiol to the vinyl group of PL13 over time.

Method:

210 µL of 2.61 mM PL13 free acid in methanol was mixed with 22 µL of 50 mM NAC in buffer to give a final concentration of 2.37 mM PL13 free acid and 4.74 mM NAC.

Figure 2:
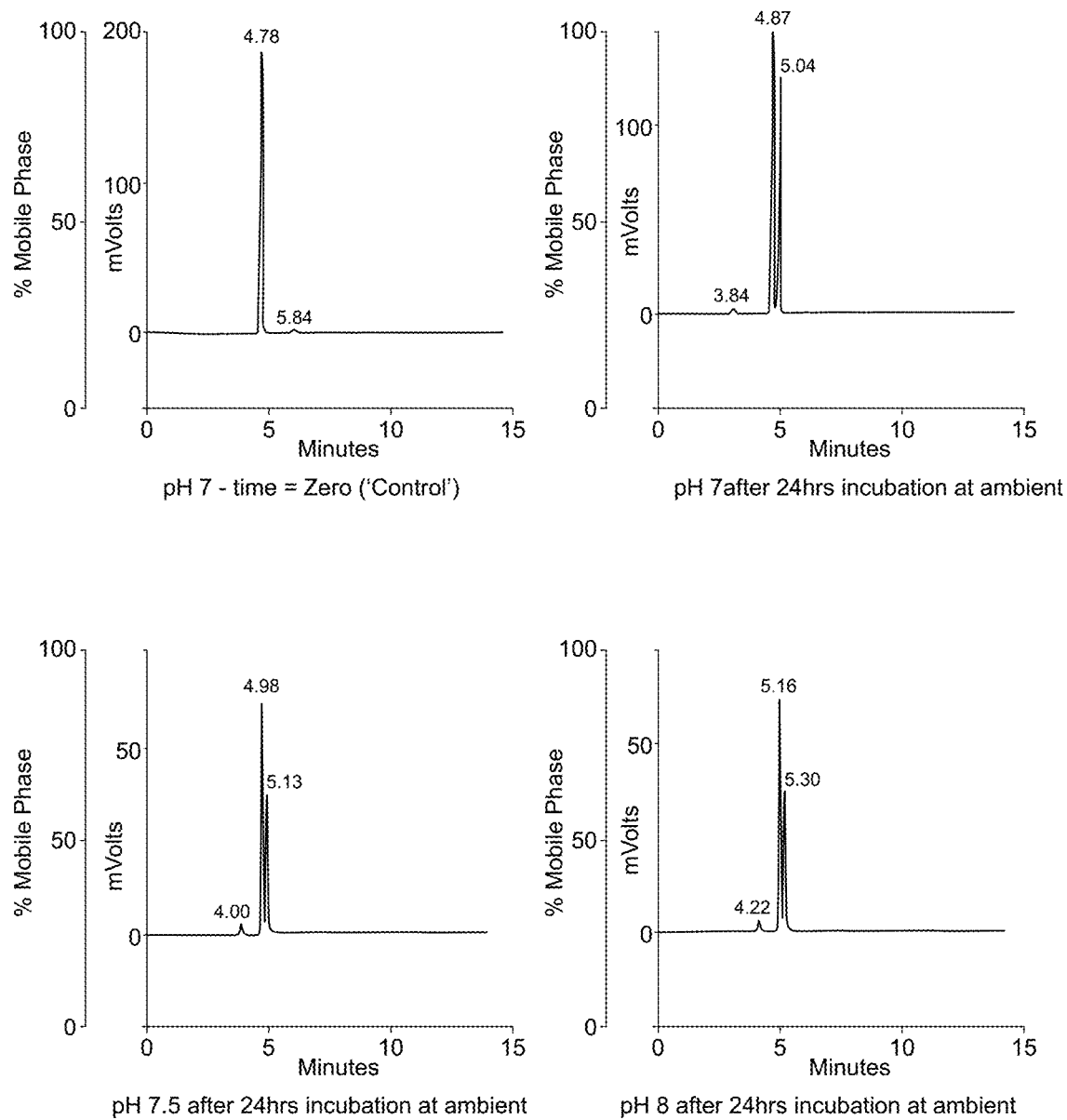
FIG. 2. RP-HPLC analysis of PL13 free acid reactivity with N-acetyl cysteine (NAC) after 24 hours at three different pHs (7.0, 7.5 and 8.0).

Results:

The PL13-NAC adduct was eluted at retention time of 5.1 minutes at all pHs after 24 hours (see FIG. 2). The amount of product (PL13-NAC adduct) was similar at pH 7.0 and 8.0. The reactivity of PL13 free acid at pH 7.5 was slower. In addition, an unidentified peak was eluted at 4 minutes.

Figure 3:
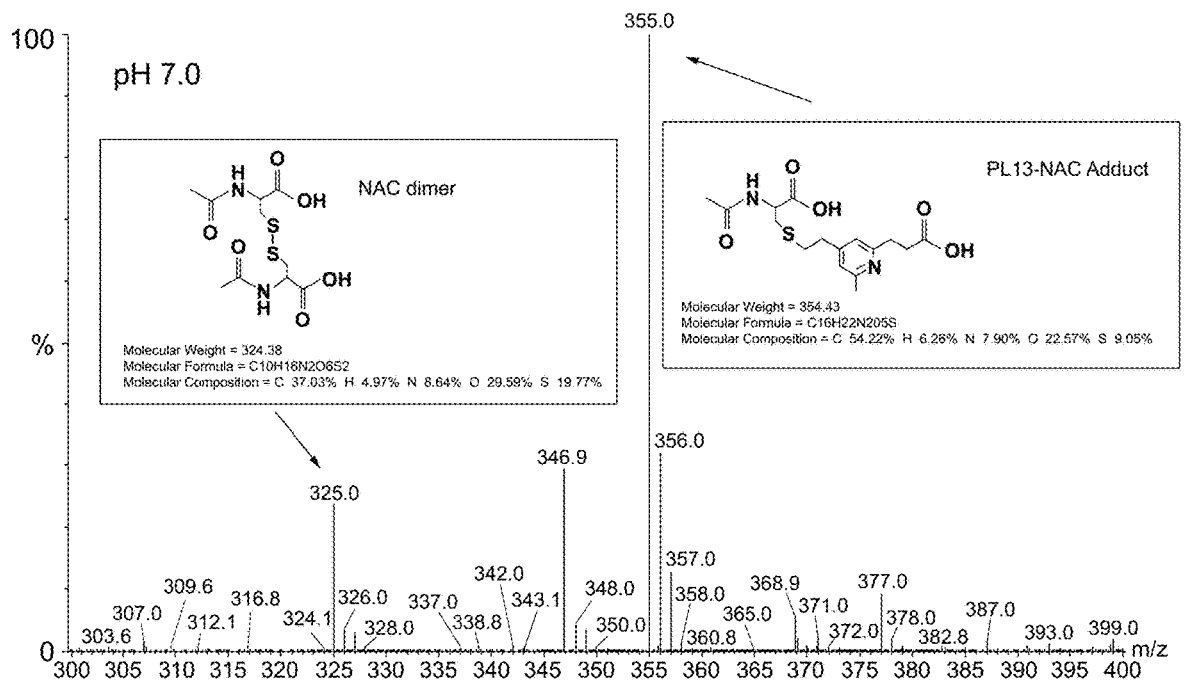
FIG. 3. MS data to demonstrate formation of PL-13-NAC Adduct at pH 7.0.
Figure 4:
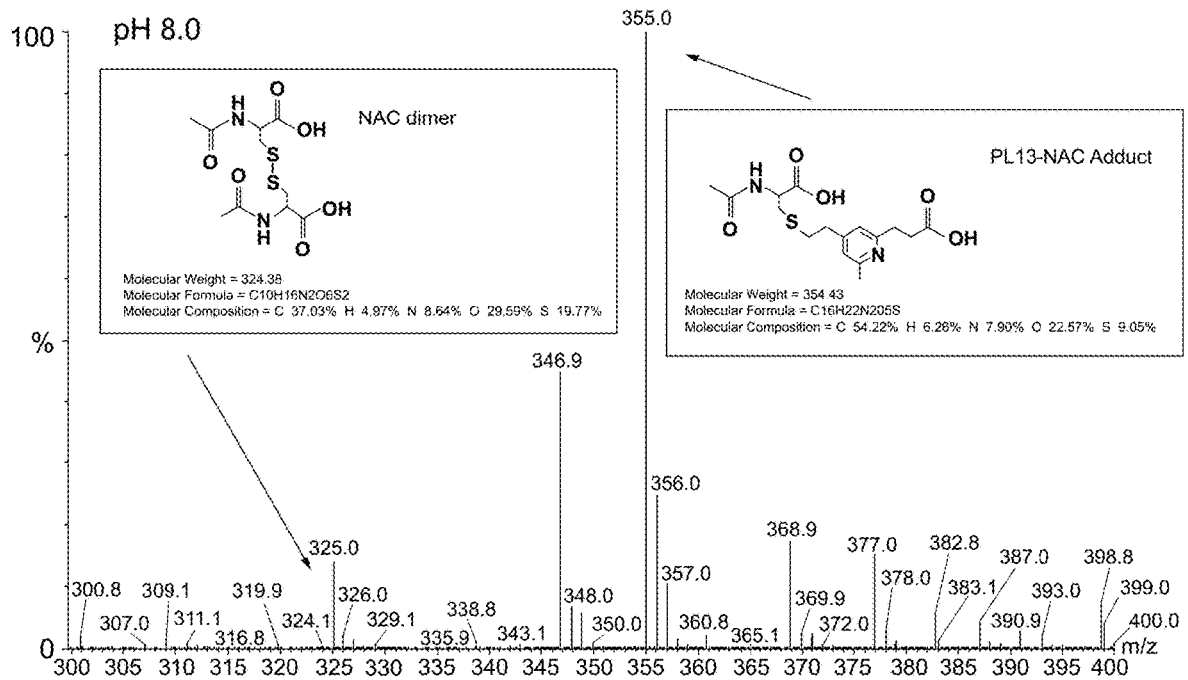
FIG. 4. MS data to demonstrate formation of PL-13-NAC Adduct at pH 8.0.

ESI-MS analysis confirmed the presence of the PL13-NAC adduct at all analysed pHs. MS trace data is included herewith to show this analysis as performed at pH 7.0 (FIG. 3.), and pH 8.0 (FIG. 4.).

Reactivity of PL13 Free Acid with N-Acetyl Cysteine at pH 8.0

Figure 5:
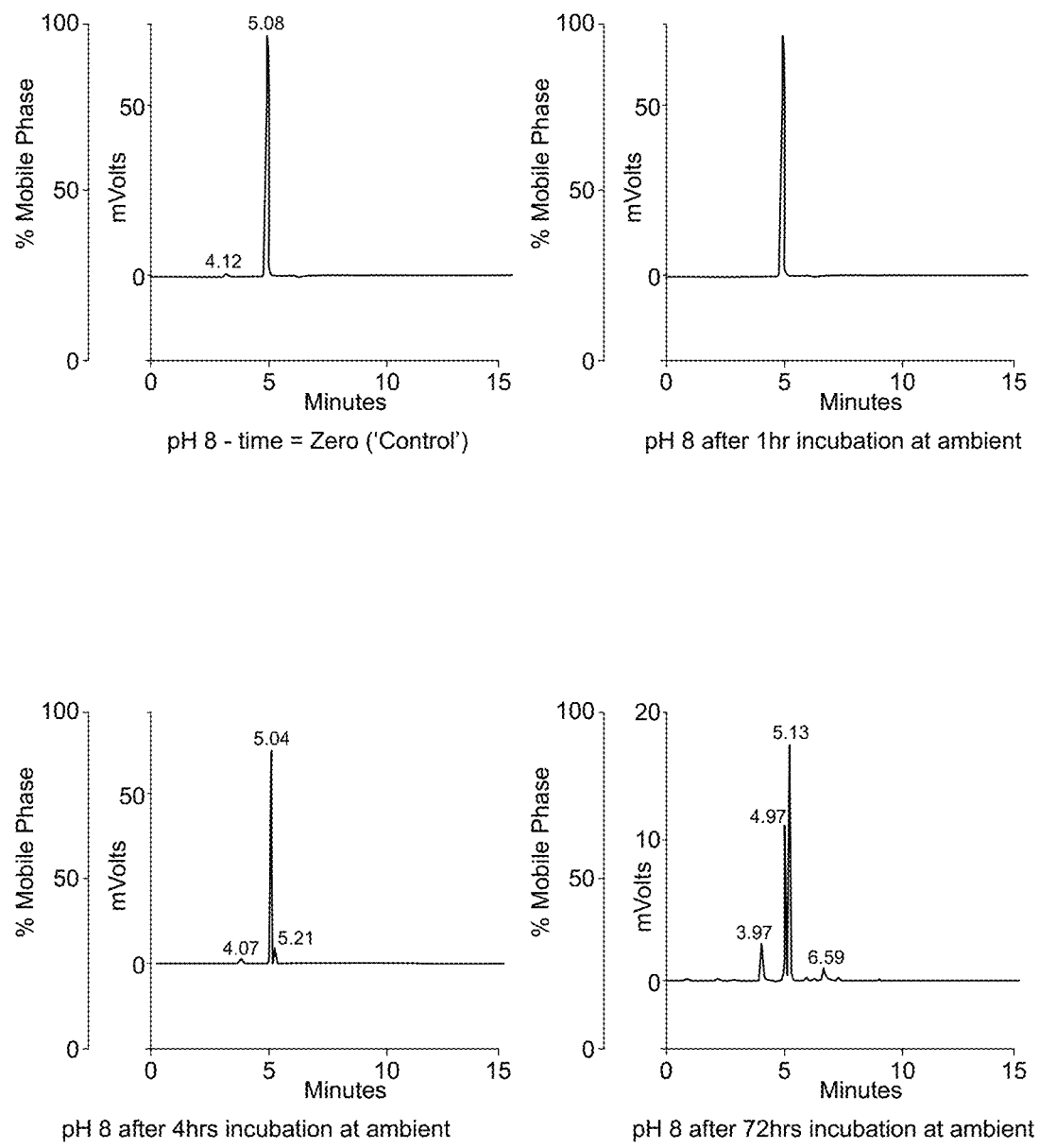
FIG. 5. RP-HPLC analysis of PL13 free acid reactivity with NAC at pH 8.0.

PL13 free acid was reacted with 2 molar equivalents of NAC in methanol/PBS solution (9:1), pH 8.0. The progress of the reaction was monitored by RP-HPLC using a gradient of 1% to 50% B over 15 minutes with detection at 254 nm. Samples were analysed at 0, 1, 4 and 72 hours of incubation at RT (see FIG. 5.).

Method:
100 µL of 2.61 mM PL13 free acid in methanol was mixed with 11 µL of 50 mM NAC in buffer at pH 8.0 to give a final concentration of 2.35 mM PL13 free acid and 5 mM NAC.

Results:
Addition of PL13 free acid to NAC is slow over the first 4 hours. After 72 hours of incubation ~70% of PL13 free acid was converted to product (PL13-NAC adduct) at pH 8.0.

Reactivity of PL13 Free Acid with 10 Equivalents of Tyrosine, Histidine, Lysine and N-Acetyl cysteine at pH 7.0

PL13 free acid was challenged with 10 equivalents of each amino acid (tyrosine (Tyr), histidine (His), Lysine (Lys) and N-acetyl cysteine (NAC)) at pH 7.0. The reaction was analysed by RP-HPLC using a gradient of 1 to 50% B over 15 minutes with detection set at 254 nm.

Method:
50 µL of 2.61 mM PL13 in methanol was mixed with 260 µL of 20 mM Tyr/His/Lys and NAC in buffer to give a final concentration of 0.42 mM PL13 and 4.2 mM of each of Tyr, His, Lys and NAC.

Figure 6:
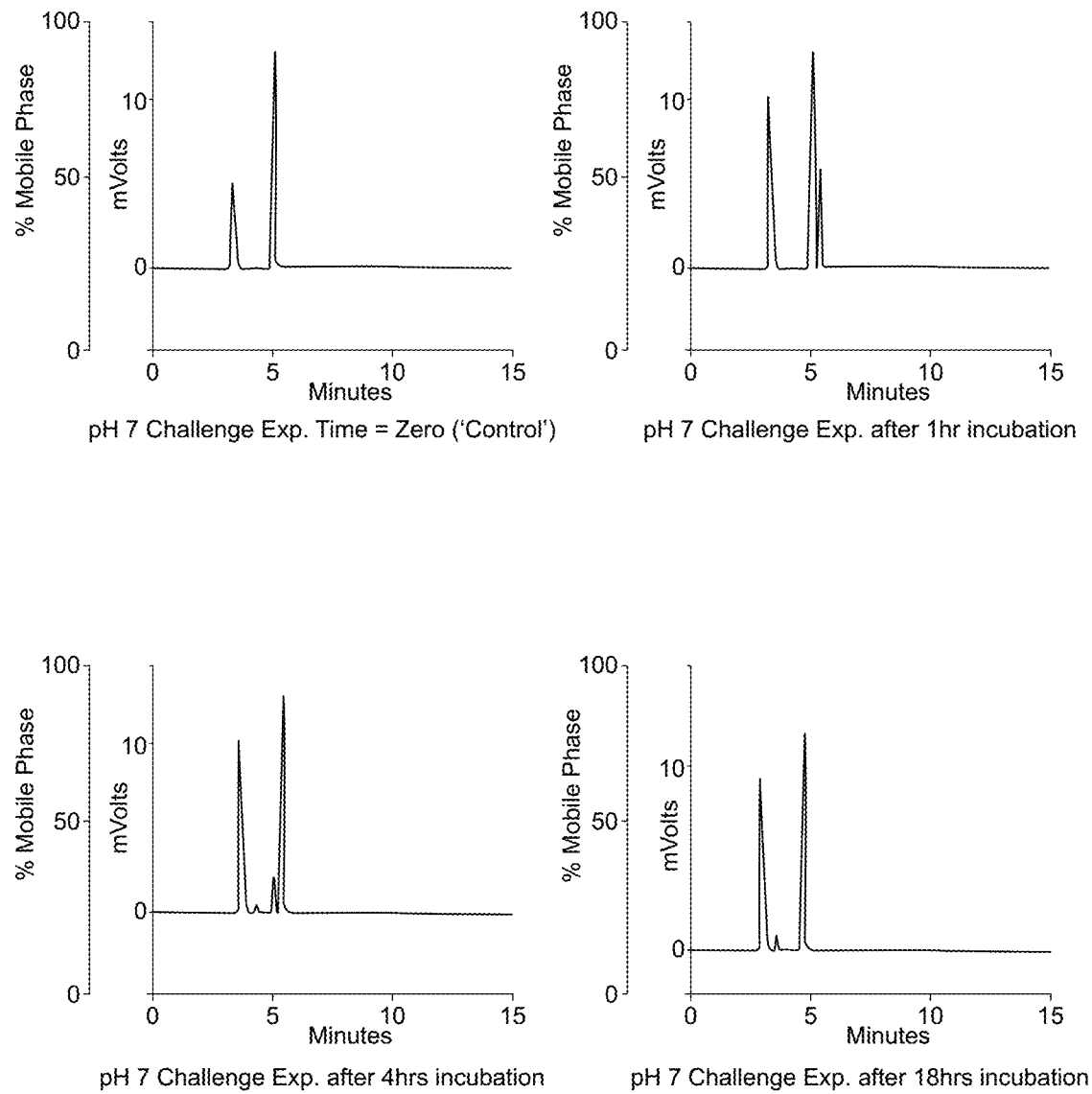
FIG. 6. RP-HPLC analysis of PL13 free acid reactivity with a mixture of amino acids (Tyr/Lys/His/NAC) at pH 7.0.
Figure 7:
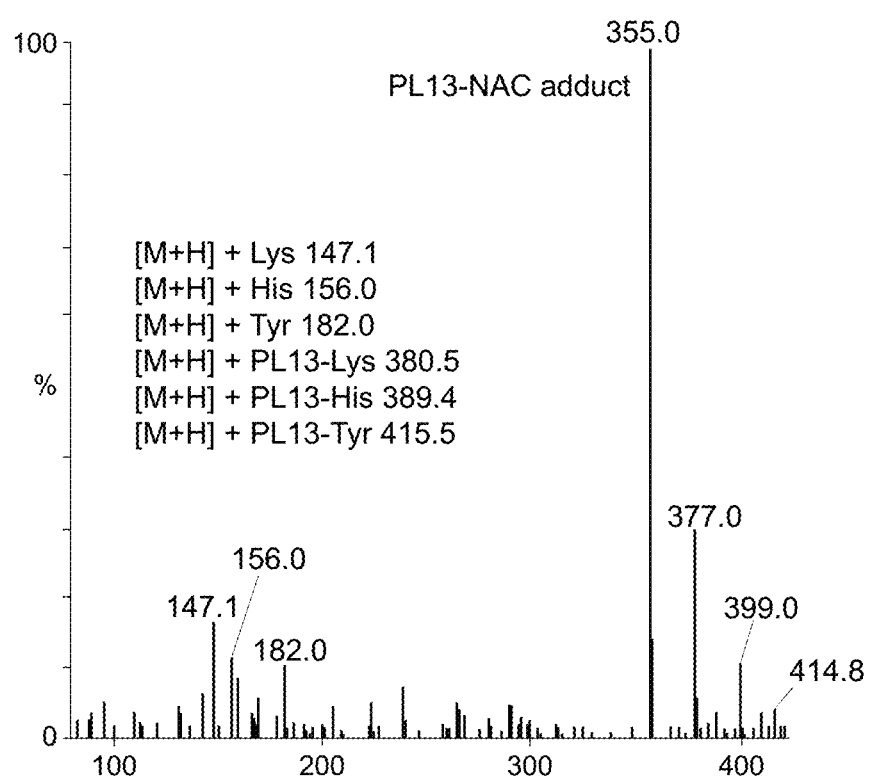
FIG. 7. MS data to demonstrate formation of PL13-NAC in reactivity with amino acid mixture at pH 7.0.

Results:
PL13 free acid reacted selectively with NAC in the presence of Tyr, His and Lys at pH 7.0 (see FIG. 6). FIG. 7 shows the MS data to demonstrate that only the PL13 NAC adduct was formed.

The addition reaction between PL13 and NAC increased significantly at 10 molar excess of amino acid. Conversion of PL13 free acid to the desired PL13-NAC adduct is 90% complete after 4 hours at room temperature (RT) and is fully complete in <18 hours.

The results obtained demonstrate the selectivity of the free acid form of the linker molecule in accordance with the present invention for cysteine reactivity via the vinyl group of the linker molecule.

RP-HPLC Analysis of PL13 Free Acid Reactivity with Lysine.

PL13 free acid was challenged with 10 equivalents of Lys in PBS buffer, pH 7.4 at RT. The reaction was analysed by RP-HPLC using a gradient of 12 to 50% acetonitrile in water over 30 minutes with detection set at 270 nm.

Method:
10 µL of 4 mM PL13 in methanol was mixed with 50 µL of 8 mM Lys solution and 40 µL of PBS buffer pH 7.4 to give a final concentration of 0.4 mM PL13 and 4.0 mM Lys. The reaction was analysed by RP-HPLC using a gradient of 12 to 50% acetonitrile in water over 30 minutes with detection set at 270 nm.

Figure 8:
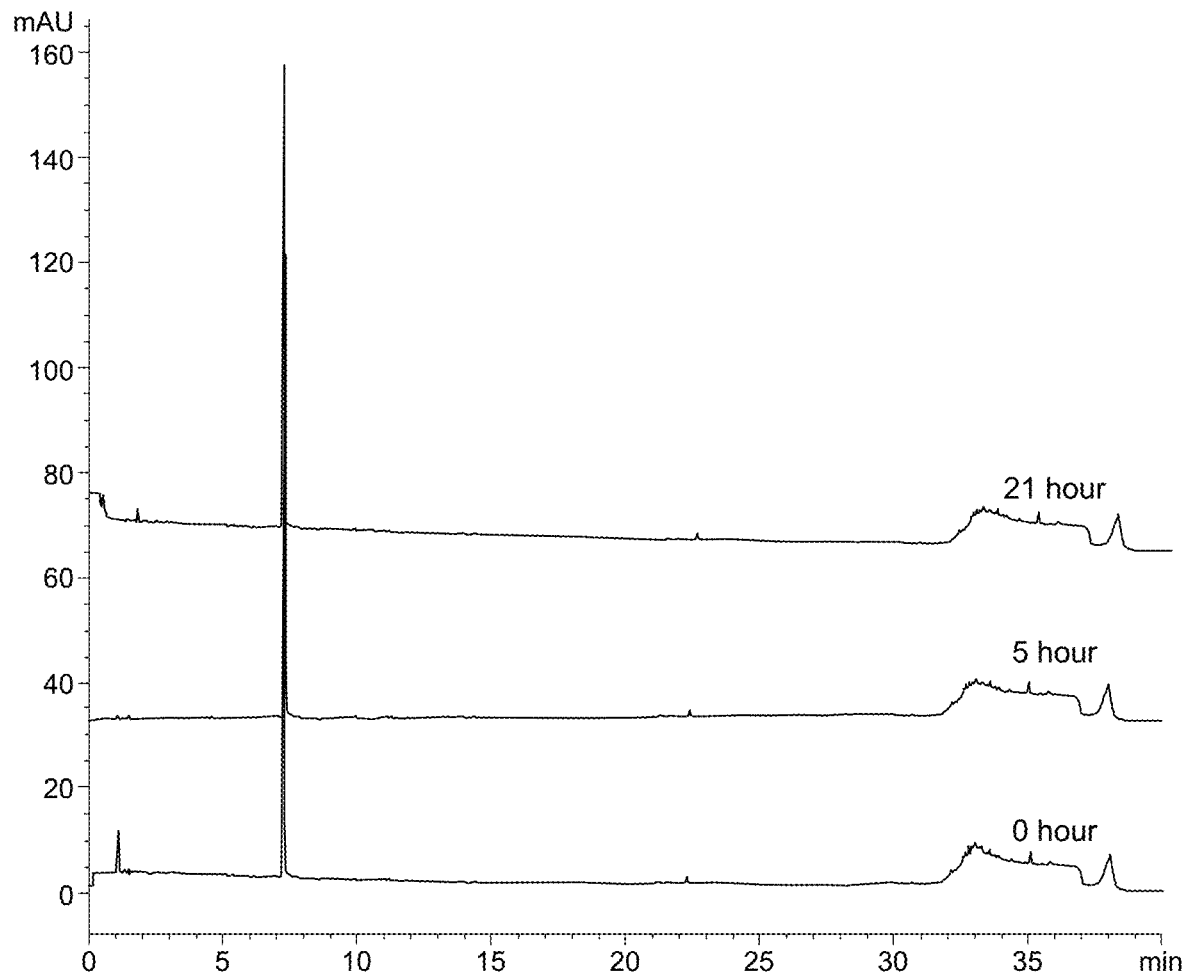
FIG. 8. RP-HPLC analysis of PL13 free acid reactivity with 10 equivalents of Lysine at pH 7.0.

Results:
PL13 free acid did not react with Lys at pH 7.4 as no peak is observed in the RP-HPLC analysis corresponding to a PL13-Lys adduct (see FIG. 8).

The results obtained demonstrate that no adduct is formed by the incubation of PL13 free acid with Lys. This data supports the cysteine group selectivity of the free acid form of linkers of the present invention. It should be appreciated that no such cysteine specificity is exhibited by maleimide and as such the linkers of the present invention present a benefit in this regard.

While the above data shows the cysteine specificity exhibited by the linkers of the present invention, it is readily appreciated that lysine specificity may alternatively be achieved if the linker is modified by methods well known in the art.

Reactivity of PL13 Free Acid with Aspartic Acid

PL13 free acid was treated with 10 equivalents of aspartic acid (Asp) at pH 7.0 and at RT. Analysis was performed by RP-HPLC at gradient of 1% to 50% B over 15 minutes with detection at 254 nm.

Method:
50 µL of 2.61 mM PL13 free acid in methanol was mixed with 280 µL of 50 mM Asp in buffer to give a final concentration of 0.42 mM PL13 free acid and 4.2 mM Asp.

Figure 9:
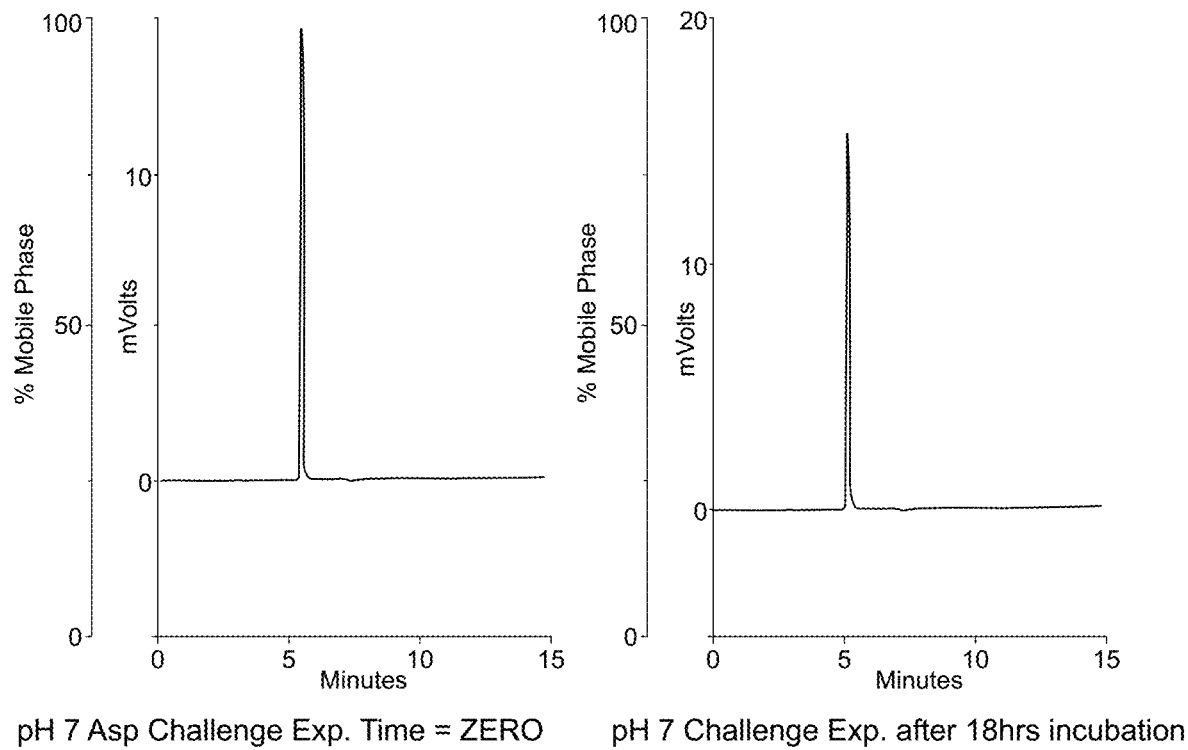
FIG. 9. RP-HPLC analysis of PL13 free acid reactivity with 10 equivalents of aspartic acid.

Results:
PL13 free acid is stable in the presence of Asp at pH 7.0 over 18 hours at RT (see FIG. 9).

MS spectra substantiates that no adduct is formed by the incubation of PL13 free acid with Asp (data not shown). Again, this data supports the cysteine group selectivity of the linkers of the present invention. It should be appreciated that no such cysteine specificity is exhibited by maleimide and as such the linkers of the present invention present a benefit over this.

3. Synthesis of PL13-Val-Cit-4-aminobenzoyl-MMAE Cytotoxic Drug Linker

PL13-val-cit-4-aminobenzoyl-MMAE was synthesised by a fragment approach, which will be familiar to the person skilled in the art.

Method:
PL13 free acid was coupled to the free amino terminal of H-val-cit-4-aminobenzoyl-MMAE, an exemplary cytotoxin, via a HOBt active ester method.

Figure 10:
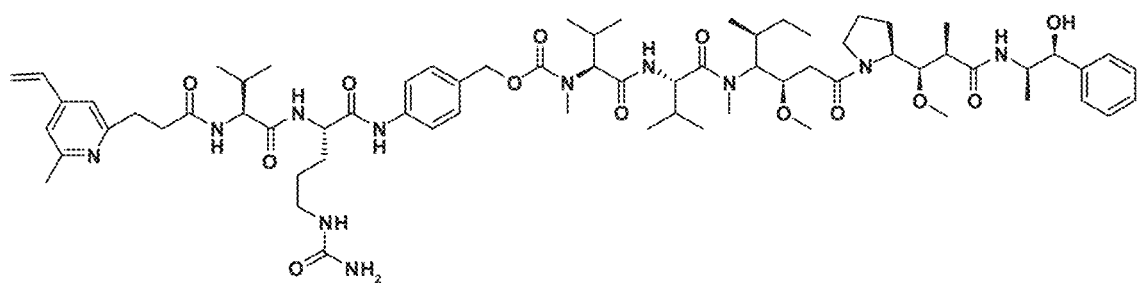
FIG. 10. Structure of PL13-val-cit-4-aminobenzoyl-MMAE.

Results:
3.1 mg of PL13-val-cit-4-aminobenzoyl-MMAE (see FIG. 10) was synthesised. The material was solubilised in dimethyl-acetamide (DMA) to afford a drug linker solution at a concentration of 50 mM.

RP-HPLC confirmed purity of the PL13-val-cit-4-aminobenzoyl-MMAE linker (data not shown).

Figure 11:
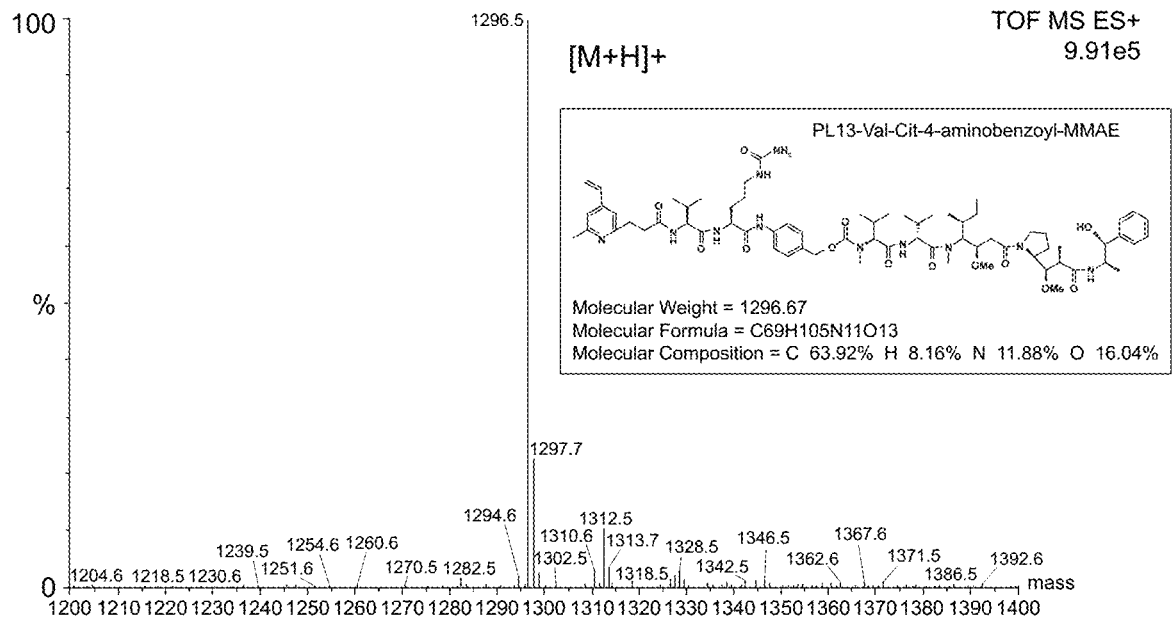
FIG. 11. MS analysis of PL13-val-cit-4-aminobenzoyl-MMAE.

ESI-MS analysis confirmed the identity of the cytotoxic drug linker (expected MW is 1296.67 Da, experimental result gave MW of 1296.5 Da) (see FIG. 11).

4. Generation of Trastuzumab-PL13-Val-Cit-4-aminobenzoyl-MMAE and Trastuzumab-maleimide-val-cit-4-aminobenzoyl-MMAE 20 mg of Trastuzumab-PL13-val-cit-4-aminobenzoyl-MMAE conjugate, an exemplary ADC of the present invention, and 20 mg of Trastuzumab-maleimide-val-cit-4-aminobenzoyl-MMAE conjugate, an ADC comprising a known maleimide linker, were produced.

Conjugation of PL13-val-cit-4-aminobenzoyl-MMAE and Maleimide-val-cit-4-aminobenzoyl-MMAE to Trastuzumab Method:
Trastuzumab was reduced to allow conjugation of 3-4 drugs per trastuzumab molecule. A detailed method for the reduction of trastuzumab is not provided as this should be well known by the person skilled in the art.

Maleimide-val-cit-4-aminobenzoyl-MMAE was conjugated to Trastuzumab at 1.25 molar excess over free thiol at pH 7.0. The reaction was performed for 1 hour at RT. The conjugation reaction was quenched by an excess of NAC. Analysis of the Trastuzumab conjugate was accomplished by Hydrophobic Interaction Chromatography (HIC) using a Tosoh butyl-NPR (4.6×3.5, 2.5 µm) column and by UV-VIS spectroscopy. MMAE has a distinctive UV absorbance at 248 nm ($\varepsilon_{248}$=1500 $M^{-1}$ cm, $\varepsilon_{280}$=15900 $M^{-1}$ cm).

PL13-val-cit-4-aminobenzoyl-MMAE was coupled to Trastuzumab at 1.25, 2.5, 5 and 10 molar excess over free thiol. Reactions were carried out for 16 hours at pH 7.0. Conjugation reactions were analysed by both HIC (separation on a Tosoh butyl-NPR column) and PLRP chromatography (separation on a PLRP column—2.1 mm×5 cm, 5 µm). Trastuzumab conjugates were examined by UV-VIS spectroscopy. Both the MMAE cytotoxic drug and PL13 linker contribute to UV absorbance at 248 nm.

Figure 12:
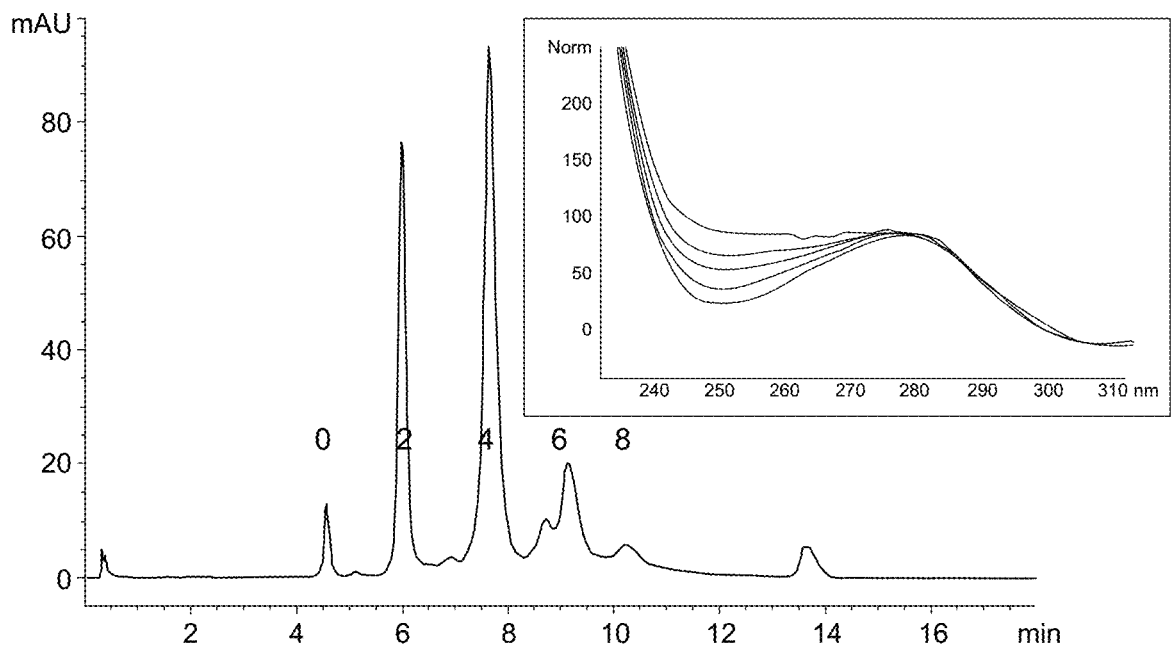
FIG. 12. HIC and UV-Vis profiles of Trastuzumab-maleimide-val-cit-4-aminobenzoyl-MMAE after 1 hour of reaction.

Results:

Reaction of maleimide-val-cit-4-aminobenzoyl-MMAE with Trastuzumab was completed within 1 hour using a ratio of 1.25 drug over free thiol (see FIG. 12). The numbers in FIG. 12 designate the amount of drug conjugated to a full length antibody. The inlet is the UV-Vis profile which represents an increase of absorbance at 248 nm due to conjugation of maleimide-val-cit-4-aminobenzoyl-MMAE to Trastuzumab. 10 mg of the trastuzumab-maleimide-val-cit-4-aminobenzoyl-MMAE conjugate (Drug to Antibody Ratio (DAR) 2.2) was obtained and set aside for in vitro studies, as discussed further below.

Figure 13:
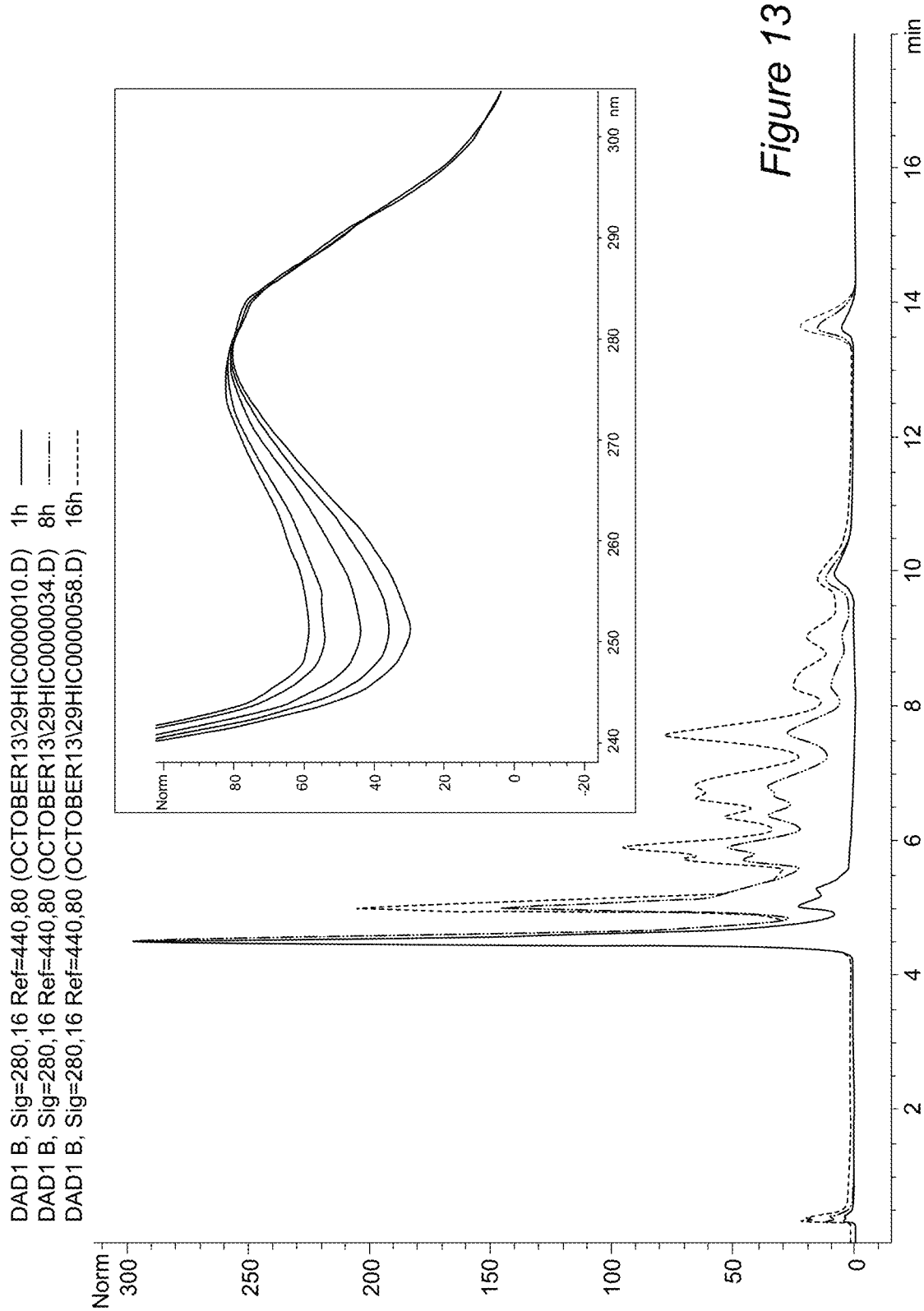
FIG. 13. HIC and UV-Vis profiles of the Trastuzumab-PL13-val-cit-4-aminobenzoyl-MMAE conjugate at 1, 8 and 16 hours of incubation with 1.25 molar excess of drug-linker over thiol.
Figure 14:
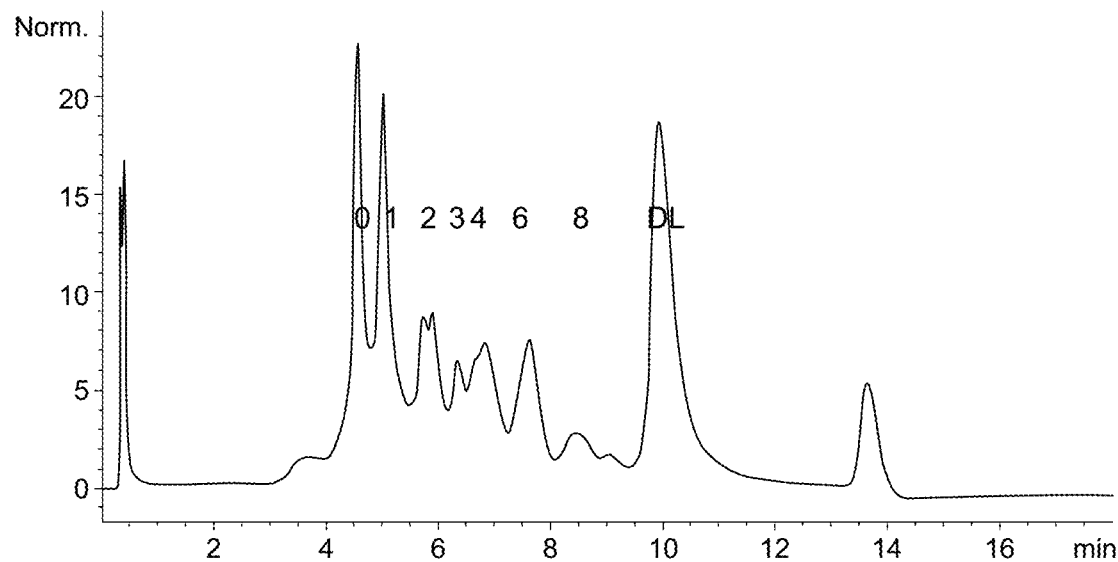
FIG. 14. HIC profile of the Trastuzumab-PL13-val-cit-4-aminobenzoyl-MMAE conjugate at 16 hours of incubation with 5 molar excess of drug-linker over thiol.

The rate and efficiency of the PL13-val-cit-4-aminobenzoyl-MMAE reaction is much slower than the maleimide-val-cit-4-aminobenzoyl-MMAE due to low solubility of the linker (see FIG. 13). Conjugation was performed at 1.25 molar excess of drug-linker over thiol. The inlet is the UV-Vis profile which depicts an increase of absorbance at 248 nm due to coupling of PL13-val-cit-4-aminobenzoyl-MMAE to Trastuzumab within 16 hours. A slow increase in the rate of PL13-val-cit-4-aminobenzoyl-MMAE conjugation to Trastuzumab was observed by applying 5 molar excess of drug-linker over thiol group (see FIG. 14). In FIG. 14, the numbers designate the amount of drug conjugated to a full length antibody. DL indicates unconjugated drug.

Figure 15:
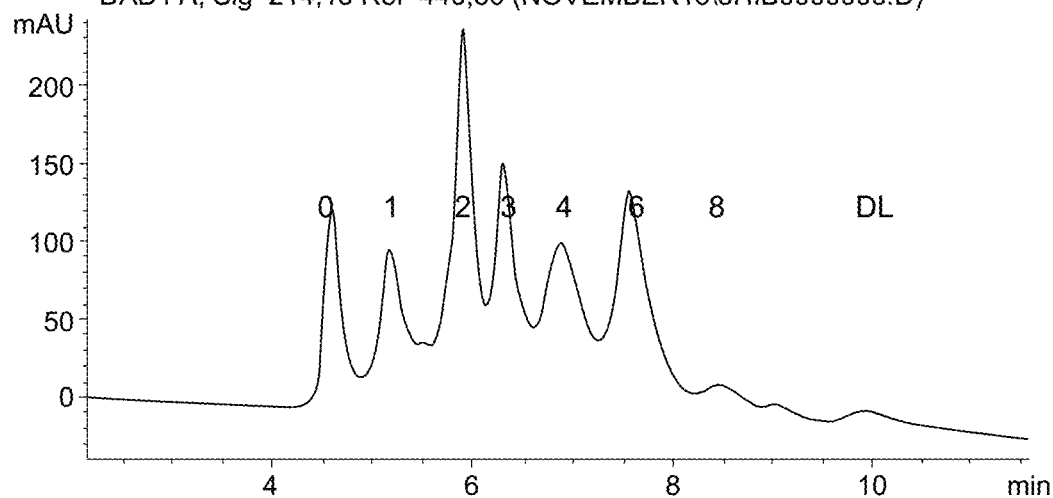
FIG. 15. HIC profile of Trastuzumab-PL13-val-cit-4-aminobenzoyl-MMAE obtained via conjugation of 10 molar excess of PL13-val-cit-4-aminobenzoyl-MMAE after 16 hours of incubation.
Figure 16:
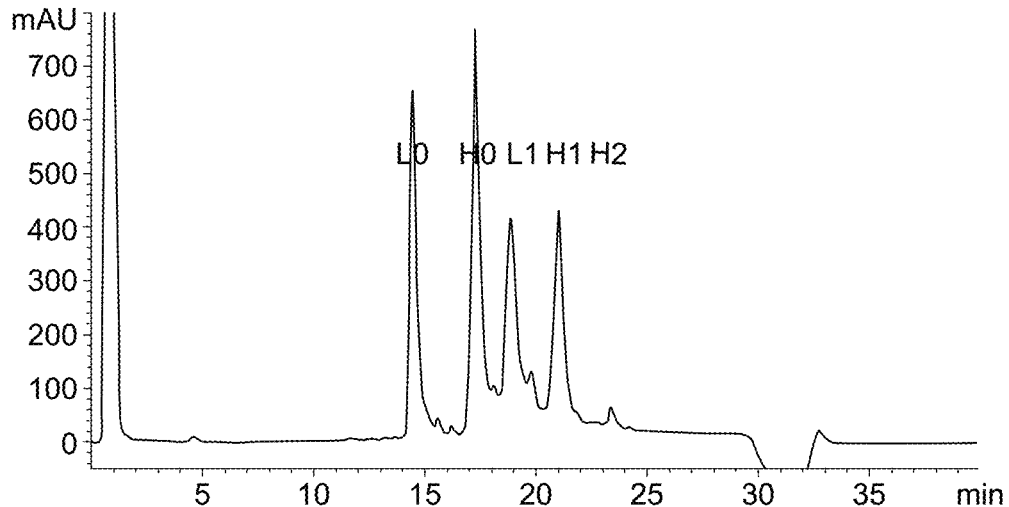
FIG. 16. PLRP profile of Trastuzumab-PL13-val-cit-4-aminobenzoyl-MMAE conjugated at 10 molar excess of PL13-val-cit-4-aminobenzoyl-MMAE after 16 hours of incubation.

Conjugation of PL13-val-cit-4-aminobenzoyl-MMAE to Trastuzumab at 10 molar excess and in the presence of 50% propylene glycol resulted in 90% yield within 4 hours (see FIG. 15 and FIG. 16). In FIG. 15, the numbers designate the amount of drug conjugated to a full length antibody. DL indicates unconjugated drug. In FIG. 16, the numbers designate the amount of drug conjugated to light (L) or heavy (H) chain of the antibody. 7.2 mg of Trastuzumab-PL13-val-cit-4-aminobenzoyl-MMAE conjugate (DAR 3.03), was obtained and set aside for in vitro studies, as discussed further below.

Determination of Drug Antibody Ratio (DAR) for Trastuzumab-PL13-val-cit-4-aminobenzoyl-MMAE and Trastuzumab-maleimide-val-cit-4-aminobenzoyl-MMAE.

HIC and PLRP chromatography are often applied to characterize average drug-load and drug-load distribution for cysteine-linked ADCs. Determination of average drug-load and drug-load distribution is a crucial attribute as it effects the potency and pharmacokinetics of the ADC.

Results:

HIC characterisation of Trastuzumab-maleimide-val-cit-4-aminobenzoyl-MMAE resulted in a DAR calculation of 2.2 with 1.8% unconjugated Trastuzumab (see FIG. 12). The DAR calculation from the HIC profile is determined by well known methods in the art, as discussed below in relation to FIG. 27.

HIC analysis of Trastuzumab-PL13-val-cit-4-aminobenzoyl-MMAE resulted in peaks which did not resolve well enough to support DAR determination (see FIG. 15). However, this data is included here for completeness. HIC was used to calculate the amount of Trastuzumab with DAR 0 calculated to be ~8.4%.

Figure 17:
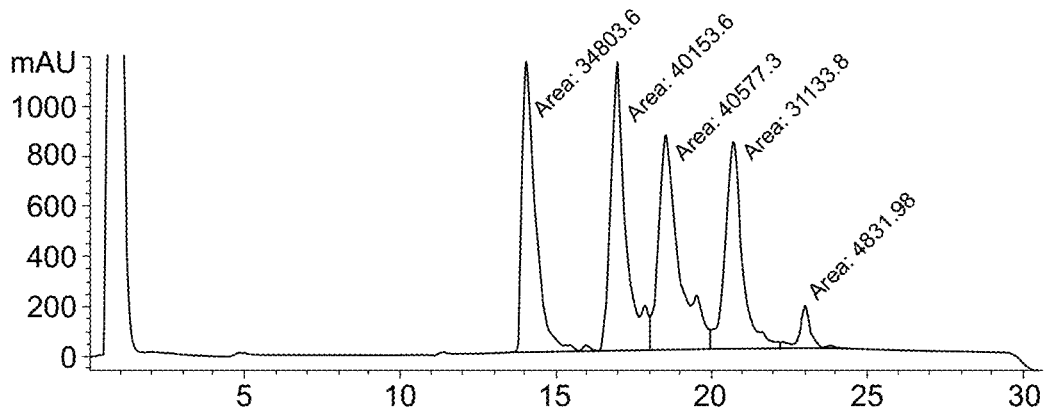
FIG. 17. PLRP profile of double desalted Trastuzumab-PL13-val-cit-4-aminobenzoyl-MMAE.

Separation of dithiothreitol (DTT) reduced Trastuzumab-PL13-val-cit-4-aminobenzoyl-MMAE via a PLRP column afforded well resolved peaks (FIG. 16) corresponding to unconjugated or drug conjugated antibody light and heavy chains. A DAR of 3.0 was calculated for Trastuzumab-PL13-val-cit-4-aminobenzoyl-MMAE (see FIG. 17). The table in FIG. 17 depicts the DAR calculation for Trastuzumab-PL13-val-cit-4-aminobenzoyl-MMAE based on the percentage area of unconjugated and drug loaded light and heavy chains.

5. Stability Studies of Trastuzumab-PL13-Val-Cit-4-aminobenzoyl-MMAE and Trastuzumab-maleimide-Val-Cit-4-aminobenzoyl-MMAE Stability of drug-linker for the trastuzumab-maleimide-val-cit-4-aminobenzoyl-MMAE and trastuzumab-PL13-val-cit-4-aminobenzoyl-MMAE conjugates was evaluated in the presence of NAC in PBS buffer.

Method:

Each ADC (at concentration of 1-2 mg/mL), was incubated with 1 mM NAC in PBS buffer for 24 hours at 37° C.

Figure 18:
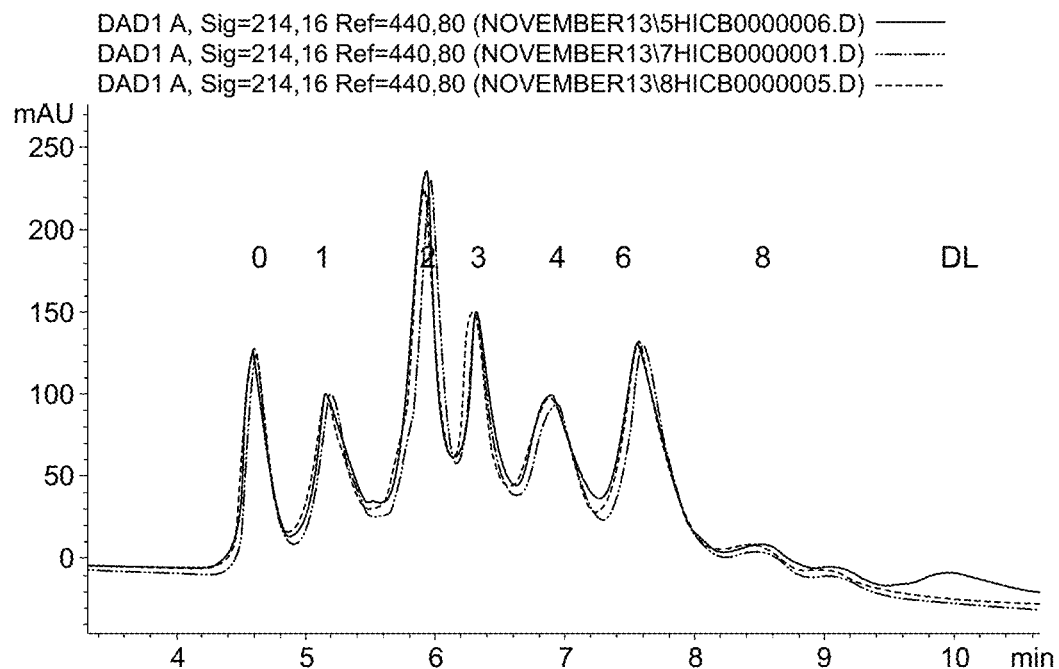
FIG. 18. HIC analysis of the Trastuzumab-PL13-val-cit-4-aminobenzoyl-MMAE conjugate in the presence of NAC at 0, 24 and 48 hours.
Figure 19:
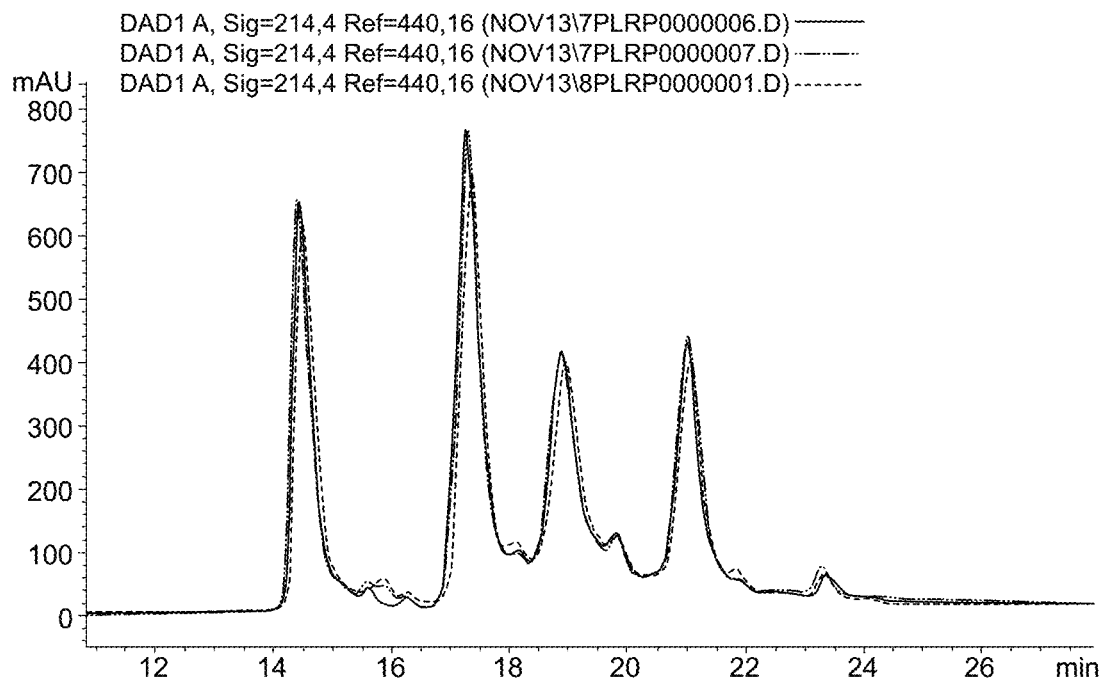
FIG. 19. PLRP profile of the Trastuzumab-PL13-val-cit-4-aminobenzoyl-MMAE conjugate in the presence of NAC at 0, 24 and 48 hours.
Figure 20:
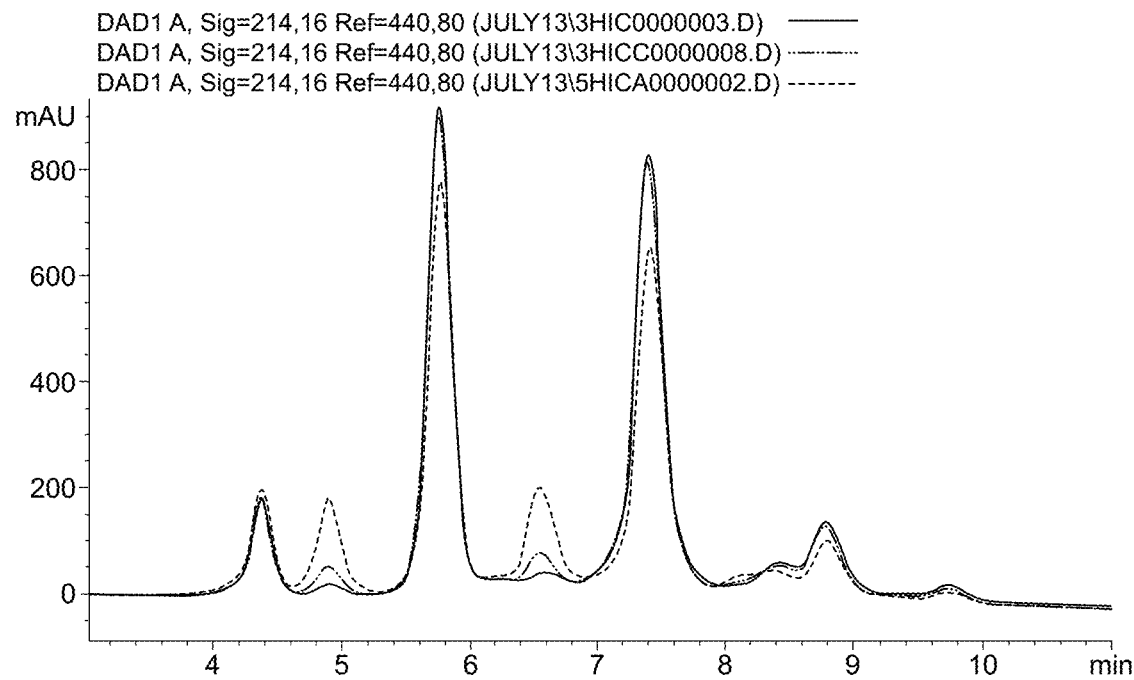
FIG. 20. HIC analysis of the Trastuzumab-maleimide-val-cit-4-aminobenzoyl-MMAE conjugate in the presence of NAC at 0, 24 and 48 hours.

Results:

The trastuzumab-PL13-val-cit-4-aminobenzoyl-MMAE conjugate was not influenced by the presence of NAC in buffer (see FIGS. 18 and 19). Trastuzumab-maleimide-val-cit-4-aminobenzoyl-MMAE showed decreased stability in the presence of NAC (see FIG. 20). In FIG. 18, the numbers designate the amount of drug conjugated to a full length antibody. DL indicates unconjugated drug.

FIG. 19 in particular demonstrates there is no profile change for the PL13 containing ADC resulting from challenge from free thiol, indicating stability of the construct.

6. SDS-PAGE and SEC Analysis of Trastuzumab-PL13-Val-Cit-4-aminobenzoyl-MMAE and Trastuzumab-maleimide-Val-Cit-4-aminobenzoyl-MMAE Trastuzumab-maleimide-val-cit-4-aminobenzoyl-MMAE and Trastuzumab-PL13-val-cit-4-aminobenzoyl-MMAE were evaluated by SEC chromatography and non-reducing SDS-PAGE.

Figure 21:
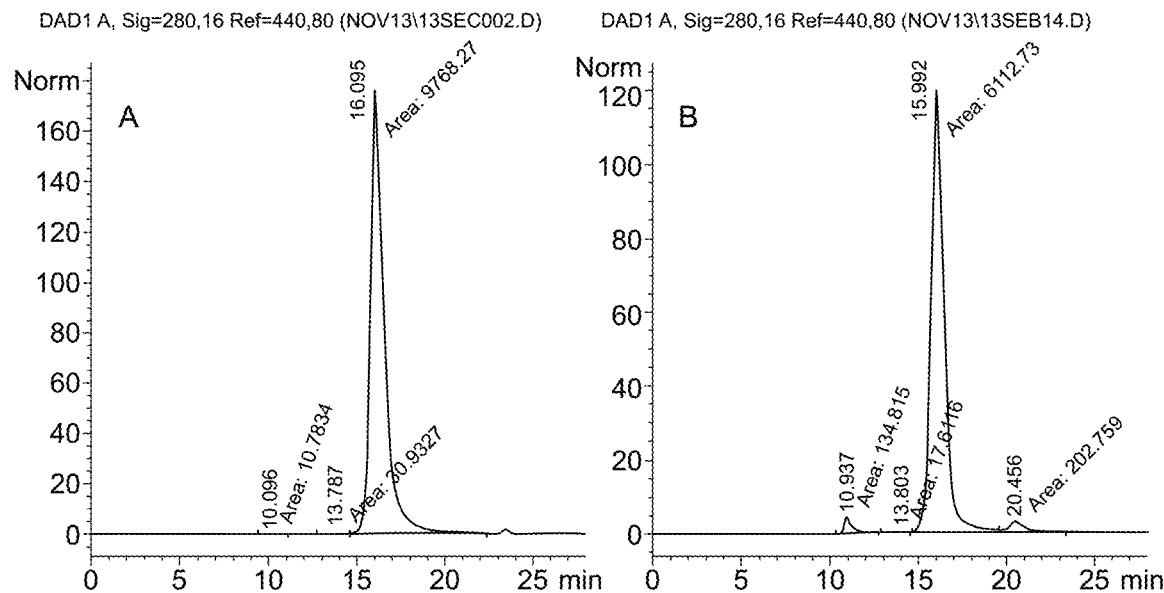
FIG. 21. Analysis of Trastuzumab-maleimide-val-cit-4-aminobenzoyl-MMAE (A) and Trastuzumab-PL13-val-cit-4-aminobenzoyl-MMAE (B) conjugates by SEC chromatography.

Results:

Trastuzumab-maleimide-val-cit-4-aminobenzoyl-MMAE is present as 99.5% monomer (see FIG. 21 (A)). Trastuzumab-PL13-val-cit-4-aminobenzoyl-MMAE is present as 93.5% monomer (see FIG. 21 (B)).

Figure 22:
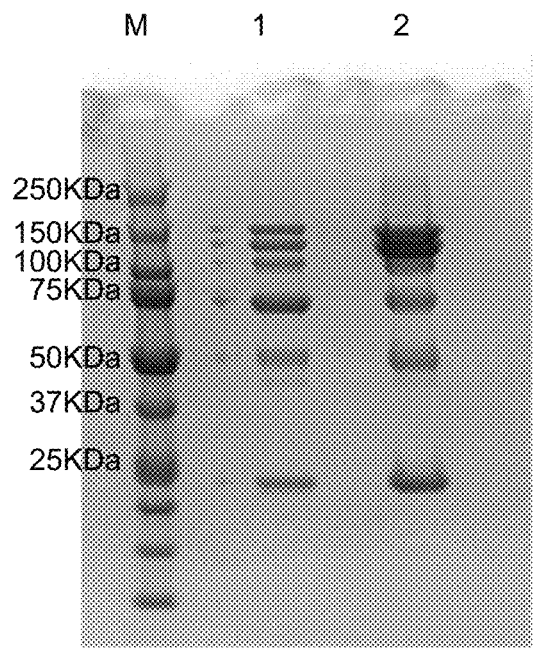
FIG. 22. Non-reducing SDS-PAGE analysis of Trastuzumab-PL13-val-cit-4-aminobenzoyl-MMAE and Trastuzumab-maleimide-val-cit-4-aminobenzoyl-MMAE.

SDS-PAGE analysis under non-reducing conditions showed the presence of multiple bands in both the trastuzumab-PL13-val-cit-4-aminobenzoyl-MMAE and Trastuzumab-maleimide-val-cit-4-aminobenzoyl-MMAE samples due to the disruption of inter-chain disulphide bonds in the antibody during alkylation of cysteine residues with linker-drug moieties (see FIG. 22). In FIG. 22, lane 1 represents the analysis of a 5 µL of sample of trastuzumab-PL13-val-cit-4-aminobenzoyl-MMAE loaded on the gel at a concentration of 1.8 mg/mL and lane 2 represents the analysis of a 5 µL of sample of trastuzumab-maleimide-val-cit-4-aminobenzoyl-MMAE loaded on the gel at a concentration of 5 mg/mL. The integrity of full length antibody is still sustained due to strong non-covalent interactions between heavy and light chains which was confirmed by SEC analysis.

7. Synthesis of PL13-NH-PEG4-OSu Heterobifunctional Linker

Figure 23:
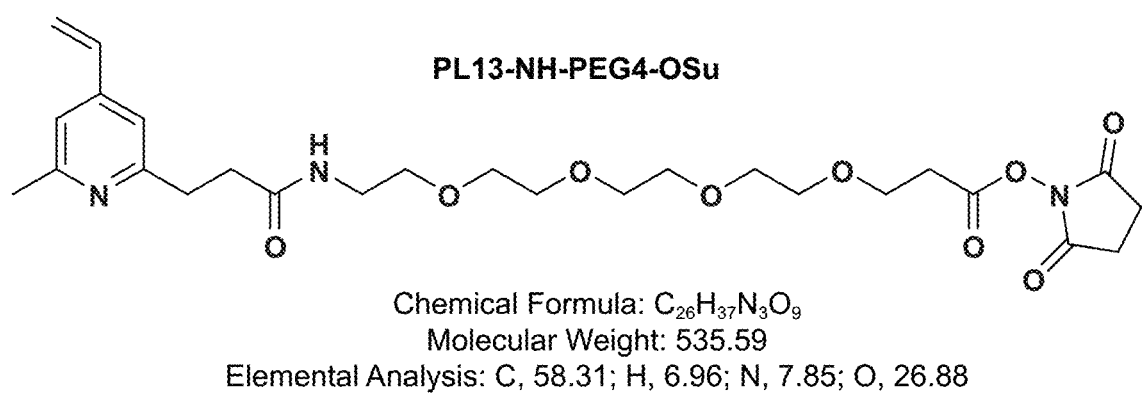
FIG. 23. Structure of PL13-NH-PEG4-OSu linker.

The hydrophilic PEG (PEG4) was introduced to the linker molecule linker arm portion, to provide PL13-NH-PEG4-OSu, to improve linker solubility over the example given under section 1 above (see FIG. 23).

Method:

PL13 free acid (as described above) was coupled to 1-Amino-3, 6, 9, 12-tetraoxapentadecan-15-oic acid. Activation of the carboxyl group to the desired succinimidyl ester was undertaken using N,N-dicyclohexylcarbodiimide (DCC) 2.5 eq./HOSu coupling in anhydrous dichloromethane (DCM). Unreacted DCC and a diisopropylurea by-product were removed via filtration from cold DCM.

Figure 24:
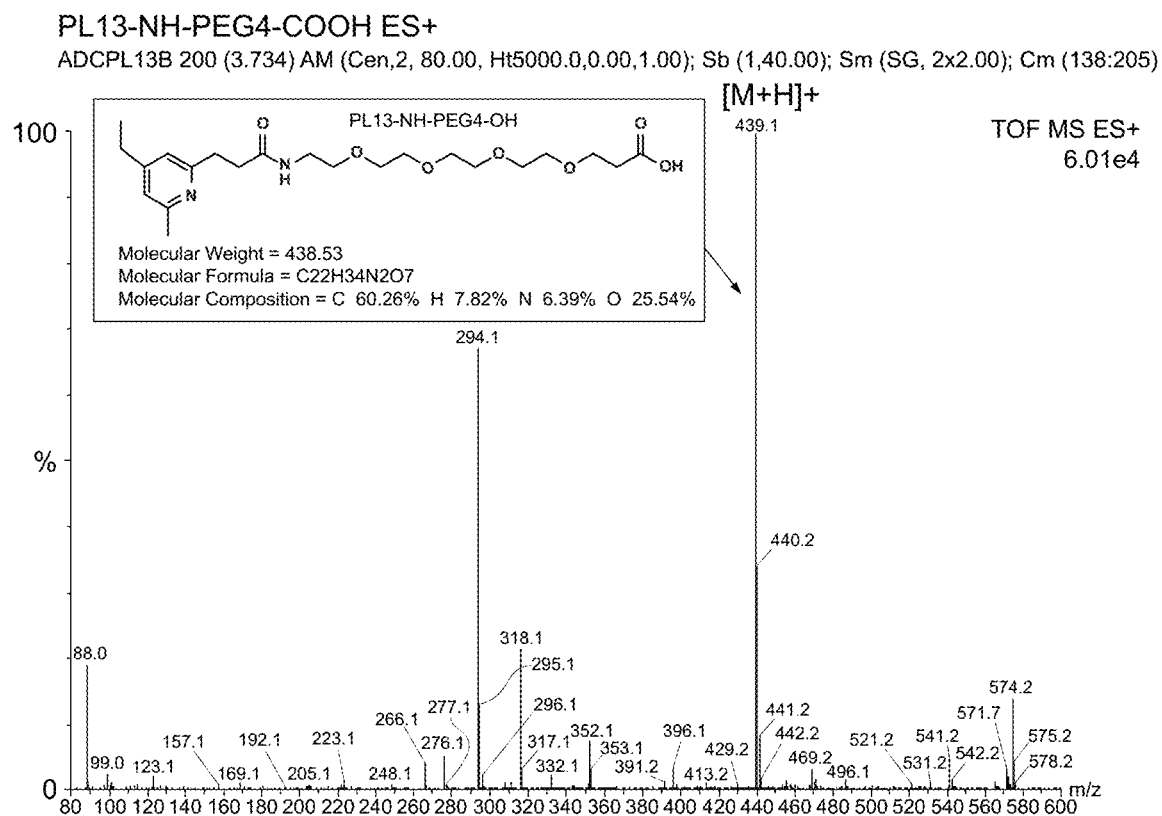
FIG. 24. ESI-MS analysis of PL13-NH-PEG4-COOH linker intermediate.

Results:

ESI-MS of PL13-NH-PEG4-COOH (see FIG. 24), confirmed the linker identity.

Comparison of Cross-reactivity of PL13-NH-PEG4-OSu and SMCC Linkers

The extent of Trastuzumab cross-linking via succinimidyl trans-4-(maleimidylmethyl)cyclohexane-1-carboxylate (SMCC), a known linker, and PL13-NH-PEG4-OSu was evaluated by reducing SDS-PAGE.

Method:

Trastuzumab at a final concentration of 2 mg/mL was incubated with 10 fold excess of SMCC or PL13-NH-PEG4-OSu. Samples were incubated at RT.

Figure 25:
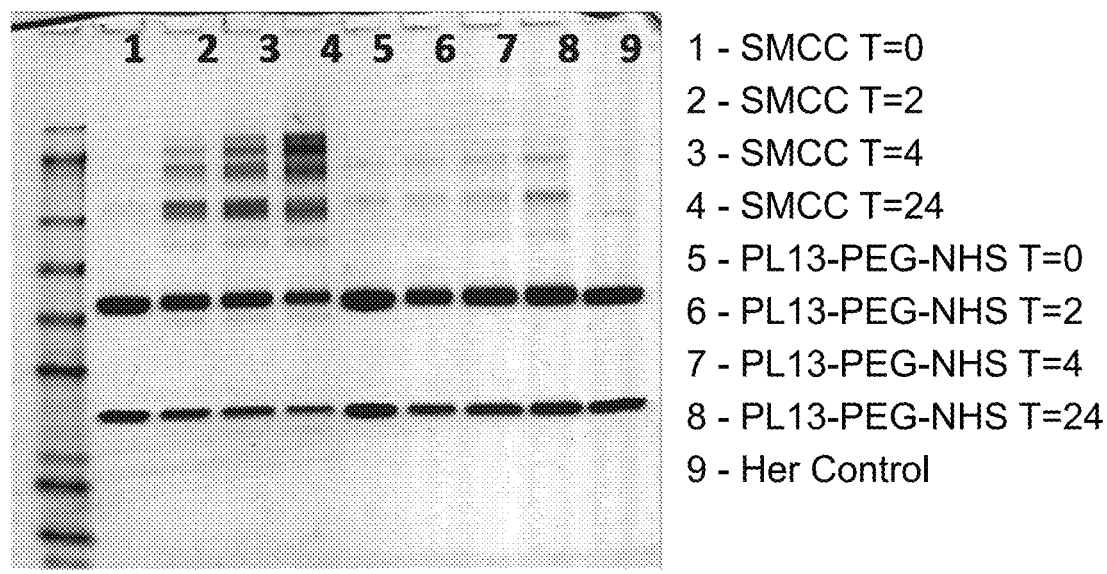
FIG. 25. Analysis of Trastuzumab cross-linking via SMCC or PL13-NH-PEG4-OSu linker by reducing SDS-PAGE.

Results:

It is evident from the SDS-PAGE that PL13-NH-PEG4-OSu shows less high molecular weight bands than the SMCC linker (see FIG. 25, lanes 5-9). There are some higher molecular weight bands on the PL13-NH-PEG4-OSu SDS-PAGE but these are present to some extent in the starting Trastuzumab lane as well (see FIG. 25, lane 5).

In contrast to the linkers of the present invention, the SMCC linker induces trastuzumab cross-linking due to non specific reactivity of the maleimide group particularly towards amine side chains of lysine residues.

8. Synthesis of PL13-NH-PEG4-val-cit-4-aminobenzoyl-MMAE

Figure 26:
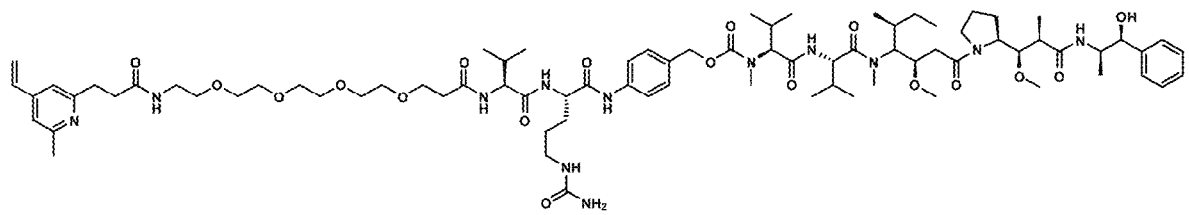
FIG. 26. Structure of PL13-NH-PEG4-val-cit-4-aminobenzoyl-MMAE linker.

To improve further the solubility of the previously synthesised PL13-val-cit-4-aminobenzoyl-MMAE cytotoxic drug linker, a short hydrophilic PEG unit was introduced to the molecule (see FIG. 26). The PEG unit also introduces a 'spacer' to the ADC linker arm, increasing the separation of the MMAE cytotoxic payload and the antibody attachment point through PL13 by some 39 atoms (versus 22 atoms previously in PL13-vcMMAE). It is believed this "spacer" should increase the rotational flexibility of the PL13 unit, which may influence the kinetics of the Michael addition to free thiol.

Method:

40 mg of crude Fmoc-val-cit-4-aminobenzoyl-MMAE was purified. The N-Fmoc group was then removed by aminolysis and the amine functionalised cytotoxic compound was purified to afford 24 mg of material. This was used to couple PL13-NH-PEG4-COOH via standard HOBt active ester chemistry.

Results:

PL13-NH-PEG4-val-cit-4-aminobenzoyl-MMAE was synthesised. This molecule represents an example of a cleavable ADC system in accordance with the present invention.

9. Conjugation of PL13-NH-PEG4-val-cit-4-aminobenzoyl-MMAE and Maleimide-val-cit-4-aminobenzoyl-MMAE to Trastuzumab.

Method:

Trastuzumab was reduced with 2.4 times excess of tris (2-carboxythyl)phosphine (TCEP) for 1 hour at RT in the presence of ethylenediaminetetraacetic acid (EDTA). The antibody was re-buffered into PBS. Trastuzumab, at a concentration of 20 mg/mL, was conjugated to 20 fold excess of PL13-NH-PEG4-val-cit-4-aminobenzoyl-MMAE in the presence of 5% v/v DMA at RT for 16 hours. Additionally, maleimide-val-cit-4-aminobenzoyl-MMAE linker was coupled to Trastuzumab (20 mg/mL) at 6 molar excess at RT for 1 hour. The ADCs obtained were analysed by HIC, PLRP and SEC chromatography.

Figure 27:
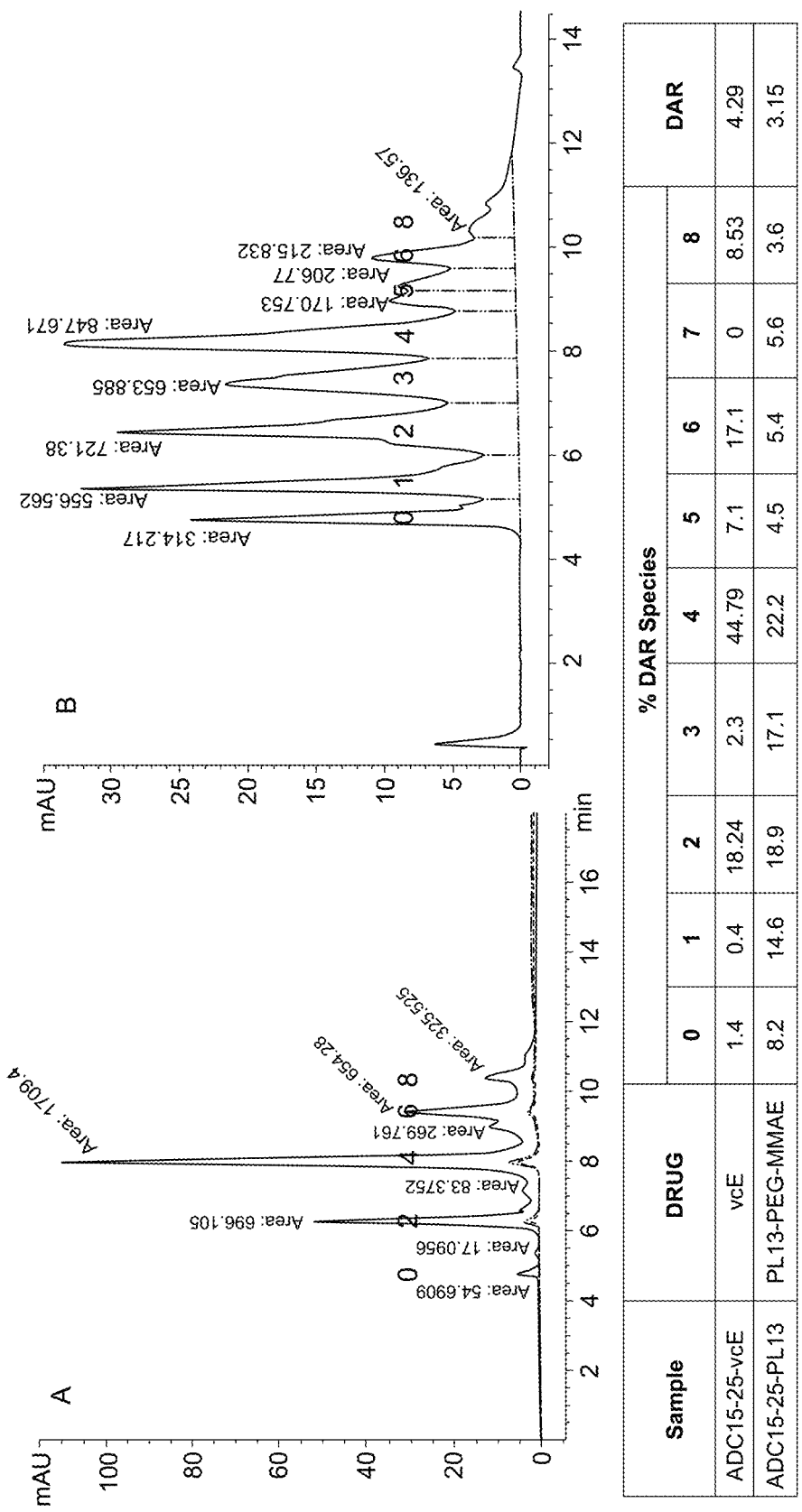
FIG. 27. HIC profile of Trastuzumab-maleimide-val-cit-4-aminobenzoyl-MMAE (A) and Trastuzumab-PL13-NH-PEG4-val-cit-4-aminobenzoyl-MMAE (B).

Results:

HIC characterisation of trastuzumab-maleimide-val-cit-4-aminobenzoyl-MMAE resulted in a DAR calculation of 4.29 (see FIG. 27 A).

HIC characterisation of trastuzumab-PL13-NH-PEG4-val-cit-4-aminobenzoyl-MMAE resulted in a DAR calculation of 3.15 (see FIG. 27 B).

In FIGS. 27A and 27B, the numbers designate the amount of drug conjugated to a full length antibody. The table represents the relative percentage of each peak area from the HIC elution profile. The average DAR is calculated by multiplying the percentage peak area by the corresponding drug load to obtain a weighted peak area. The weighted peak areas are summed and divided by 100 to give a final DAR value.

Figures 28, 29:
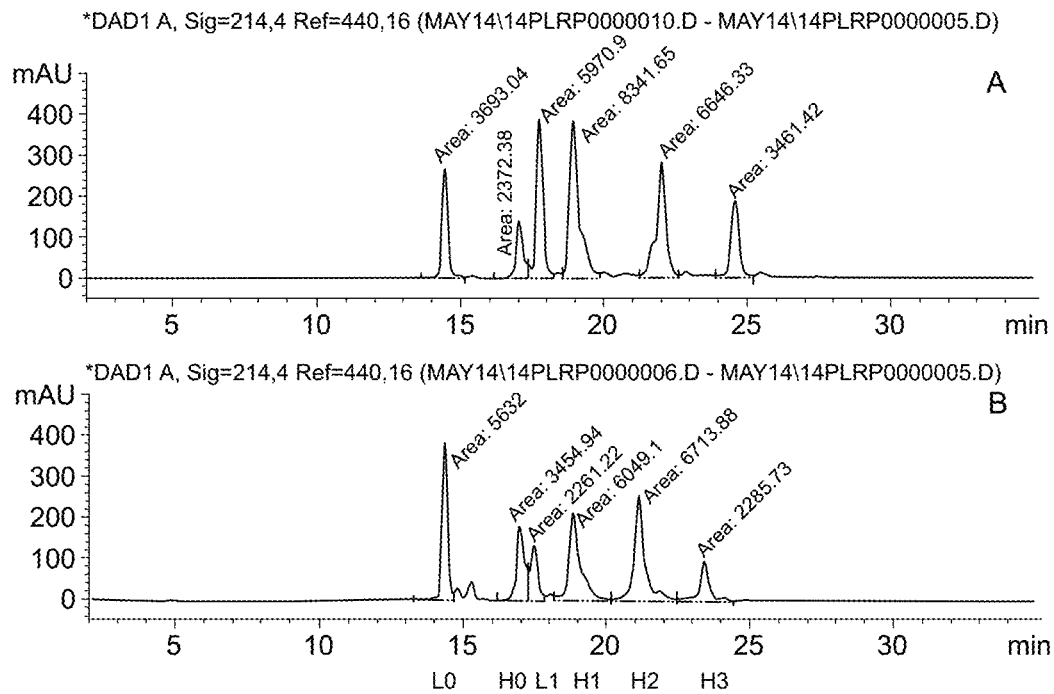
FIG. 28. PLRP profile of Trastuzumab-maleimide-val-cit-4-aminobenzoyl-MMAE (A) and Trastuzumab-PL13-NH-PEG4-val-cit-4-aminobenzoyl-MMAE (B).
FIG. 29. DAR calculation for Trastuzumab-PL13-NH-PEG4-val-cit-MMAE and Trastuzumab-mal-val-cit-MMAE based on the PLRP elution profile of FIG. 28.

DAR analysis of DTT reduced trastuzumab-maleimide-NH-PEG4-val-cit-4-aminobenzoyl-MMAE by PLRP confirmed the average drug load to be 4.3 (see FIG. 28 A and FIG. 29).

Analysis of DTT reduced trastuzumab-PL13-NH-PEG4-val-cit-4-aminobenzoyl-MMAE by PLRP confirmed an average drug load to be 3.8 (see FIG. 28 B and FIG. 29).

In FIGS. 28A and 28B, the numbers designate the amount of drug conjugated to light (L) or heavy (H) chain of the antibody.

Figure 30:
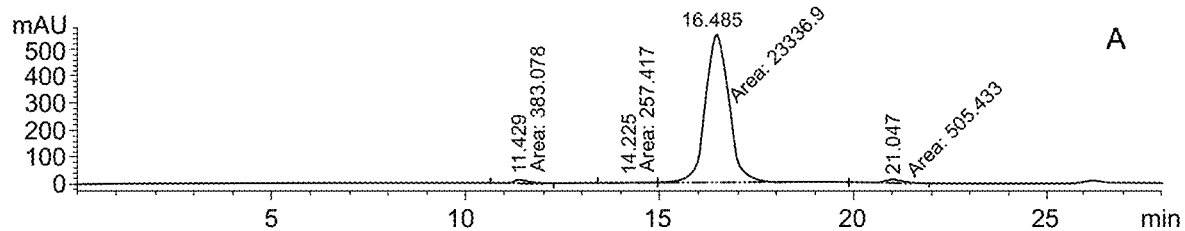
FIG. 30. SEC analysis of Trastuzumab-mal-val-cit-MMAE (A) and Trastuzumab-PL13-NH-PEG4-val-cit-MMAE (B).
Figure 30:
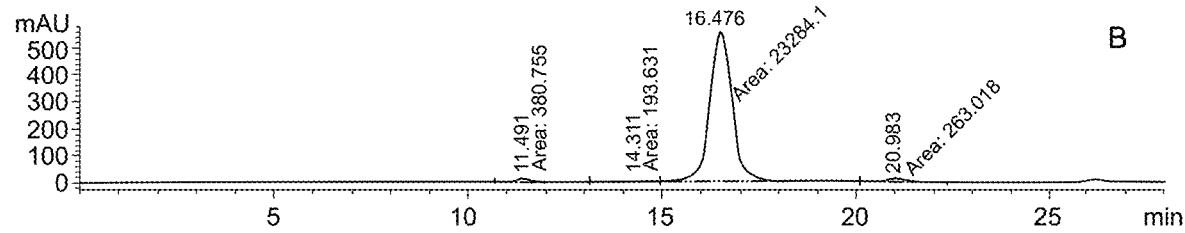

Analysis of both trastuzumab-maleimide-val-cit-4-aminobenzoyl-MMAE (HER-MAL-MMEA) and trastuzumab-PL13-NH-PEG4-val-cit-4-aminobenzoyl-MMAE (HER-PL-13-MMEA) on SEC chromatography showed that both samples are represented as monomeric species (see FIGS. 30 A and B). The table below FIGS. 30A and 30B shows the calculation of high molecular weight species (HMW), monomeric and low molecular weight species (LMVV).

Figure 31:
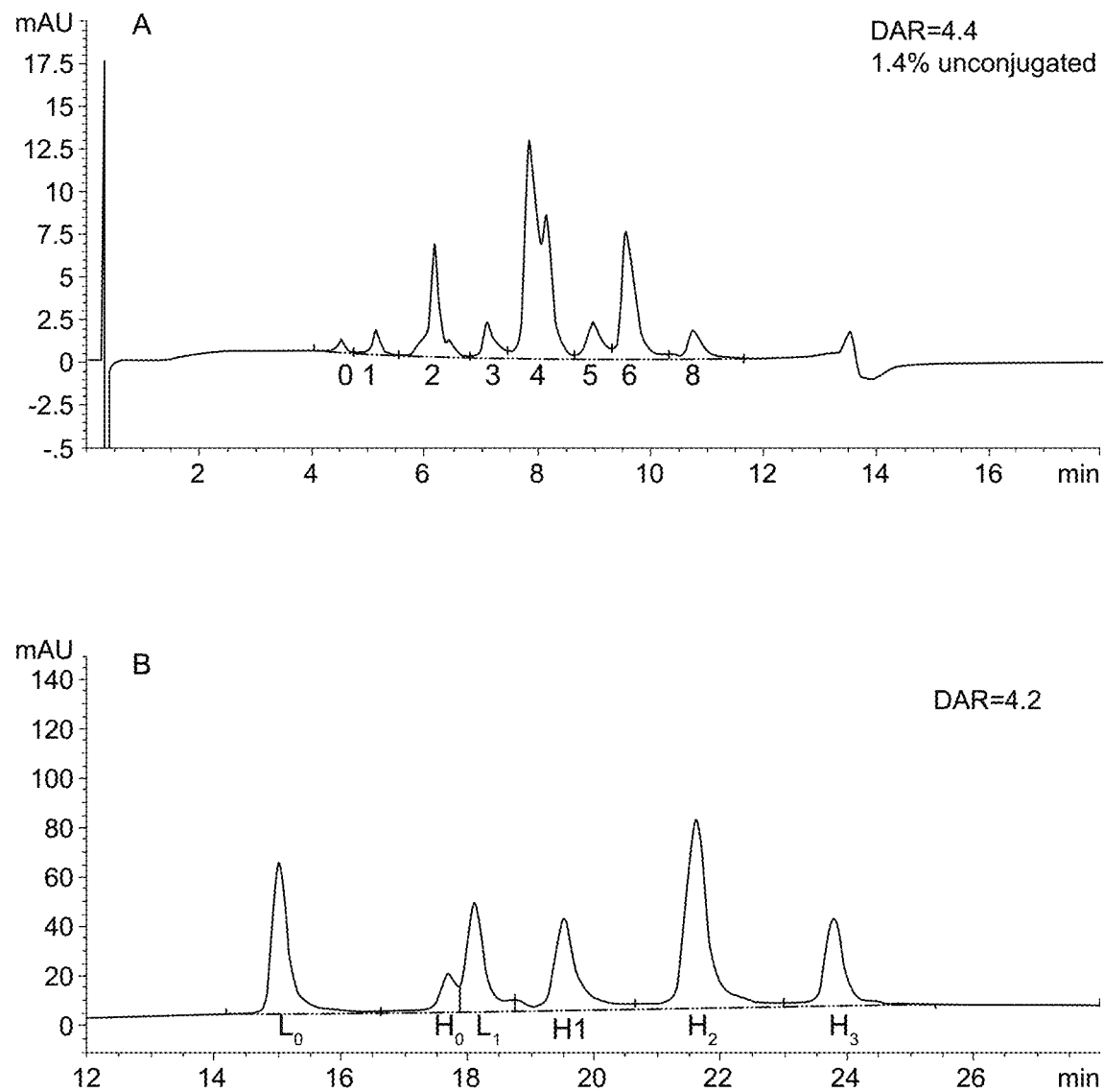
FIG. 31. Representative HIC (A) and PLRP (B) profiles of Trastuzumab-PL13-NH-PEG4-val-cit-4-aminobenzoyl-MMAE achieved after process optimisation at 1 mg scale.

10. Optimised Conditions for the Conjugation of PL13-NH-PEG4-val-cit-4-aminobenzoyl-MMAE Method:

Trastuzumab (23.5 mg/mL) was reduced with 2.4 equivalents of TCEP for 2 hours at RT to yield an average of 4.5 free thiols. The reduced Trastuzumab was conjugated to 20 fold excess of PL13-NH-PEG4-val-cit-MMAE in the presence of 10% v/v DMA at 30° C. for 18 hours. The conjugate was analysed by HIC and PLRP chromatography (see FIGS. 31 A and B).

Results:

The HIC and PLRP data show a substantial improvement in conjugation efficiency. The higher level of conjugation efficiency has also resulted in a significant reduction in the level of 'odd' DAR species and a reduction in the level of unconjugated antibody.

11. Conjugation of Trastuzumab-PL13-NH-PEG4-val-cit-aminobenzoyl-MMAE (A) and Trastuzumab-maleimideval-cit-aminobenzoyl-MMAE (B) at 150 mg Scale, Demonstrating Scalability of the Process Method:

Trastuzumab (24.53 mg/mL) was reduced with 2.1 equivalents of TCEP for 2 hours at RT. The reduced Trastuzumab was conjugated to 20 fold excess of PL13-NH-PEG4-val-cit-MMAE in the presence of 10% v/v DMA at 30° C. for 18 hours.

Trastuzumab at concentration of 25.68 mg/ml was reduced with 1.95 equivalents of TCEP for 2 hours at RT. The reduced Trastuzumab was conjugated to 6 fold excess of maleimide-val-cit-MMAE in the presence of 10% v/v DMA at RT for 1 hour.

Figure 32:
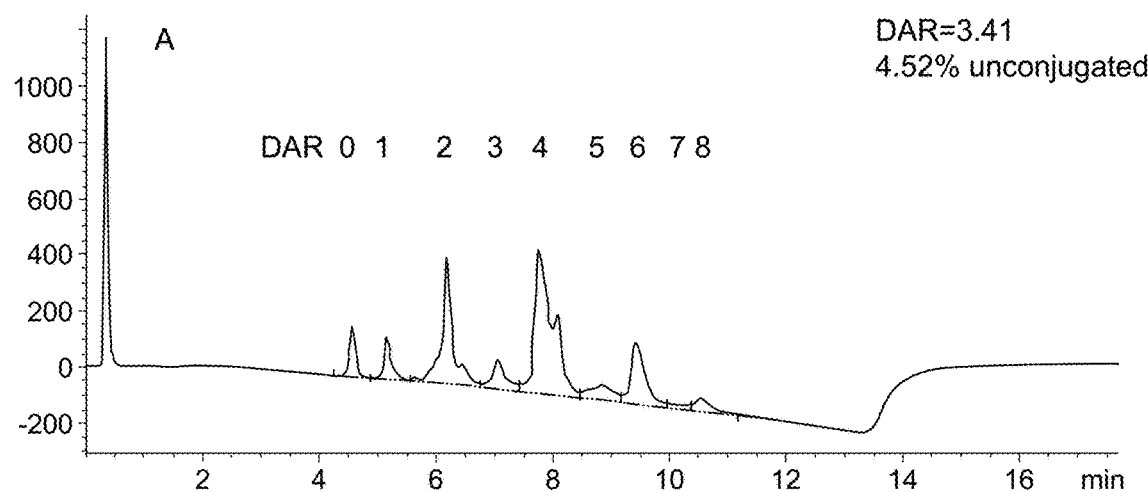
FIG. 32. HIC profiles of Trastuzumab-PL13-NH-PEG4-val-cit-4-aminobenzoyl-MMAE (A) and Trastuzumab-maleimide-val-cit-4-aminobenzoyl-MMAE (B) achieved at 150 mg scale.
Figure 32:
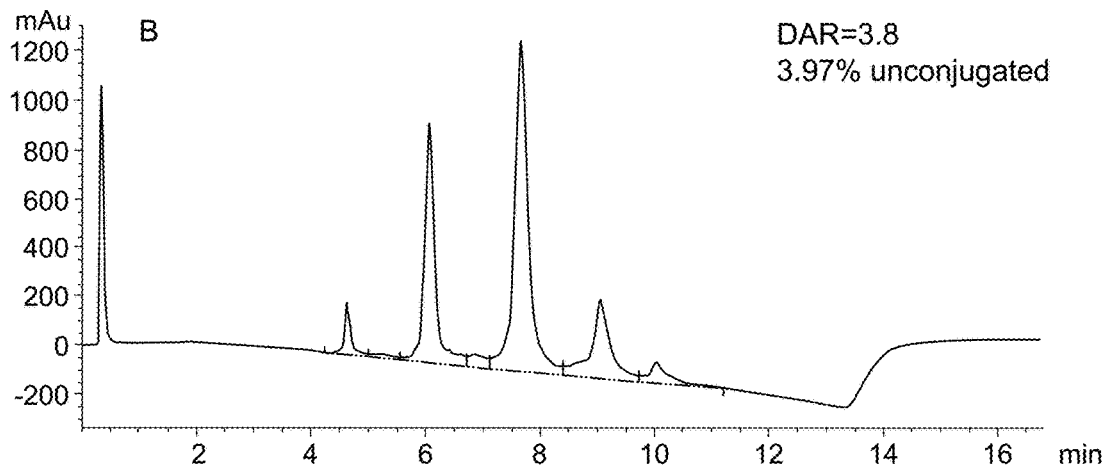
Figure 33:
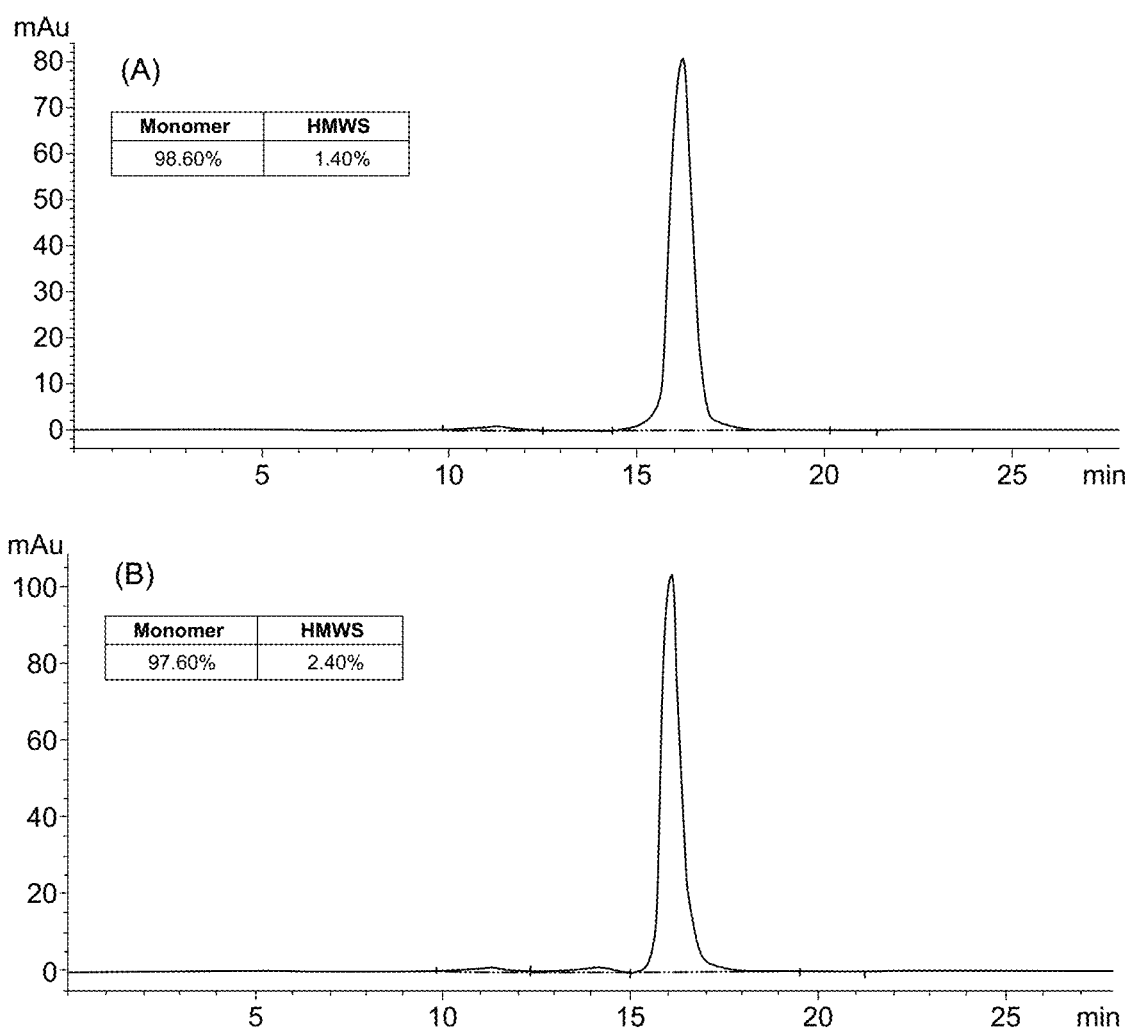
FIG. 33. SEC profiles of Trastuzumab-PL13-NH-PEG4-val-cit-aminobenzoyl-MMAE (A) and Trastuzumab-maleimide-val-cit-aminobenzoyl-MMAE (B) achieved at 150 mg scale.

The conjugates were analysed by HIC and SEC chromatography (see FIGS. 32 and 33).

Results:

The HIC profiles showed similar conjugation efficiency for Trastuzumab-PL13-NH-PEG4-val-cit-aminobenzoyl-MMAE (FIG. 32A) and Trastuzumab-maleimide-val-cit-aminobenzoyl-MMAE (FIG. 32B). SEC (FIGS. 33A and 33B) confirmed that both conjugates are monomers with only a small amount of high molecular weight species present (1.4-2.4%). This demonstrates the scalability of the conjugation process developed using the linkers of the present invention.

12. Conjugation of PL13-NH-PEG4-val-cit-aminobenzoyl-MMAE to Thiomab, Demonstrating Successful Conjugation to Engineered Trastuzumab (Thiomab)

Method:

Trastuzumab with a cysteine mutation (V205C) introduced in the antibody light chain was conjugated at concentration of 10 mg/ml to 40 fold excess of PL13-NH-PEG4-val-cit-MMAE in the presence of 10% DMA in buffer pH 7.4. Conjugation reactions were incubated at 35° C. for 48 hours.

Figure 34:
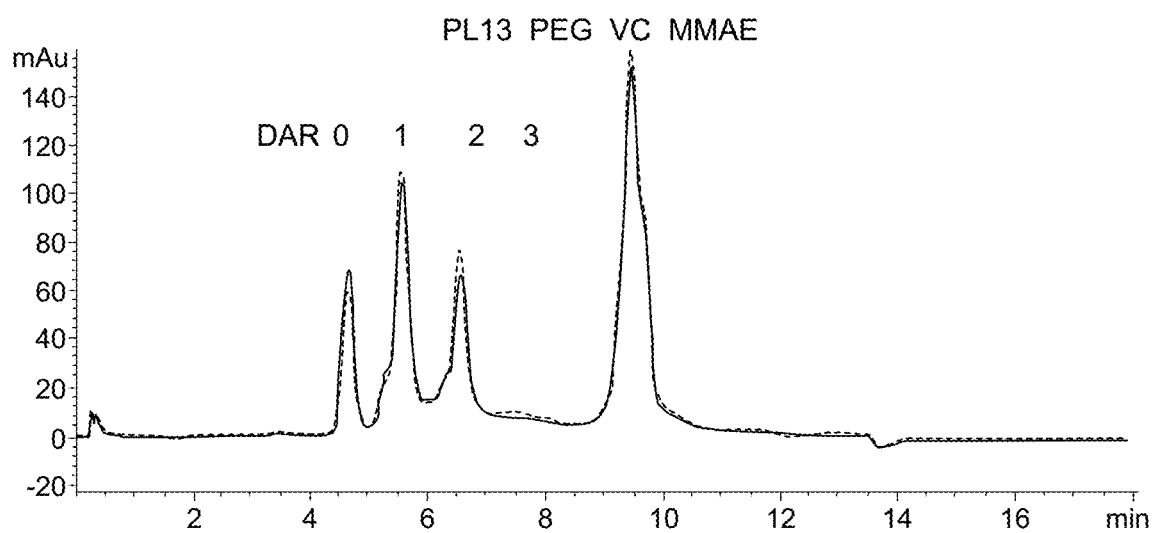
FIG. 34. HIC profile of Thiomab-PL13-NH-PEG4-val-cit-MMAE at pH 7.0 (solid line) and pH 7.5 (dashed line).

Results:

The HIC profile of Trastuzumab (V2015C)-PL13-NH-PEG4-val-cit-MMAE demonstrates that PL13 can be successfully conjugated to antibodies with engineered Cys residues at both pHs (FIG. 34). The rate and extent of the conjugation reaction appears to be influenced by the thiol microenvironment.

13. Utility of ADCs According to the Present Invention as ADCs.

ADC conjugation products, as described above in section 8, were further subjected to in vivo and in vitro testing to demonstrate their utility as commercial ADCs.

In Vitro Stability of Trastuzumab-malemide-val-cit-4-aminobenzoyl-MMAE and Trastuzumab-PL13-NH-PEG4-val-cit-4-aminobenzoyl-MMAE in the Presence of NAC Method:

Stability of drug-linker for the trastuzumab-malemide-val-cit-4-aminobenzoyl-MMAE and trastuzumab-PL13-NH-PEG4-val-cit-4-aminobenzoyl-MMAE conjugates was evaluated in the presence of NAC in PBS buffer.

Figure 35:
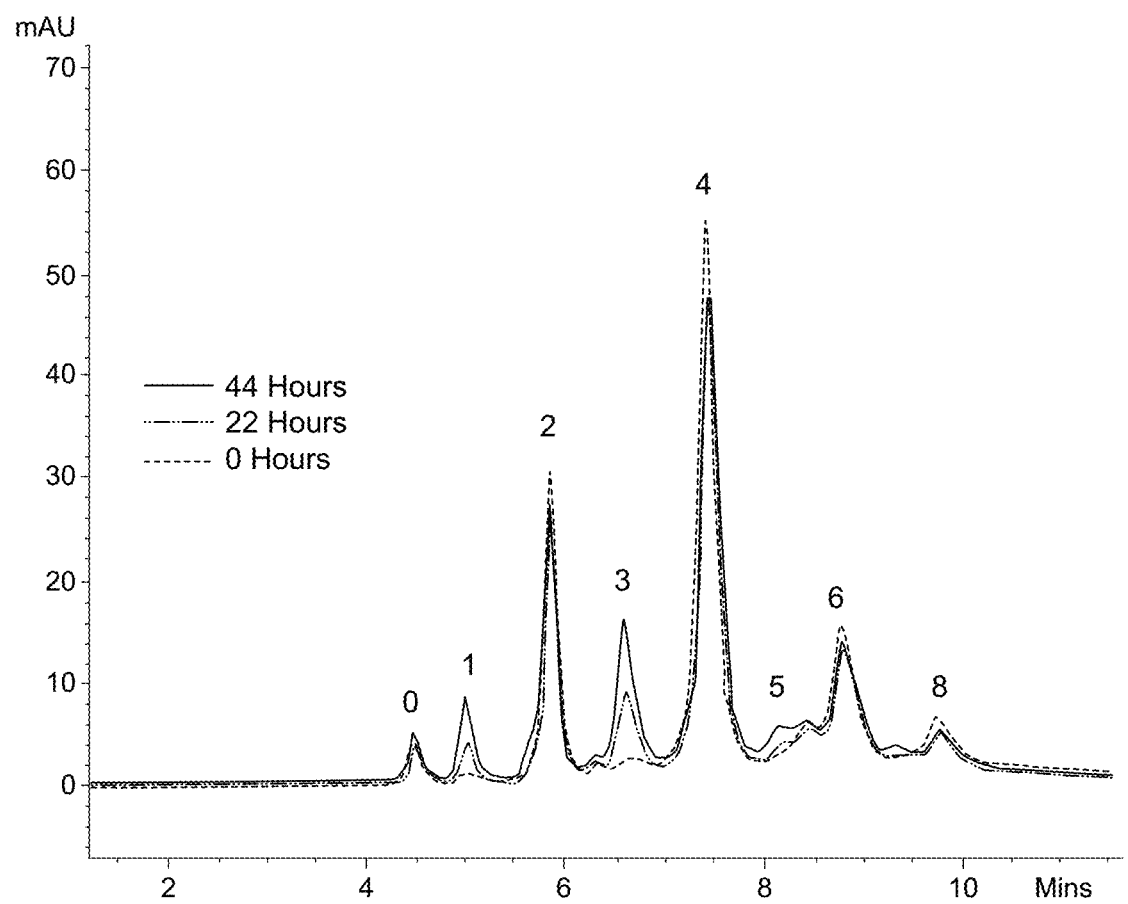
FIG. 35. PLRP profile to demonstrate de-drugging for trastuzumab-malemide-val-cit-4-aminobenzoyl-MMAE.
Figure 36:
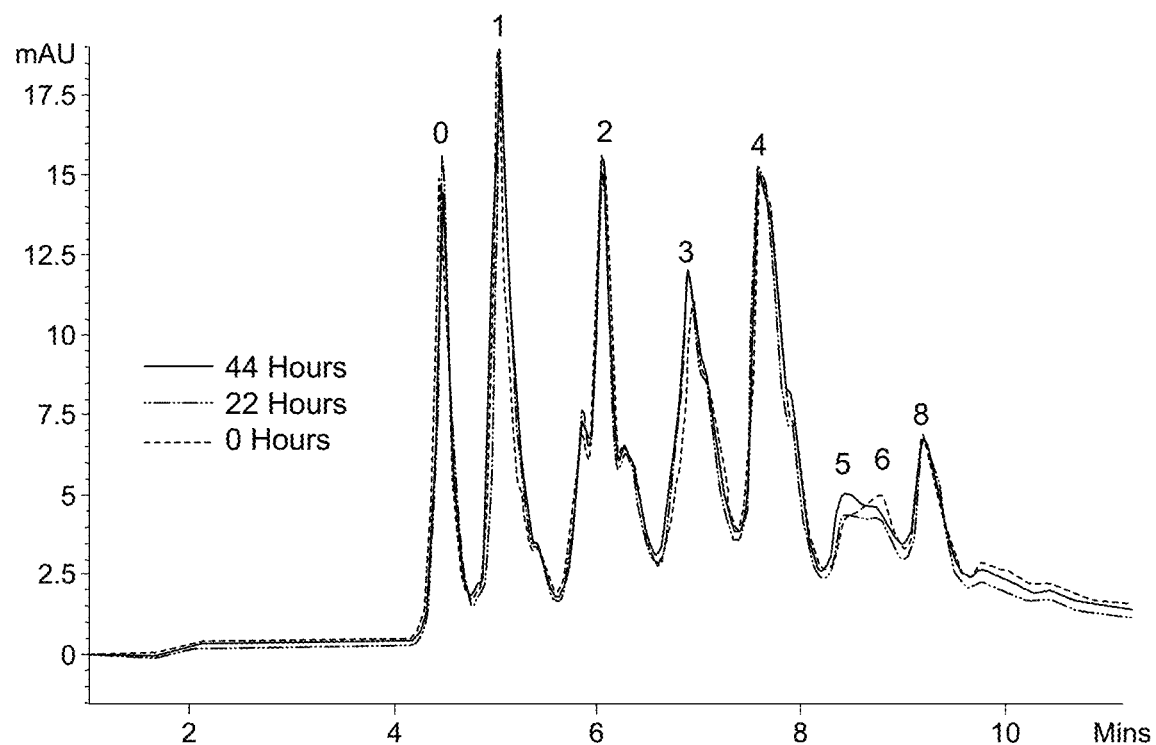
FIG. 36. PLRP profile to demonstrate de-drugging for trastuzumab-PL13-NH-PEG4-val-cit-4-aminobenzoyl-MMAE with a DAR of 3.8.

Results:

The trastuzumab-PL13-NH-PEG4-val-cit-4-aminobenzoyl-MMAE conjugate was not influenced by the presence of NAC in the buffer (FIG. 36). Trastuzumab-maleimide-val-cit-4-aminobenzoyl-MMAE showed decreased stability in the presence of NAC (see FIG. 35). FIG. 36 in particular demonstrates there is no profile change for the PL13 containing ADC resulting from challenge from free thiol, indicating stability of the construct.

In Vitro Stability of Trastuzumab-malemide-val-cit-4-aminobenzoyl-MMAE and Trastuzumab-PL13-NH-PEG4-val-cit-4-aminobenzoyl-MMAE in Mouse Plasma The in vitro serum stability of the ADCs Trastuzumab-PL13-NH-PEG4-val-cit-aminobenzoyl-MMAE and Trastuzumab-maleimide-val-cit-aminobenzoyl-MMAE was compared in mouse plasma.

Method:

Trastuzumab-PL13-NH-PEG4-val-cit-aminobenzoyl-MMAE and Trastuzumab-maleimide-val-cit-aminobenzoyl-MMAE were separately spiked into filtered athymic nude mouse plasma to a concentration of 0.2 mg/mL. The solutions were mixed and triplicate aliquots of 50 µL were taken and snap frozen in liquid nitrogen (time point—0 h). The plasma solutions of the ADCs were incubated at 37° C. for 7 days. Aliquots of 50 µL were pulled in triplicate for each time point: 1, 2, 3, 4, 5, 6 and 7 days, and stored at −80° C. until analysis.

Results:

ADC stability was monitored by LC-ESI/MS analysis. Plasma samples were pre-purified and trypsin/CNBr digested before MS analysis. Four non-conjugated peptides (two from heavy chain and two from light chain) and two conjugated peptides (one from heavy chain and one from light chain) were selected to monitor the stability of the ADCs. Averaged data from non-conjugated peptides correspond to the stability of the antibody component in mouse plasma (Total-Ab) and data from conjugated peptides show the stability of the ADC conjugate (LC conjugated, HC conjugated peptide).

Figure 37:
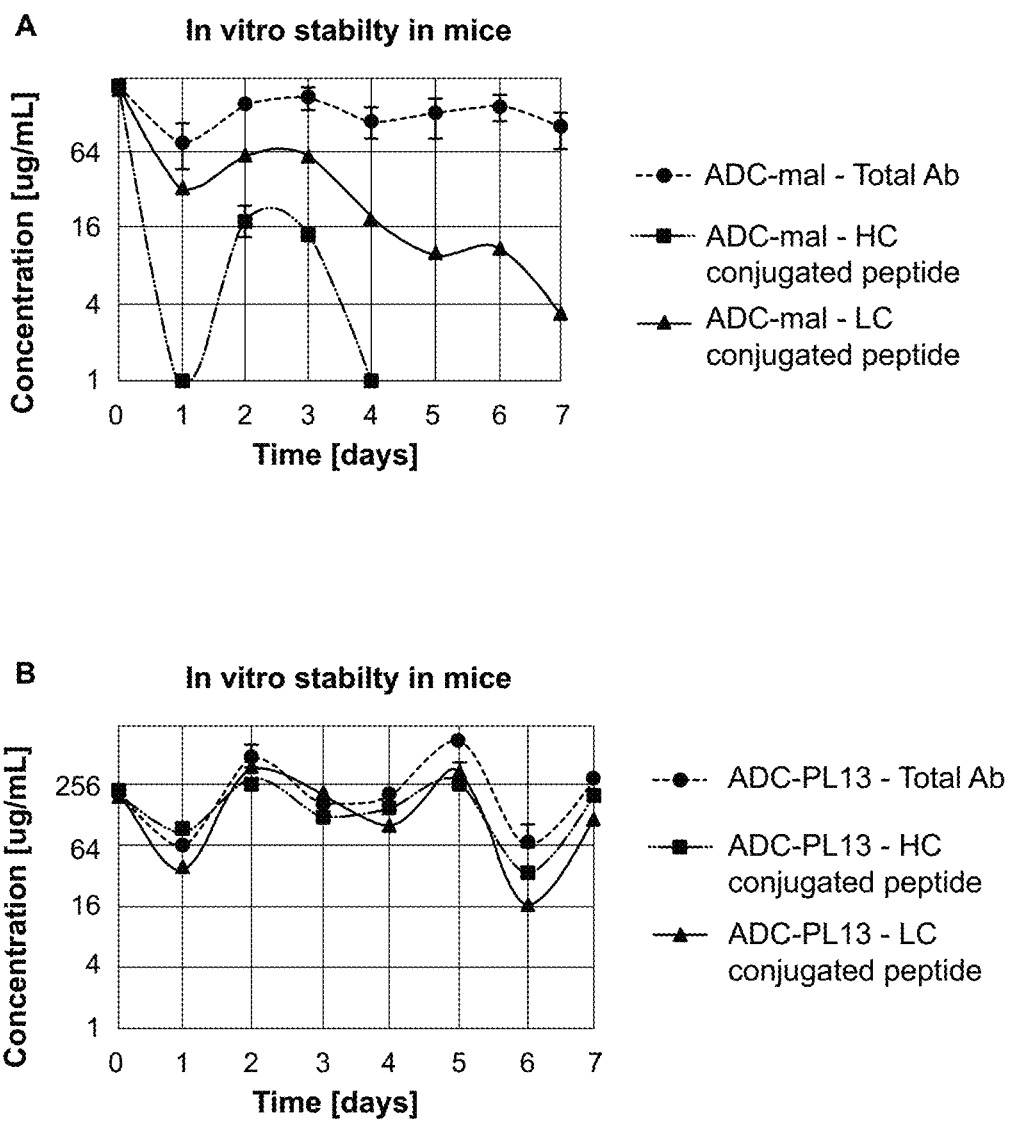
FIG. 37. In vitro stability of ADCs: trastuzumab-maleimide-val-cit-4-aminobenzoyl-MMAE, Mal-ADC (A) vs trastuzumab-PL13-NH-PEG4-val-cit-4-aminobenzoyl-MMAE, PL13-ADC (B)

This in vitro data revealed that Trastuzumab-maleimide-val-cit-aminobenzoyl-MMAE undergoes de-drugging at both the light chain and heavy chain, whereas the antibody component is stable (FIG. 37A). Loss of drug from the heavy chain peptide was more rapid when compared to the light chain peptide, indicating that the rate of drug loss is affected by the conjugation site.

The Trastuzumab-PL13-NH-PEG4-val-cit-aminobenzoyl-MMAE conjugate retained MMAE drug throughout the 7 day incubation period, showing that PL13 confers stability to both conjugation sites (FIG. 37B). The observed variability for both conjugates is due to efficiency of sample recovery for the ESI-MS method applied for sample analysis.

In Vivo Stability of Trastuzumab-malemide-val-cit-4-aminobenzoyl-MMAE and Trastuzumab-PL13-NH-PEG4-val-cit-4-aminobenzoyl-MMAE in Mice Method:

In vivo stability was evaluated in mice injected with 5 mg/kg of the trastuzumab-malemide-val-cit-4-aminobenzoyl-MMAE and trastuzumab-PL13-NH-PEG4-val-cit-4-aminobenzoyl-MMAE conjugates. Plasma samples were pre-purified and trypsin/CNBr digested before LC-MS analysis. Two conjugated peptides (one from heavy chain and one from light chain) were selected to monitor the stability of the ADCs.

Figure 38:
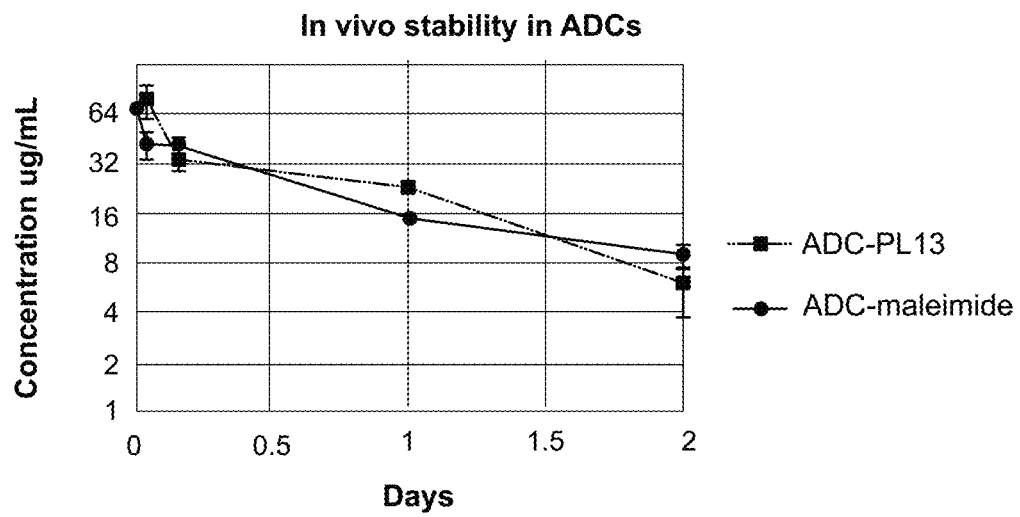
FIG. 38. In vivo stability of ADCs: PL13-ADC vs Mal-ADC

Results:

The stability of conjugated peptides is a result of two events; 1) catabolic degradation of ADCs and 2) loss of drug due to linker instability. Conjugated peptides derived from trastuzumab-PL13-NH-PEG4-val-cit-4-aminobenzoyl-MMAE show better stability at 1 day in mouse plasma than peptides derived from trastuzumab-malemide-val-cit-4-aminobenzoyl-MMAE. The observed difference is likely due to more rapid drug loss from conjugated peptides derived from trastuzumab-malemide-val-cit-4-aminobenzoyl-MMAE than from trastuzumab-PL13-NH-PEG4-val-cit-4-aminobenzoyl-MMAE which is consistent with the in vitro mouse plasma data, showing rapid de-drugging for trastuzumab-malemide-val-cit-4-aminobenzoyl-MMAE within the first four days of incubation (FIG. 38); approximately 70% of the drug attached to the light chain and 90% of the drug on the heavy chain was lost within the first two days. In contrast, trastuzumab-PL13-NH-PEG4-val-cit-4-aminobenzoyl-MMAE retains more drug due to the linker stability over a longer period of time.

Figure 39A:
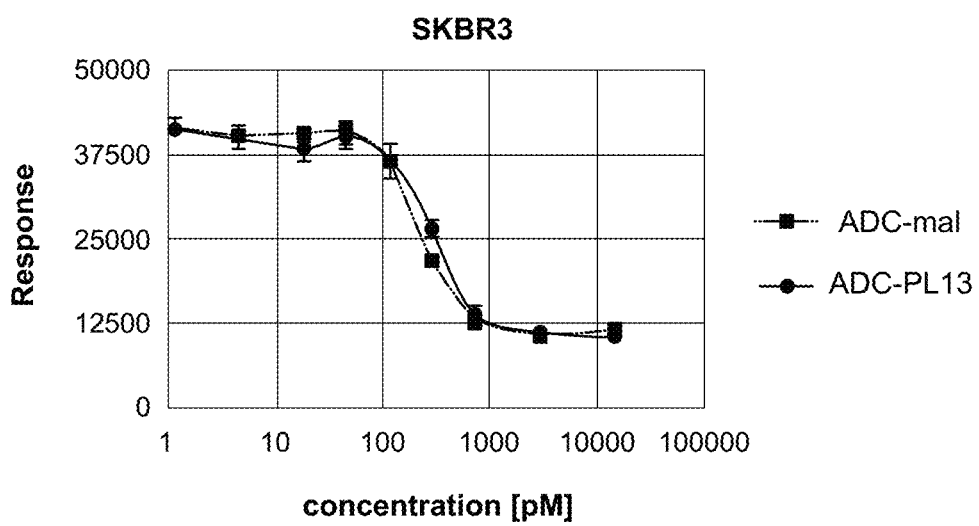
FIG. 39. Cell kill data for SKBR3 cell line (A), BT474 cell line (B) and JIMT-1 cell line (C).
Figure 39B:
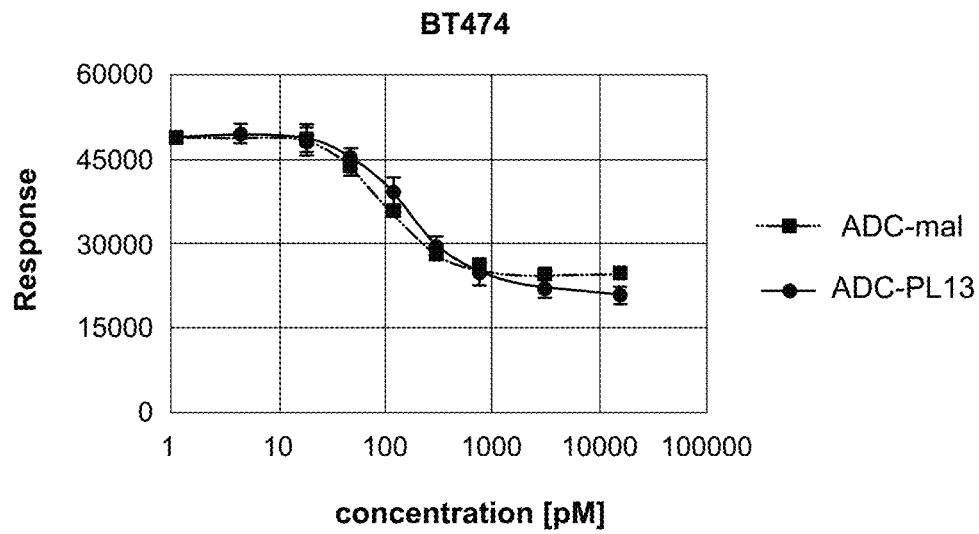
Figure 39C:
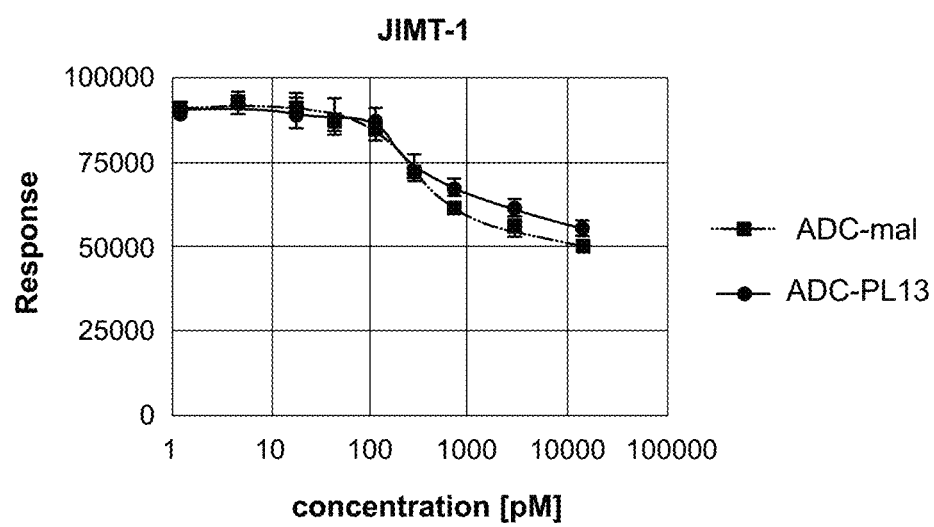

In Vitro Stability of Trastuzumab-malemide-val-cit-4-aminobenzoyl-MMAE and Trastuzumab-PL13-NH-PEG4-val-cit-4-aminobenzoyl-MMAE in Various Cell Lines In FIGS. 39A to 39C SKBR3, BT747 and JIMT-1 cell kill data are shown for the ADCs described above. The SKBR3, BT747 and JIMT-1 cell lines were selected in this test, as they are known to express the Her2 receptor. Additionally, the JIMT-1 cell line is known to be resistant to trastuzumab. In FIGS. 39A to 39C "ADC mal" relates to trastuzumab-maleimide-val-cit-4-aminobenzoyl-MMAE, and "ADC-PL13" relates to trastuzumab-PL13-NH-PEG4-val-cit-4-aminobenzoyl-MMAE. Relative in vitro activities of tested conjugates against three cell lines indicate the data for the trastuzumab-PL13-NH-PEG4-val-cit-4-aminobenzoyl-MMAE are comparable to the trastuzumab-maleimide-val-cit-4-aminobenzoyl-MMAE. Accordingly, this data shows that the ADC of the present invention is active and so the presence of PL13 does not have a negative effect on cell killing.

Figure 40:
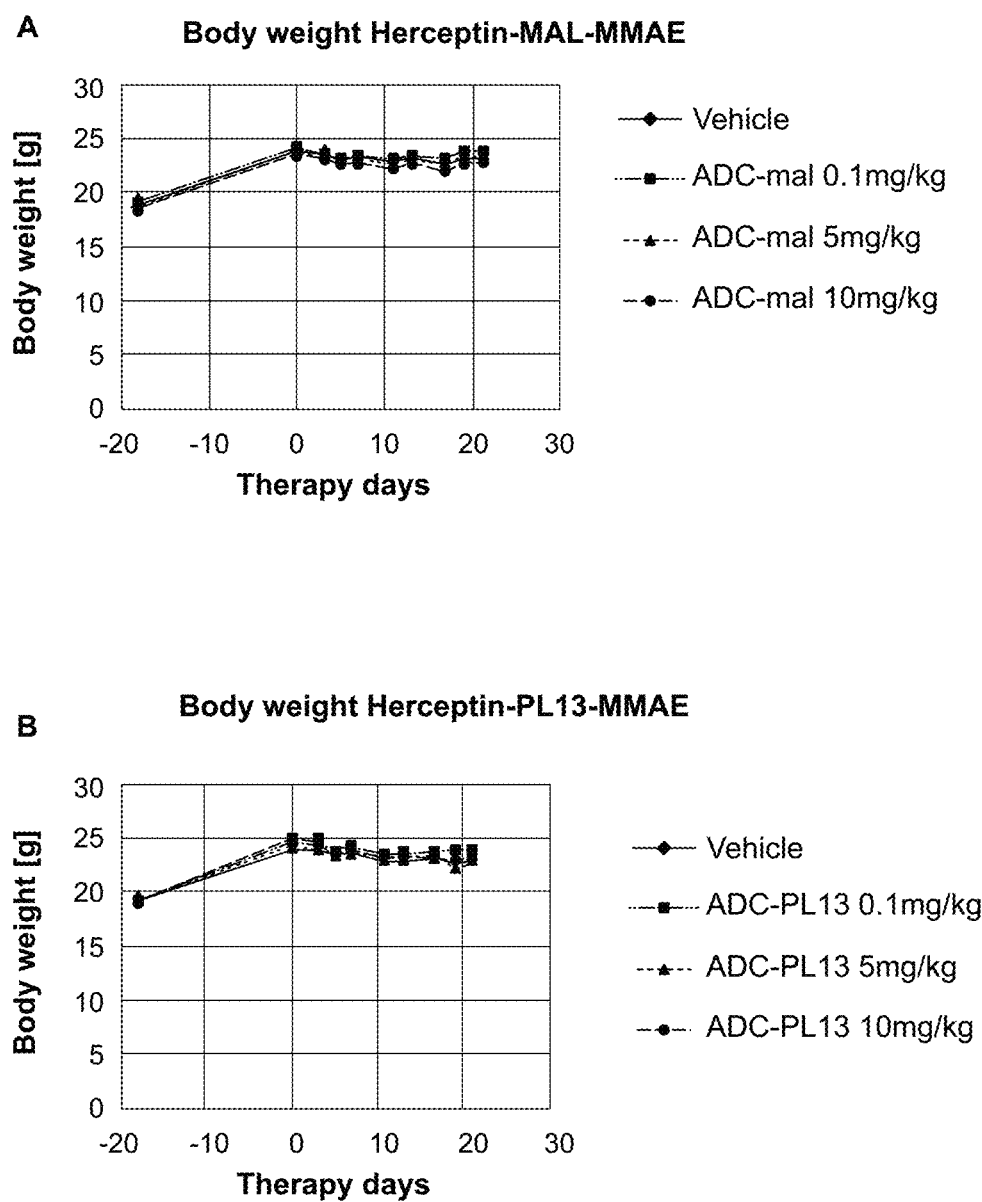
FIG. 40. Multi-dose xenograft data to demonstrate ADC toxicity.
Figure 41:
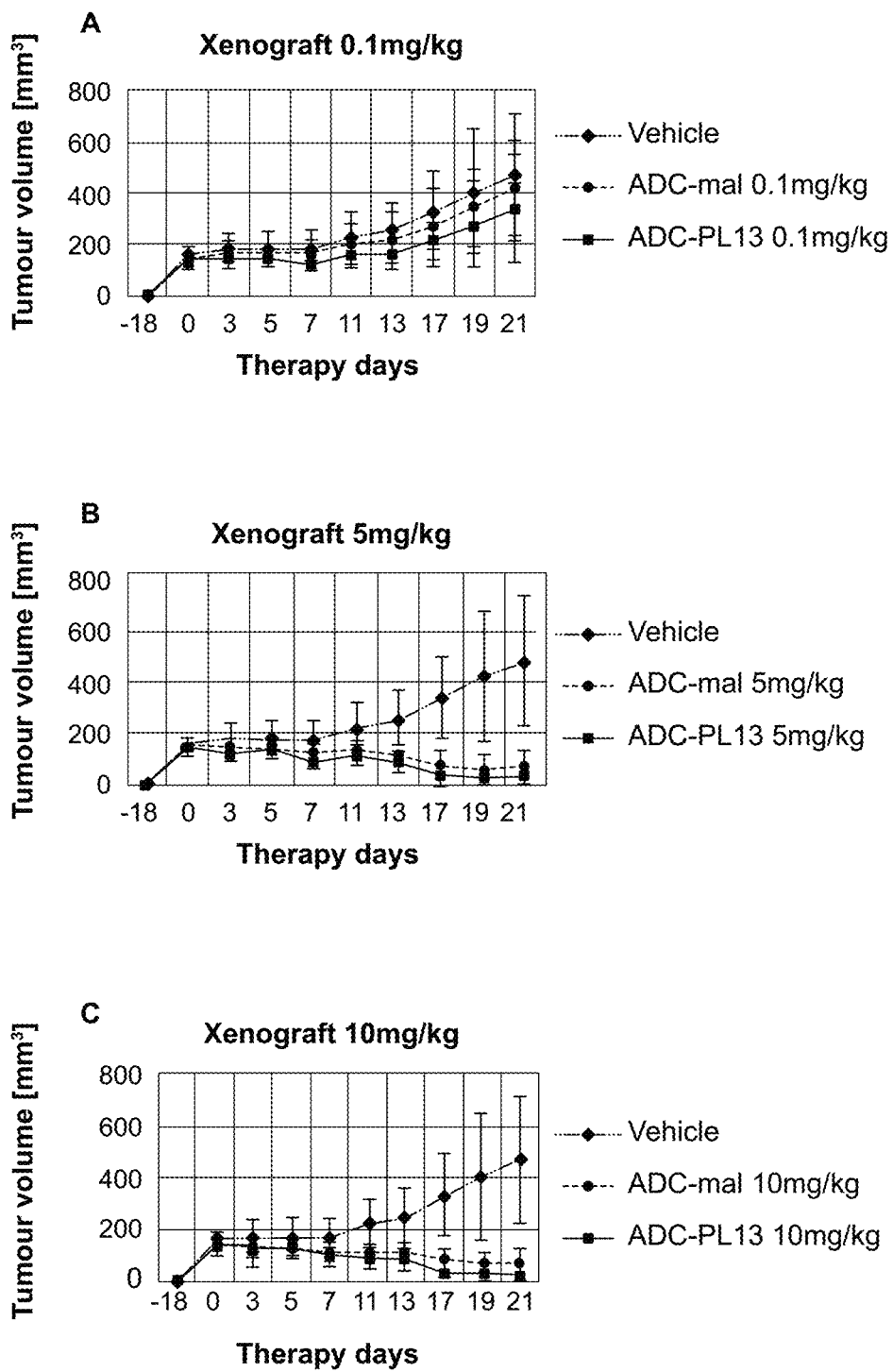
FIG. 41. Multi-dose xenograft data to show ADC effect on tumour growth.
Figure 42:
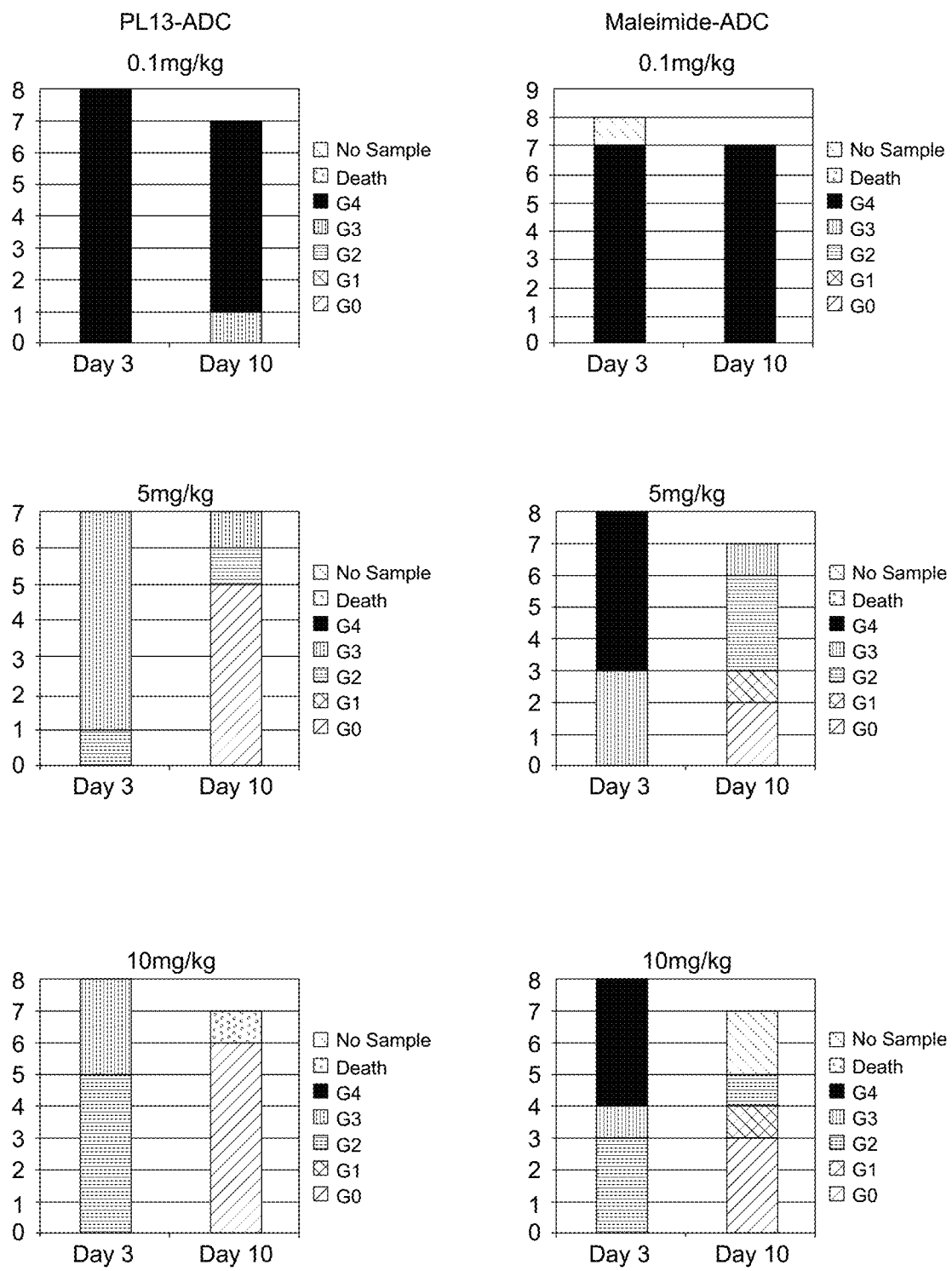
FIG. 42. Tumour maturity histopathology data

In Vivo Stability of Trastuzumab-malemide-val-cit-4-aminobenzoyl-MMAE and Trastuzumab-PL13-NH-PEG4-val-cit-4-aminobenzoyl-MMAE in Mice Exhibiting Breast Cancer Cell Tumours Xenograft data is shown in FIGS. 40, 41 and 42 in relation to the effect of the ADCs on mice exhibiting breast cancer cell tumours. The breast cancer cell line utilised was BT474 (Her2 expresser, with high susceptibility to trastuzumab).

Mouse weight is used (as shown in FIG. 40) to measure the toxicity of the ADC in vivo. It can be seen from the data obtained that the trastuzumab-maleimide-val-cit-4-aminobenzoyl-MMAE (ADC-mal) (FIG. 40A) and the trastuzumab-PL13-NH-PEG4-val-cit-4-aminobenzoyl-MMAE (ADC-PL13) (FIG. 40B) have a negligible effect on mouse weight over the course of the therapy period. This is indicative of the ADCs of the present invention being of suitable toxicity levels for use commercially.

FIG. 41 shows the effectiveness of the tested ADCs at three doses (0.1, 5 and 10 mg/kg) on tumour growth over a 21 day therapy period. Tumour growth was determined by changes in tumour volumes. Mice treated with both compounds at 0.1 mg/kg experienced tumour growth delay relative to the untreated group. In contrast, all of the animals dosed with the trastuzumab-maleimide-val-cit-4-aminobenzoyl-MMAE (ADC-mal) and the trastuzumab-PL13-NH-PEG4-val-cit-4-aminobenzoyl-MMAE (ADC-PL13) at 5 and 10 mg/kg showed complete responses over the therapy period.

FIG. 42 shows the effectiveness of the tested ADCs at three doses (0.1, 5 and 10 mg/kg) on tumour maturity histological phenotype over a 10 day therapy period. Tumour tissues were examined microscopically after haematoxylin and eosin staining and graded as follows:

0: no xenograft mass; occasionally, isolated tumour cells in sub-cutis or fat tissue
1: small fragmented mass; incomplete epithelial development sequence
2: xenograft showing marked cell loss
3: zonal cell loss with areas of mature tumour
4: intact xenograft mass showing full epithelial development sequence and associated pathology No reduction in the tumour maturity was observed for either trastuzumab-PL13-NH-PEG4-val-cit-4-aminobenzoyl-MMAE (ADC-PL13) or trastuzumab-maleimide-val-cit-4-aminobenzoyl-MMAE (ADC-mal) dosed at 0.1 mg/kg, with no significant differences observed between the two ADCs. However, trastuzumab-PL13-NH-PEG4-val-cit-4-aminobenzoyl-MMAE dosed at 5 and 10 mg/kg revealed significantly reduced tumour maturity starting at days 3 (grade 3 and grade 3/2, respectively). This effect was more pronounced at day 10 (grade 1 for 5 mg/kg and grade 1/0 for 10 mg/kg) with some samples showing no tumour mass. The trastuzumab-maleimide-val-cit-4-aminobenzoyl-MMAE dosed at 5 and 10 mg/kg reduced tumour maturity (grade 4/3 and grade 4/3/2, respectively) starting at 3 days, but the effects were less pronounced in comparison with animals dosed at corresponding doses of trastuzumab-PL13-NH-PEG4-val-cit-4-aminobenzoyl-MMAE at 3 days. Furthermore, there was a markedly greater tumour heterogeneity for ADC-mal than observed for ADC-PL13 for 5 and 10 mg/kg doses at 10 days.

14. Demonstration of $PL11-PEG_{20\ KDa}$, $PL12-PEG_{20\ KDa}$ and $PL13-PEG_{20\ KDa}$ Linker Reactivity with Albumin As indicated above, the majority of the cysteine thiols present in commercial grade albumin are capped, and so a reduction step is necessary prior to conjugation with linker molecules.

Method:

Albumin (221 µM) was reduced with dithiothreitol (DTT) (1 mM) in phosphate-buffered saline (PBS) pH 7.0 containing ethylenediaminetetraacetic acid (EDTA) (1 mM) for 1 hour at room temperature (RT), followed by desalting on a Nap-5 column and quantification by UV measurement. Conjugation of 20 KDa PEG-PL-12 (10 molar excess) or 20 KDa PEG-PL-13 (10 molar excess) to reduced albumin (20 µM) was performed in PBS, pH 7.4, 1 mM EDTA for 1 day at RT. Similarly, conjugation of 20 KDa PEG-maleimide (1.1 molar excess) to reduced albumin (20 µM) was performed in PBS, pH 7.4 containing 1 mM EDTA for 1 day at RT. The reactions were analysed on SDS-PAGE gel and quantification performed by analysis of protein band density on SDS-PAGE gel using ImageLab software (Biorad).

Figure 43:
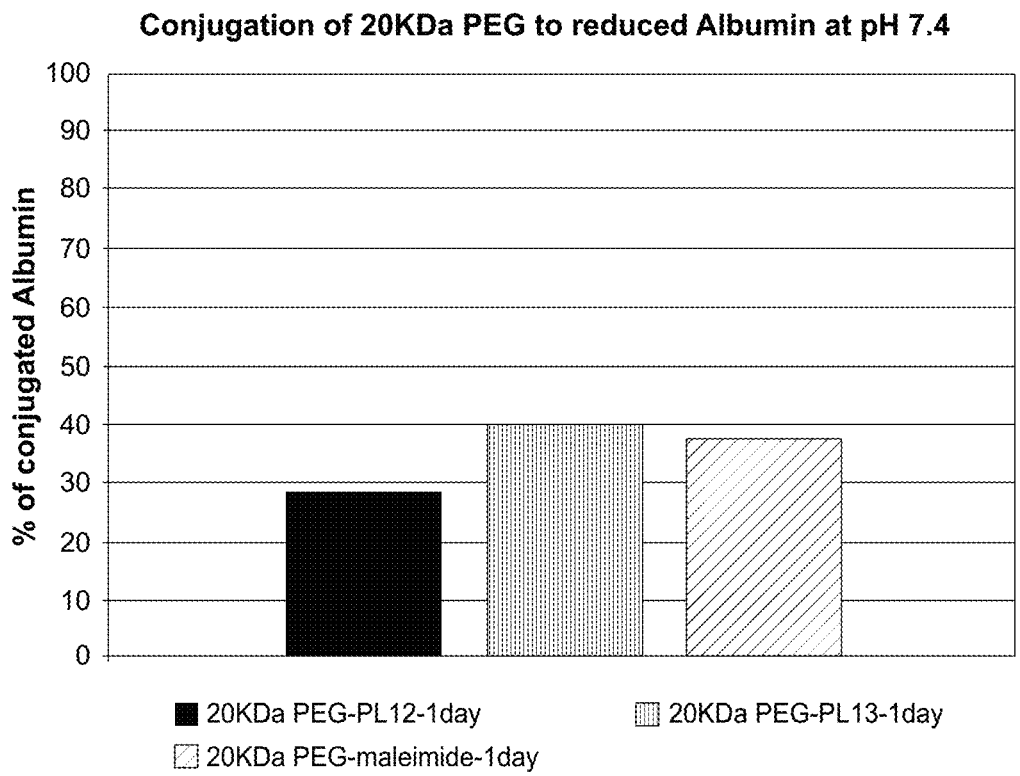
FIG. 43. Comparative data for conjugation of 20 KDa PEG-PL12 and PEG-PL13 versus 20 KDa PEG-maleimide to reduced albumin at pH 7.4

Results:

Only moderate conjugation yields were observed with reduced commercial grade albumin after 1 day. The conjugation of PL13 proceeded in a comparable yield to the maleimide control, whereas PL12 gave a slightly lower yield over the same time period. This is shown in FIG. 43.

15. Optimisation of PL11, PL12 and PL13 Conjugation to Albumin

The conjugation of the linker to albumin was determined at pH 5.5 for PL-11 and at pH 5.5, 6.5, 7.5, 8.0 and 8.5 for PL-12 and PL-13.

Method:

Conjugation of PL-11 (10 molar excess) to albumin (50 µM) was performed in 50 mM acetate-Na pH 5.5 for 24 hours at 37° C. Conjugation of PL-12 and PL-13 (10 molar excess) to albumin (50 µM) was performed in the following buffers: 50 mM acetate-Na pH 5.5; PBS 1 mM EDTA pH 6.5; PBS 1 mM EDTA pH 7.5; 100 mM phosphate; 1 mM EDTA pH 8.0; and 100 mM carbonate-Na, 1 mM EDTA pH 8.5; for 24 hours at 37° C.

Upon completion, all albumin samples were desalted on a Nap-5 column into PBS buffer (pH 7.4). The conjugation efficiency was quantified by Ellman's assay. Ellman's assay detects and quantifies free cysteine residues by reacting of 5,5'-Dithio-bis-(2-nitrobenzoic acid) with free thiol groups. The conjugation of linker molecules to the free thiol group of 34Cys in albumin blocks the detection of these groups by Ellman's reagent in comparison to the unconjugated albumin control. A decrease in the concentration of detectable free thiols was used to quantify amount of linker molecule conjugated to the albumin.

Figure 44A:
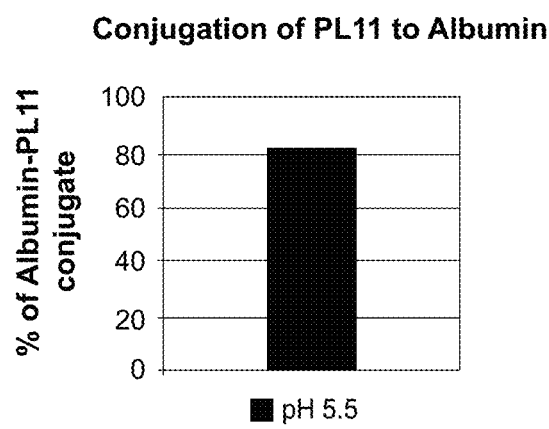
FIG. 44. Optimisation of PL11 (A), PL12 (B) and PL13 (C) conjugation to albumin.
Figure 44B:
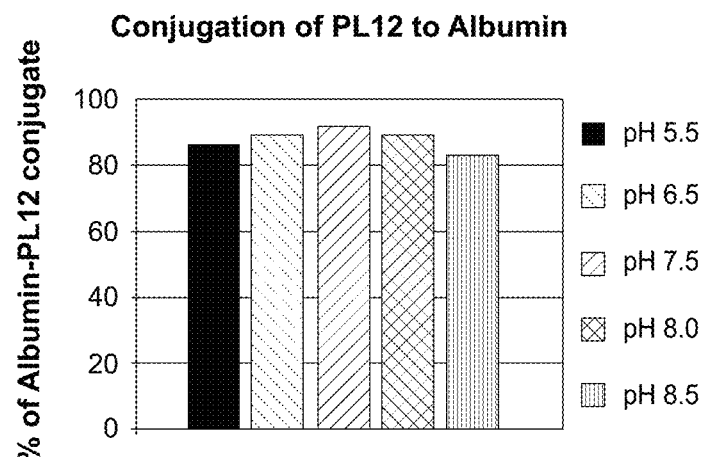
Figure 44C:
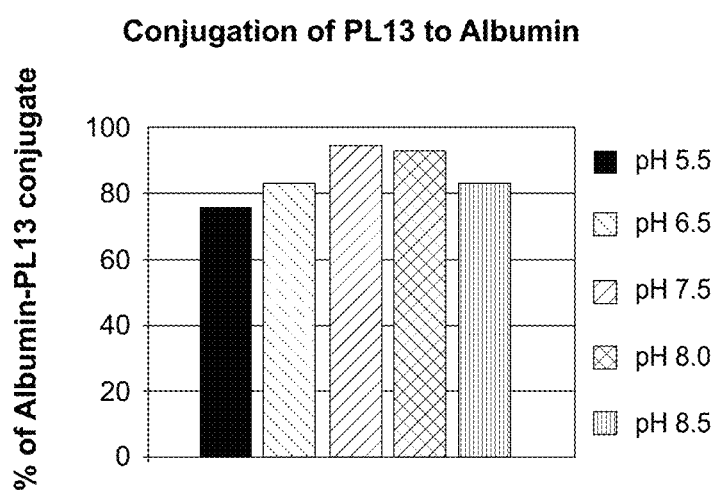

Results:

Conjugation of PL-11 to albumin at pH 5.5 proceeded in an 82% yield. The optimum pH for conjugation of PL-12 (91%) and PL-13 (94%) was determined to be pH 7.5. These results are shown in FIG. 44.

16. Demonstration of linker-albumin conjugate stability by ESI-MS

In addition, Albumin-PL11, Albumin-PL12 and Albumin-PL13 conjugates were analysed by ESI-MS.

Method:

Conjugation of PL-11 (20 molar excess) to albumin (50 µM) was performed in PBS containing EDTA (1 mM) at pH 6.5 for 24 hours at 37° C. Conjugation of PL-12 and PL-13 (10 molar excess) to albumin (50 µM) was performed in PBS containing EDTA (1 mM) at pH 7.5 for 24 hours at 37° C. The albumin-linker conjugates were analysed by ESI-MS.

Figure 45:
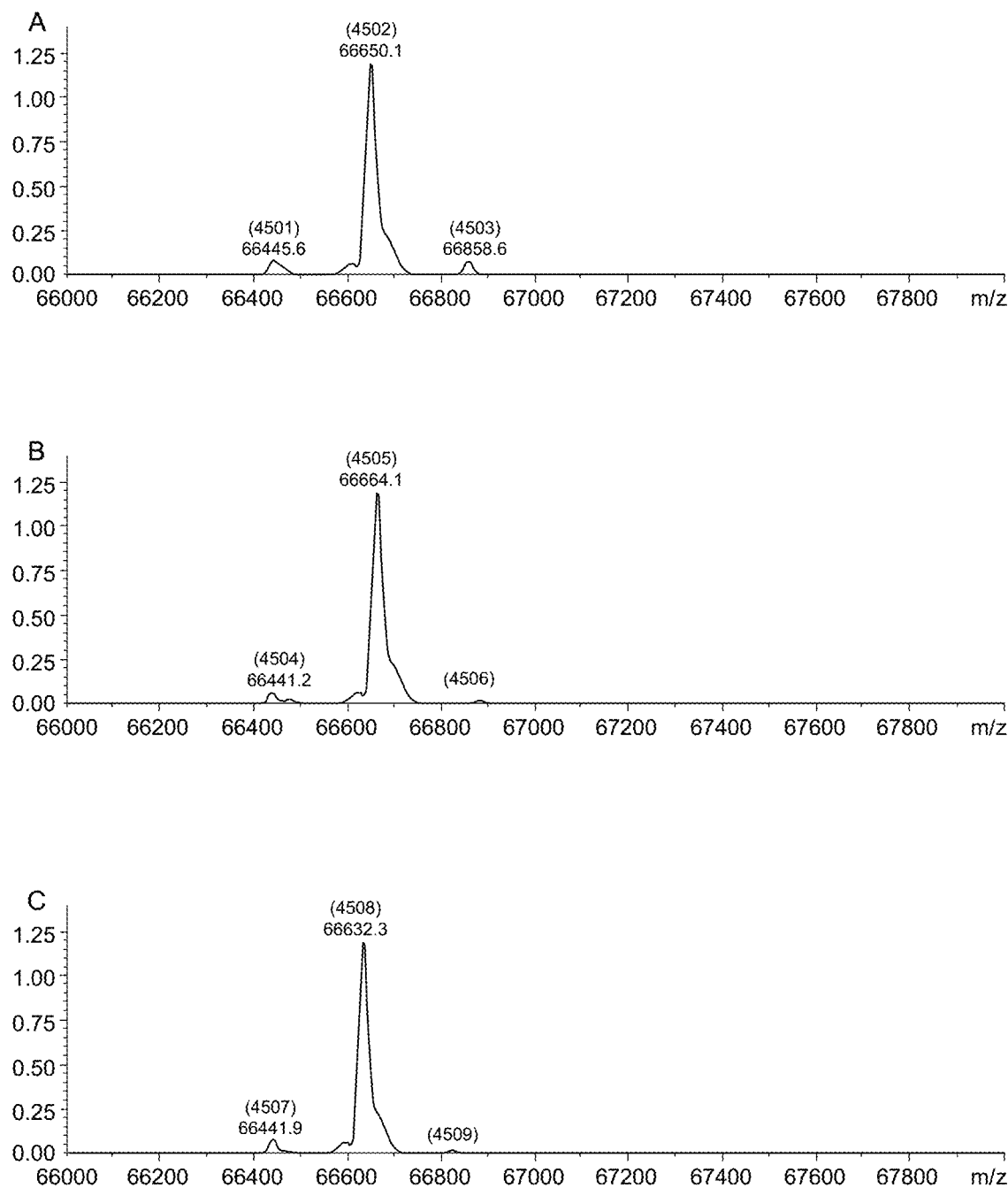
FIG. 45. Analysis of PL11 (A), PL12 (B) and PL13 (C) conjugation to albumin by ESI-MS.

Results:

FIG. 45 shows the ESI-MS results obtained for the albumin-PL-11 conjugation (A), albumin-PL-12 conjugation (B) and the albumin-PL-13 conjugation (C).

The following albumin species were detected and quantified based on MS signal intensity (note that MW stands for molecular weight):

Albumin-PL11
Unconjugated albumin—6%
Expected MW of unconjugated Albumin—66440 (Detected MW=66445 Da)
Albumin-PL11 conjugate—90%
Expected MW of albumin-PL11—66649 Da (Detected MW=66650 Da)
Albumin conjugated to two PL11~4%
Expected MW of albumin-2-PL11—66858 Da (Detected MW=66858 Da)
Albumin-PL12
Unconjugated Albumin—1%
Expected MW of unconjugated Albumin—66440 (Detected MW=66441 Da)
Albumin-PL12—92%
Expected MW of albumin-PL12—66663 Da (Detected MW=66664 Da)
Albumin conjugated to two PL12—7%
Expected MW of albumin-2-PL12—66886 Da (Detected MW=66886 Da)
Albumin-PL13
Unconjugated Albumin—5%
Expected MW of unconjugated Albumin—66440 (Detected MW=66441 Da)
Albumin-PL13—94%
Expected MW of albumin-PL13—66631 Da (Detected MW=66632 Da)
Albumin conjugated to two PL13—1%
Expected MW of albumin-2-PL13—66822 Da (Detected MW=D66822a)

In particular, with reference to FIG. 45, peaks (4501), (4504) and (4507) correspond to unreacted and oxidised albumin, peaks (4502), (4505) and (4508) correspond to single conjugate albumin and peaks (4503), (4506) and (4509) correspond to double conjugate albumin.

17. Demonstration of Stability of Albumin-linker Conjugates in Glutathione

The stability of albumin-linker molecule conjugates was determined in the presence of excess glutathione and analysed by ESI-MS over a period of 7 days.

Method:

Samples of the albumin-PL-12 conjugate (0.5 mg/mL) were incubated with reduced glutathione (1 mM) in PBS (pH 7.4) at 37° C. for 7 days. The samples were analysed on ESI-MS.

Figure 46:
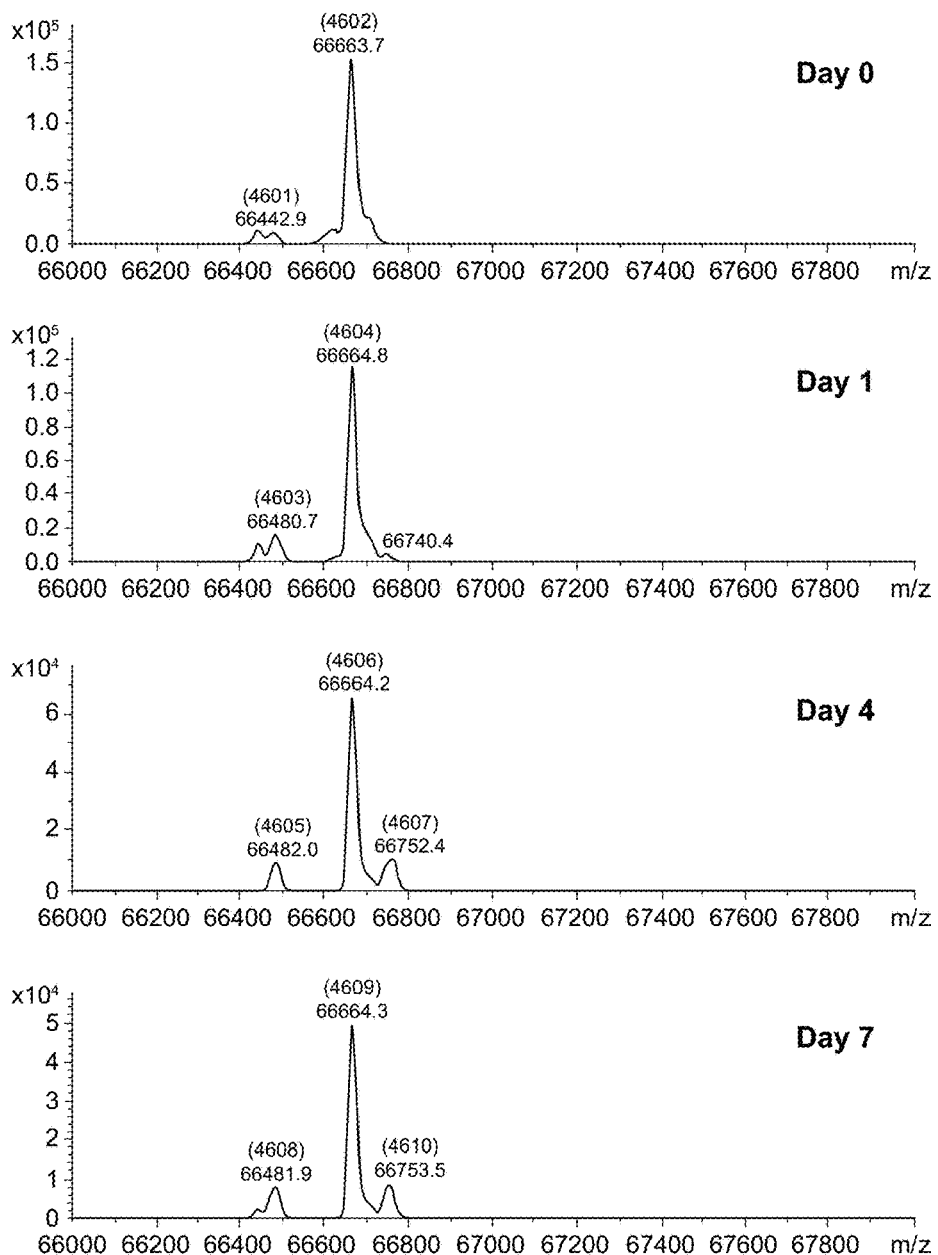
FIG. 46. Stability of Albumin-PL-12 conjugate in the presence of 1 mM GSH demonstrated by ESI-MS.

Results:

FIG. 46 shows the results obtained for the albumin-PL-12 conjugate as a representative example. A similar trend was observed for the albumin-PL-11 and albumin-PL-13 conjugates.

FIG. 46 shows the ESI-MS results at day 0, 1, 4 and 7. In FIG. 46, peaks (4601), (4603), (4605) and (4608) correspond to albumin, peaks (4602), (4604), (4606) and (4609) correspond to albumin-PL12 conjugate and peaks (4607) and (4610) correspond to GSH-albumin. Accordingly, it is shown that:

The major species present is the albumin-PL12 conjugate (MW=~66664 Da)
Upon incubation with 1 mM glutathione, there is a very slow increase in Albumin-GSH signal (~8%, MW=66752 Da) starting at 4 day of incubation with glutathione and reaching ~13% on $7^{th}$ day of incubation.

It can be concluded that albumin-linker conjugates of the present invention demonstrate good stability in a competitive environment.

Figure 47:
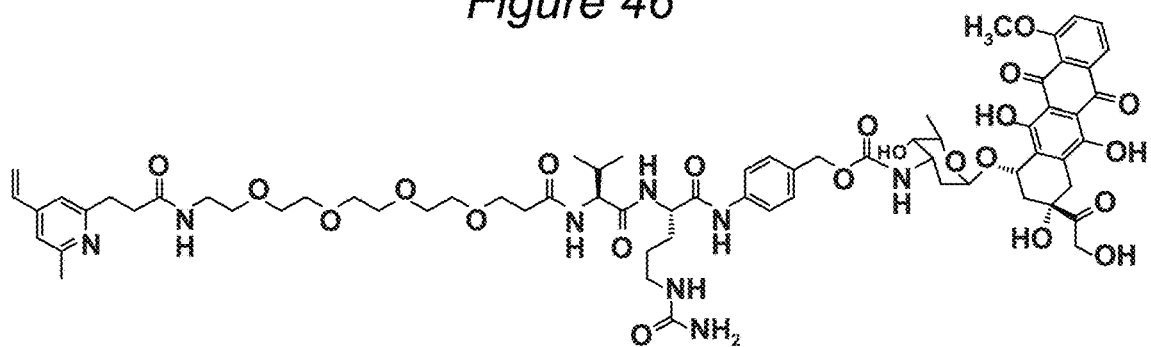
FIG. 47. Structure of PL13-NH-PEG4-val-cit-4-aminobenzoyl-Doxorubicin linker.

18. Generation of Albumin-doxorubicin Conjugates Using Linkers According to the Present Invention Method:

Albumin, Thioalbumin (single cysteine mutant) and Thioalbumin (double cysteine mutant) were conjugated to 14, 20 and 30 fold excess of PL13-NH-PEG4-val-cit-4-aminobenzoyl-doxorubicin linker (FIG. 47), respectively. Reactions were carried out in 147 mM sodium phosphate pH 7.5, in the presence of 10% v/v DMA and 0.6 mM EDTA, at 37° C. for 2 days in the dark. After this time, the reactions were desalted on PD-10 columns equilibrated in PBS buffer pH 7.4.

The conjugation efficacy was determined by UV-Vis spectroscopy using the doxorubicin absorbance and extinction coefficient at 495 nm ($\varepsilon$=8030 $M^{-1}$, $cm^{-1}$) and that of albumin at 280 ($\varepsilon$=34445 $M^{-1}$, $cm^{-1}$), with correction for doxorubicin absorbance at 280 nm according to the equation:

$$\text{Albumin concentration} = \frac{(\text{Abs 280 nm} - (0.724 \times \text{Abs 495 nm}))}{\varepsilon 280\ nm}$$

The extent of albumin-doxorubicin conjugate aggregation was determined by analysis on non-reducing SDS-PAGE and SEC chromatography.

10 µl of each albumin-doxorubicin conjugate in SDS-PAGE loading buffer was loaded on NuPAGE 4-12% Bis-Tris gel and run for 45 minutes at 200 V. The native fluorescence properties of doxorubicin were used to visualise albumin-doxorubicin conjugates before staining of a gel with Coomassie dye for protein species.

5 µl of each conjugate was loaded on to a SEC HPLC column equilibrated with 150 mM sodium phosphate buffer at pH 7.0 and eluted at flow rate of 1 mL/min with detection at 280 nm.

Figure 48:
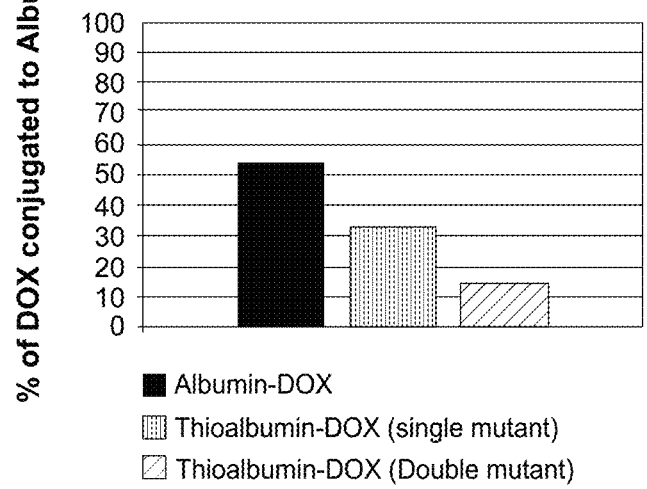
FIG. 48. Comparative data for conjugation of PL13-NH-PEG4-val-cit-4-aminobenzoyl-doxorubicin linker to albumin, thioalbumin (single mutant) and thioalbumin (double mutant).

Results:

Conjugation of doxorubicin to wild-type albumin and albumin mutants resulted in yields of 55% for albumin, 32% for thioalbumin-single mutant and 14% for thioalbumin-double mutant (see FIG. 48).

Figure 49:
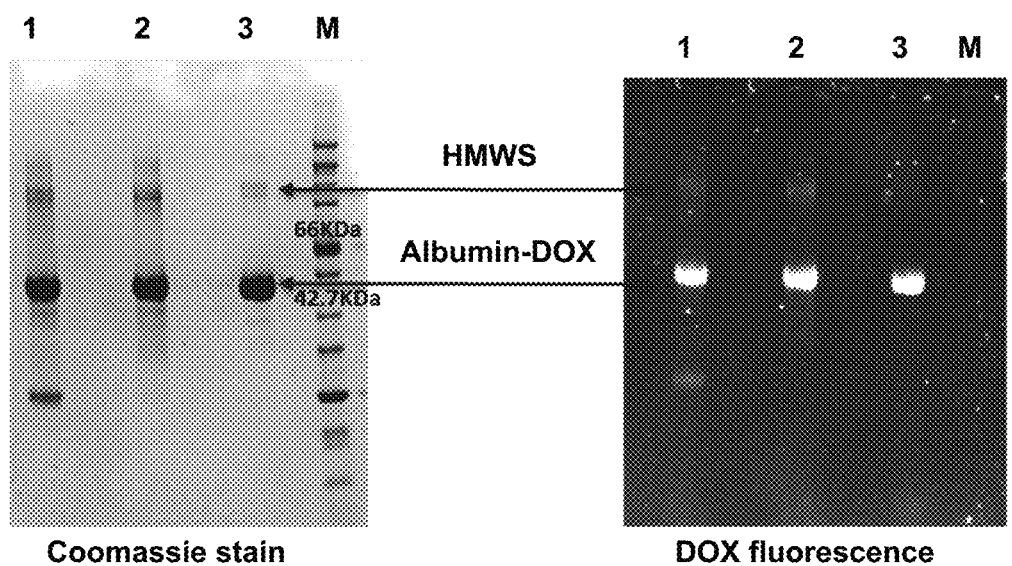
FIG. 49. Non-reducing SDS-PAGE analysis of albumin-PL13-NH-PEG4-val-cit-4-aminobenzoyl-doxorubicin conjugates. (1) Thioalbumin-double mutant-DOX; (2) Thioalbumin-single mutant-DOX; (3) Albumin-DOX; (M)-protein marker.

SDS-PAGE analysis revealed the presence of a small amount of high molecular weight species (HMWS) in all albumin-doxorubicin samples (see FIG. 49). This data is consistent with that observed by SEC analysis (see FIG. 50). In addition, SDS-PAGE analysis confirmed the conjugation of doxorubicin to albumin observed by UV-Vis spectroscopy (see FIG. 49, DOX fluorescence)

Figure 50:
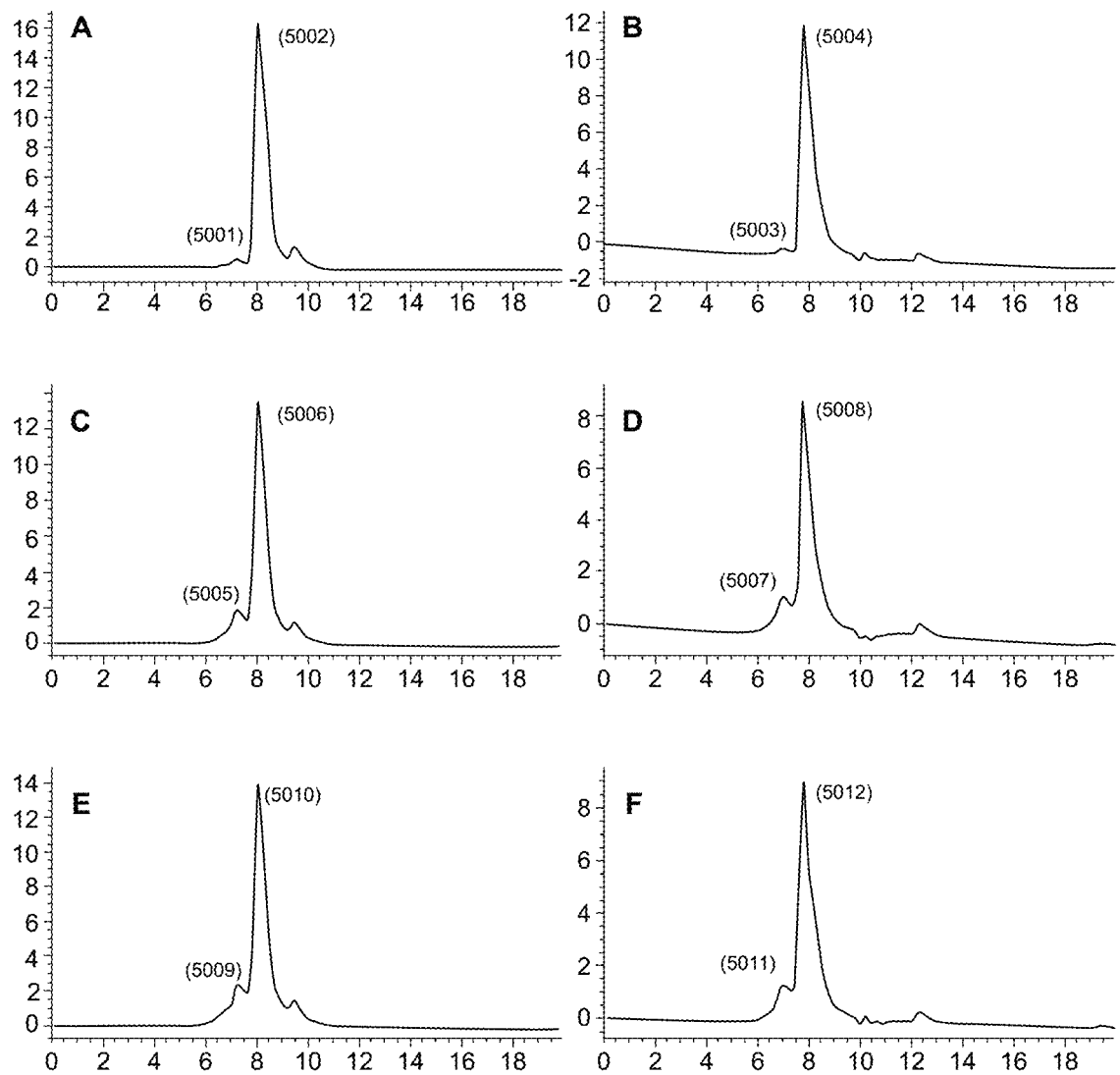
FIG. 50. SEC analysis of albumin-PL13-NH-PEG4-val-cit-4-aminobenzoyl-doxorubicin conjugates: Albumin (A) and albumin-DOX conjugate (B); Thioalbumin (single mutant) (C) and Thioalbumin-DOX (single mutant) (D); Thioalbumin (double mutant) (E) and Thioalbumin-DOX (double mutant) (F).

Albumin-doxorubicin and thioalbumin-doxorubicin conjugates were analysed along with non-conjugated albumin and non-conjugated thioalbumin controls by SEC chromatography. Analysis of the doxorubicin conjugates showed that the monomer content was approximately 97.6% for albumin-DOX, 86.8% for albumin-DOX (single mutant) and 88.2% for albumin-DOX (double mutant), (see FIGS. 50 B, D and F). Non-conjugated albumin and thioalbumin controls (see FIGS. 50 A, C and E) showed similar monomer and high molecular weight species content to the doxorubicin conjugated species. In particular, FIG. 50 shows peaks at (5001), (5003), (5005), (5007), (5009) and (5011) corresponding to the presence of the HMWS and peaks at (5002), (5004), (5006), (5008), (5010) and (5012) corresponding to the monomer content.

Both thioalbumin mutants show a higher tendency to aggregate than wild-type albumin: 13.2-14.5% for thioalbumin (single mutant) and 11.8-16.6% for thioalbumin (double mutant), compared to 2.4-2.6% for native albumin. Analysis of these samples confirmed that conjugation of doxorubicin via PL13-PEG4-val-cit-4-aminobenzoyl is well tolerated and produced no additional aggregation aggregation (see FIGS. 50 A, C and F).

Accordingly, it has been shown that the protein drug conjugates of the present invention provide suitable alternatives to known protein drug conjugates. Moreover, the linker incorporated into the protein drug conjugates of the present invention enables safe and effective drug delivery by successfully binding the drug to the protein and retaining the drug until the target tissue is reached.

The invention claimed is:

1. A protein drug conjugate comprising:
a globular protein comprising a thiol group, wherein the globular protein is an antibody or fragment thereof;
a linker; and
a drug;
wherein the linker comprises a nitrogen containing heterocyclic aromatic ring comprising a vinyl substituent represented by the following formulae

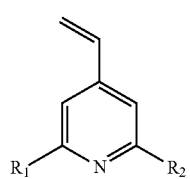

(III)

wherein:
$R_1$ comprises
$(CH_2)_n$—C(O)—R;
wherein:
$R_2$ is selected from the same group of molecules as $R_1$, hydrogen, or an alkyl group,
n is any integer from 0 to 10,
m is any integer between 0 and 10, and
R is a hydroxide (OH), amine or a poly-(alkylene glycol) group,
wherein the globular protein is conjugated to the linker through the conjugation of the thiol group to the vinyl substituent, and
wherein the drug is conjugated to the linker through the $R_1$ group, the $R_2$ group, or the $R_1$ group and the $R_2$ group.

2. The protein drug conjugate according to claim 1, wherein the antibody is a monoclonal antibody.

3. The protein drug conjugate according to claim 1, wherein the drug is selected from the group consisting of a cytotoxin, a therapeutic peptide, and a polypeptide.

4. The protein drug conjugate according to claim 3, wherein the cytotoxin is a biologically active cytotoxic material.

5. The protein drug conjugate according to claim 3, wherein the cytotoxin is an anticancer drug.

6. The protein drug conjugate according to claim 1, wherein the linker comprises a poly-(alkylene glycol) group.

7. The protein drug conjugate according to claim 6, wherein the poly-(alkylene glycol) group is a polyethylene glycol (PEG).

8. The protein drug conjugate according to claim 6, wherein the poly-(alkylene glycol) structure is provided with at least one reactive functional group including hydroxy, amine, carboxylic acid, alkyl halide, azide, succinimidyl, or thiol groups.

9. The protein drug conjugate according to claim 1, which further comprises an extender linker.

10. The protein drug conjugate according to claim 9, wherein said extender linker is enzyme cleavable.

11. A method of producing the protein drug conjugate of claim 1, the method comprising contacting the protein with the linker which is bound to the drug.

12. The method of claim 11, the method comprising contacting the protein having at least one reactive thiol group with the linker which comprises a functionalising reagent comprising a nitrogen containing heterocyclic aromatic ring having a vinyl substituent capable of reacting with at least one free thiol group of the protein, wherein the linker functionalising reagent is covalently linked to a poly-(alkylene glycol) molecule.

13. The method according to claim 11, the method comprising an initial step of reacting a precursor functionalising reagent comprising a nitrogen containing heterocyclic aromatic ring having a vinyl substituent with a poly-(alkylene glycol) molecule to produce the functionalising reagent.

14. The method according to claim 11, the method comprising an initial step of modifying the protein to produce a variant polypeptide having a thiol group at at least one desired position of the polypeptide.

* * * * *